United States Patent
Hodges et al.

(10) Patent No.: US 9,352,015 B2
(45) Date of Patent: *May 31, 2016

(54) ANTIMICROBIAL PEPTIDES

(75) Inventors: Robert S. Hodges, Denver, CO (US);
Ziqing Jiang, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 747 days.

This patent is subject to a terminal disclaimer.

(21) Appl. No.: 12/793,666

(22) Filed: Jun. 3, 2010

(65) Prior Publication Data

US 2011/0028386 A1     Feb. 3, 2011

Related U.S. Application Data

(60) Provisional application No. 61/217,915, filed on Jun. 5, 2009.

(51) Int. Cl.
*A61K 38/16* (2006.01)

(52) U.S. Cl.
CPC ..................................... *A61K 38/16* (2013.01)

(58) Field of Classification Search
None
See application file for complete search history.

(56) References Cited

U.S. PATENT DOCUMENTS

| | | | |
|---|---|---|---|
| 5,593,866 A | 1/1997 | Hancock et al. | |
| 5,688,767 A | 11/1997 | Hancock et al. | |
| 5,707,855 A | 1/1998 | Hancock et al. | |
| 5,789,377 A | 8/1998 | Hancock et al. | |
| 5,798,336 A | 8/1998 | Travis et al. | |
| 5,877,274 A | 3/1999 | Hancock et al. | |
| 6,040,435 A | 3/2000 | Hancock et al. | |
| 6,057,291 A | 5/2000 | Hancock et al. | |
| 6,172,185 B1 | 1/2001 | Hancock et al. | |
| 6,191,254 B1 | 2/2001 | Falla et al. | |
| 6,288,212 B1 | 9/2001 | Hancock et al. | |
| 6,297,215 B1 | 10/2001 | Hancock et al. | |
| 6,337,317 B1 | 1/2002 | Hancock et al. | |
| 6,358,921 B1 | 3/2002 | Kondejewski et al. | |
| 6,465,429 B1 | 10/2002 | Hancock et al. | |
| 6,696,559 B1 | 2/2004 | Selsted | |
| 6,747,007 B2 | 6/2004 | Hancock et al. | |
| 6,818,407 B2 | 11/2004 | Hancock et al. | |
| 6,872,806 B1 | 3/2005 | Kondejewski et al. | |
| 6,884,776 B1 | 4/2005 | Nibbering et al. | |
| 6,906,035 B2 | 6/2005 | Hancock et al. | |
| 8,252,737 B2 * | 8/2012 | Hodges et al. | 514/2.4 |
| 2002/0035061 A1 | 3/2002 | Krieger et al. | |
| 2003/0021795 A1 | 1/2003 | Houston et al. | |
| 2003/0228324 A1 | 12/2003 | Malcom et al. | |
| 2005/0277589 A1 | 12/2005 | Arranz | |
| 2007/0244044 A1 | 10/2007 | O'Neil | |
| 2008/0027006 A1 | 1/2008 | Tripet et al. | |
| 2009/0005300 A1 * | 1/2009 | Hodges et al. | 514/12 |
| 2010/0099614 A1 * | 4/2010 | Hodges et al. | 514/12 |
| 2011/0028386 A1 * | 2/2011 | Hodges et al. | 514/2.7 |

FOREIGN PATENT DOCUMENTS

| | | |
|---|---|---|
| WO | 91/19512 | 12/1991 |
| WO | 00/12528 | 3/2000 |
| WO | 02/40536 | 5/2002 |
| WO | 2005/077103 | 8/2005 |
| WO | 2006/065977 | 6/2006 |
| WO | WO 2006/065977 * 6/2006 | ............. A61K 38/16 |

OTHER PUBLICATIONS

International Search Report and Written Opinion, mailed Dec. 18, 2006, for International Application No. PCT/US05/45393, filed Dec. 15, 2005, 5 pp. (related subject matter, common inventor).
International Search Report and Written Opinion, mailed Mar. 16, 2010, for corresponding International Application No. PCT/US09/59717, filed Oct. 6, 2009, 11 pp.
International Search Report and Written Opinion, mailed Dec. 9, 2010, for related International Application No. PCT/US10/37308, filed Jun. 3, 2010, 16 pp. (related subject matter, common inventor).
Al-Bakri et al. (2005) "Influence of Gentamicin and Tobramycin on Binary Biofilm Formation by Co-Cultures of *Burkholderia cepacia* and *Pseudomonas aeruginosa*," *J. Basic Microbiol.* 45(5):392-396.
Andreu et al. (Jan. 1992) "Shortened Cecropin A-Melittin Hybrids," *FEBS Lett.* 296(2):190-194.
Andreu et al. (1998) "Animal Antimicrobial Peptides: An Overview," *Biopolymers* 47:415-433.
Avrahami et al. (2002) "Conjugation of a Magainin Analogue with Lipophilic Acids Controls Hydrophobicity, Solution Assembly, and Cell Selectivity," *Biochemistry* 41:2254-2263.
Baumann et al. (1974) "A Molecular Model of Membrane Excitability," J. Supramol Struct 2:538-557.
Bland et al. (2001) "All-D-Cecropin B: Synthesis, Conformation, Lipopolysaccharide Binding, and Antibacterial Activity," *Molecular and Cellular Biochemistry* 218:105-111.
Blondelle et al. (1991) "Hemolytic and Antimicrobial Activities of the Twenty-Four Individual Omission Analogues of Melittin," *Biochemistry* 30:4671-4678.

(Continued)

*Primary Examiner* — Maury Audet
(74) *Attorney, Agent, or Firm* — Sheridan Ross P.C.

(57) ABSTRACT

Disclosed are antimicrobial peptides with useful or superior properties such as antimicrobial activity, desirable levels of hemolysis, and advantageous therapeutic index against various microorganisms, especially *Pseudomonas aeruginosa, Acinetobacter baumannii* and *Staphylococcus aureus*. Also provided are methods of to control microbial growth and pharmaceutical compositions to treat or prevent microbial infections. Certain peptides are disclosed utilizing a structure-based rational modification of antimicrobial peptide D1, with single D-/L-amino acid substitutions or charged residue substitutions in or near the center of the peptide on the nonpolar or polar face, or peptides with one or more amino acids in the D configuration, and peptides with all amino acids in the D configuration. Modified peptide analogs herein can demonstrate one or more properties such as improved antimicrobial activity, specificity, and resistance to degradation. Compositions disclosed herein are useful as antibiotics, including as broad spectrum antibiotics.

21 Claims, 20 Drawing Sheets

(56) References Cited

OTHER PUBLICATIONS

Blondelle et al. (1992) "Design of Model Amphipathic Peptides Having Potent Antimicrobial Activities," *Biochemistry* 31(50):12688-12694.

Blondelle et al. (1995) "Induced Conformational States of Amphipathic Peptides in Aqueous/Lipid Environments," *Biophys. J.* 68:351-359.

Blondelle et al. (1999) "Lipid-Induced Conformation and Lipid-Binding Properties of Cytolytic and Antimicrobial Peptides: Determination and Biological Specificity," *Biochim. Biophys. Acta* 1462:89-108.

Bodmann, K.F. (2005) "Current Guidelines for the Treatment of Severe Pneumonia and Sepsis," *Chemotherapy* 51:227-233.

Boman, H.G. (2003) "Antibacterial Peptides: Basic Facts and Emerging Concepts," *Journal of Internal Medicine* 254:197-215.

Bowman et al. (2006) "The structure and synthesis of the fungal cell wall," *Bioessays* 28:799-808.

Brogden, K.A. (2005) "Antimicrobial Peptides: Pore Formers or Metabolic Inhibitors in Bacteria," www.nature.com/reviews/micro 3:238-250.

Brown, A.E. (1990) "Overview of Fungal Infections in Cancer Patients," *Semin Oncol* 17(3):2-5.

Carver et al. (2003) "The Design of Jemboss: A Graphical User Interface to EMBOSS," *Bioinformatics* 19(14):1837-1843.

Chen et al. (2002) "Determination of Stereochemistry Stability Coefficients of Amino Acid Side-Chains in an Amphipathic α-Helix," *J. Peptide Res.* 59:18-33.

Chen et al. (2004) "Optimum Concentration of Trifluoroacetic Acid for Reversed-Phase Liquid Chromatography of Peptides Revisited," *J. Chromatogr. A* 1043:9-18.

Chen, et al. (2005) "Rational Design of α-Helical Antimicrobial Peptides with Enhanced Activities and Specificity/Therapeutic Index", The Journal of Biological Chemistry, 280(13):12316-12329, JBC Papers in Press.

Chen et al. (2006) "Comparison of Biophysical and Biologic Properties of α-Helical Enantiomeric Antimicrobial Peptides," *Chem Biol Drug Des* 67:162-173.

Chen, et al. (2007) "Role of Peptide Hydrophobicity in the Mechanism of Action of α-Helical Antimicrobial Peptides", Antimicrobial Agents and Chemotherapy, 51(4):1398-1406, American Society for Microbiology.

Chen et al. (2007) "Preparative reversed-phase high-performance liquid chromatography collection efficiency for an antimicrobial peptide on columns of varying diameters (1 mm to 9.4 mm I.D.)," J. Chromatogr A 1140:112-120.

Christensen et al. (1988) "Channel-Forming Properties of Cecropins and Related Model Compounds Incorporated into Planar Lipid Membranes," *Proc. Nat. Acad. Sci. USA* 85:5072-5076.

Chu-Kung, et al. (2004) "Effect of Fatty Acid Conjugation on Antimicrobial peptide Activity", University of California, 6 pp., Santa Barbara, CA.

Cribbs et al. (1997) "All-D-Enantiomers of Beta-Amyloid Exhibit Similar Biological Properties to All-L-Beta-Amyloids," *J. Biol. Chem.* 272:7431-7436.

Dathe et al. (1997) "Hydrophobicity, Hydrophobic Moment and Angle Subtended by Charged Residues Modulate Antibacterial and Hemolytic Activity of Amphipathic Helical Peptides," *FEBS Lett.* 403:208-212.

Dathe et al. (1996) "Peptide Helicity and Membrane Surface Charge Modulate the Balance of Electrostatic and Hydrophobic Interactions with Lipid Bilayers and Biological Membranes," *Biochemistry* 35:12612-12622.

Daum, G. (1985) "Lipids of mitochondria," *Biochim. Biophys. Acta* 822:1-42.

De Lucca et al. (2000) "D-Cecropin B: Proteolytic Resistance, Lethality for Pathogenic Fungi and Binding Properties," *Medical Mycology* 38:301-308.

Dennison et al. "Factors Determining the Efficacy of Alpha-Helical Antimicrobial Peptides," (2003) *Protein Pept Lett* 10(5):497-502.

Dennison et al. "Amphiphilic α-Helical Antimicrobial Peptides and Their Structure/Function Relationships," (2005) *Protein Pept Lett* 12:31-39.

Devaux et al. (1985) "Specificity of lipid-protein interactions as determined by spectroscopic techniques," *Biochim. Biophys. Acta.* 822:63-125.

Devine et al. (2002) "Cationic Peptides: Distribution and Mechanisms of Resistance," *Curr. Pharm. Des.* 8:703-714.

Dolan, J.W. (2002) "Temperature Selectivity in Reversed-Phase High Performance Liquid Chromatography," *J. Chromatogr. A* 965:195-205.

Duclohier et al. (1989) "Antimicrobial Peptide Magainin I from Xenopus Skin Forms Anion-Permeable Channels in Planar Lipid Bilayers," *Biophys. J.* 56:1017-1021.

Durden et al. (Sep. 1997) "Fungal Infections in HIV-Infected Patients," *Seminars Cutan Med Surg* 16(3):200-212.

Ehrenstein et al. (1977) "Electrically Gated Ionic Channels in Lipid Bilayers," *Q. Rev. Biophys.* 10:1-34.

Eisenberg et al. (1982) "The Helical Hydrophobic Moment: A Measure of the Amphiphilicity of a Helix," *Nature* 299:371-374.

Elkin et al. (2003) "Pseudomonal Infection in Cystic Fibrosis: The Battle Continues," *Exp. Rev. Anti. Infect. Ther.* 1(4):609-618.

Elmquist et al. (2003) "In Vitro Uptake and Stability Study of pVEC and its All-D Analog," *Biol. Chem.* 384:387-393.

Gabriel et al. (Jun. 2007) "Infectious disease: Connecting innate immunity to biocidal polymers," *Mater Sci Eng R Rep* 57:28-64.

Ganz et al. (1994) "Defensins," *Curr. Opin Immunol.* 6:584-589.

Georgopapadakou et al. (Apr. 1994) "Human Mycoses: Drugs and Targets for Emerging Pathogens," *Science* 264:371-373.

Guo et al. (1986) "Prediction of Peptide Retention Times in Reversed-Phase High-Performance Liquid Chromatography. I. Determination of Retention Coefficients of Amino Acid Residues Using Model Synthetic Peptides," *J. Chromatogr.* 359:499-518.

Hamamoto et al. (2002) "Antimicrobial Activity and Stability to Proteolysis of Small Linear Cationic Peptides with D-Amino Acid Substitutions," *Microbiol. Immunol.* 46(11):741-749.

Hancock, R.E.W. (1997) "Peptide Antibiotics," *Lancet* 349:418-422.

Hancock et al. (1998) "Cationic Peptides: A New Source of Antibiotics," *Trends Biotechnol.* 16:82-88.

Hancock et al. (2002) "Role of Membranes in the Activities of Antimicrobial Cationic Peptides," *FEMS Microbiol. Lett.* 206:143-149.

Hoiby et al. (1990) "Cystic Fibrosis. 1. *Pseudomonas aeruginosa* Infection in Cycstic Fibrosis and its Management," *Thorax* 45:881-884.

Hong et al. (1999) "Effect of $_D$-Amino Acid Substitution on the Stability, the Secondary Structure, and the Activity of Membrane-Active Peptide," *Biochem. Pharmacol.* 58:1775-1780.

Jenssen et al. (Jul. 2006) "Peptide Antimicrobial Agents," *Clin Microbial Rev* 19(3):491-511.

Jiang et al. (published online Dec. 20, 2007) "Effects of Net Charge and the Number of Positively Charged Residues on the Biological Activity of Amphipathic α-Helical Cationic Antimicrobial Peptides," *Biopolymers* 90(3):369-383.

Jiang, et al. (published online Nov. 19, 2008) "Effects of Hydrophobicity on the Antifungal Activity of α-Helical Antimicrobial Peptides", Chem Biol Drug Des, 72:483-495.

Jiang et al. (conference Jun. 7-12, 2009) "Effect of Net Positive Charge and Charge Distribution on the Polar Face of Amphipathic α-Helical Antimicrobial Peptides on their Biological and Biophysical Properties," in Peptides: Breaking Away, Proceedings of the Twenty-First American Peptide Symposium, edited by Michel Lebl, pp. 266-267, Bloomington, IN.

Jiang et al. (2011) "Rational Design of α-Helical Antimicrobial Peptides to Target Gram-negative Pathogens, *Acinetobacter baumannii* and *Pseudomonas aeruginosa*: Utilization of Charge, 'Specificity Determinants,' Total Hydrophobicity, Hydrophobe Type and Location as Design Parameters to Improve the Therapeutic Ratio," *Chem Biol Drug Des* 77:225-240.

Khaled et al. (1978) "Hydrogen-Deuterium Substitution and Solvent Effects on the Nitrogen-15 Nuclear Magnetic Resonance of Gramicidin S: Evaluation of Secondary Structure," *Biochemistry* 17(13):2490-2494.

(56) References Cited

OTHER PUBLICATIONS

Kiyota et al. (1996) "Design and Synthesis of Amphiphilic α-Helical Model Peptides with Systematically Varied Hydrophobic-Hydrophilic Balance and Their Interaction with Lipid- and Bio-Membranes," *Biochemistry* 35:13196-13204.
Kondejewski et al. (Jan. 2002) "Optimization of Microbial Specificity ion Cyclic Peptides by Modulation of Hydrophobicity within a defined Structural Framework," *J. Biol. Chem.* 277(1):67-74.
Kondejewski et al. (May 1999) "Dissociation of Antimicrobial and Hemolytic Activities in Cyclic Peptide Diastereomers by Systematic Alterations in Amphipathicity," *J. Biol. Chem.* 274(19):13181-13192.
Kontoyiannis et al. (2002) "Antifungal drug resistance of pathogenic fungi," Lancet 359:1135-1144.
Kovacs et al. (2006) "Determination of Intrinsic Hydrophilicity/Hydrophobicity of Amino Acid Side-Chains in Peptides in the Absence of Nearest-Neighbor or Conformational Effects," *Biopolymers (Peptide Science)* 84:283-297.
Kustanovich et al. (2002) "Structural Requirements for Potent Versus Selective Cytotoxicity for Antimicrobial Dermaseptin s4 Derivatives," *J. Biol. Chem.* 277:16941-16951.
Lee et al. (2003) "Structure-Activity Relationships of de novo Designed Cyclic Antimicrobial Peptides Based on Gramicidin S," *Biopolymers (Peptide Science)* 71:28-48.
Lee et al. (2004) "Effects of Single $_D$-Amino Acid Substitutions on Disruption of β-Sheet Structure and Hydrophobicity in Cyclic 14-Residue Antimicrobial Peptide Analogs Related to Gramicidin S," *J. Peptide Res.* 63(2):69-84.
Lee et al. (2003) "A Novel Method to Measure Self-Association of Small Amphipathic Molecules: Temperature Profiling in Reversed-Phase Chromatography," *J. Biol. Chem.* 278:22918-22927.
Liu et al. (2002) "Effect of Variations in the Structure of a Polyleucine-Based α-Helical Transmembrane Peptide on Its Interaction with Phosphatidylcholine Bilayers," *Biochemistry* 41(29):9197-9207.
Liu et al. (2004) "Effect of Variations in the Structure of a Polyleucine-Based α-Helical Transmembrane Peptide on its Interaction with Phosphatidylethanolamine Bilayers," *Biophys. J.* 87:2470-2482.
Liu et al. (2004) "Effect of Variations in the Structure of a Polyleucine-Based α-Helical Transmembrane Peptide on Its Interaction with Phosphatidylglycerol Bilayers," *Biochemistry* 43(12):3679-3687.
Liu et al. (Mar. 24, 2006) "Toll-Like Receptor Triggering of a Vitamin D-Mediated Human Antimicrobial Response", Science, 311:1770-1773.
Lugtenberg et al. (1983) "Molecular Architecture and Functioning of the Outer Membrane of *Escherichia coli* and Other Gram-Negative Bacteria," *Biochim. Biophys. Acta* 737:51-115.
Lustig et al. (1996) "Alternative Splicing Determines the Binding of Platelet-Derived Growth Factor (PDGF-AA) to Glycosaminoglycans," *Biochemistry* 35:12077-12085.
Mant et al. (1993) "The Role of Amphipathic Helices in Stabilizing Peptide and Protein Structure," *The Amphipathic Helix*, Epand, R.M. ed., CRC Press, Boca Raton, FL, Chapter 3, pp. 39-64.
Mant et al. (2002) "Reversed-Phase Liquid Chromatography as a Tool in the Determination of the Hydrophilicity/Hydrophobicity of Amino Acid Side-Chains at a Ligand-Receptor Interface in the Presence of Different Aqueous Environments: II. Effect of Varying Peptide Ligand Hydrophobicity," *J. Chromatogr. A* 972(1):61-75.
Mant et al. (2002) "Reversed-Phase Liquid Chromatography as a Tool in the Determination of the Hydrophilicity/Hydrophobicity of Amino Acid Side-Chains at a Ligand-Receptor Interface in the Presence of Different Aqueous Environments: I. Effect of Varying Receptor Hydrophobicity," *J. Chromatogr. A* 972(1):45-60.
Mant et al. (2003) "Temperature Profiling of Polypeptides in Reversed-Phase Liquid Chromatography. I. Monitoring of Dimerization and Unfolding of Amphipathic α-Helical Peptides," *J. Chromatogr. A* 1009:29-43.

Mant et al. (2003) "Temperature Profiling of Polypeptides in Reversed-Phase Liquid Chromatography. II. Monitoring of Folding and Stability of Two-Stranded α-Helical Coiled Coils," *J. Chromatogr. A* 1009:45-59.
Mant, et al. (Dec. 2009) "Intrinsic Amino Acid Side-Chain Hydrophilicity/Hydrophobicity Coefficients Determined by Reversed-Phase High-Performance Liquid Chromato-graphy of Model Peptides: Comparison with Other Hydrophilicity/Hydrophobicity Scales", Biopolymers, 92(6):573-595.
Martineau, et al. (Jul. 2007) "Neutrophil-mediated innate immune resistance to mycobacteria", The Journal of Clinical Investigation, 117(7):1988-1994.
Matsuzaki, K. (1999) "Why and How are Peptide-Lipid Interactions Utilized for Self Defense? Magainins and Tachyplesins as Archetypes," *Biochim. Biophys. Acta* 1462:1-10.
McInnes et al. (May 2000) "Development of the Structural Basis for Antimicrobial and Hemolytic Activities of Peptides Based on Gramicidin S and Design of Novel Analogs Using NMR Spectroscopy," *J. Biol. Chem.* 275(19):14287-14294.
McPhillips et al. (1986) "Drug Testing in Humans," in *Modern Pharmacol*, 2$^{nd}$ ed., Little, Brown and Co., Boston, Chapter 9, pp. 127-133.
Monera et al. (1995) "Relationship of Side Chain Hydrophobicity and α-Helical Propensity on the Stability of the Single-Stranded Amphipathic α-Helix," *J. Peptide Sci.* 1:319-329.
Mootz et al. (Nov. 1997) "The Tyrocidine Biosynthesis Operon of *Bacillus brevis*: Complete Nucleotide Sequence and Biochemical Characterization of Functional Internal Adenylation Domains," *J. Bacteriol.* 179(21):6843-6850.
Neu, H.C. (Aug. 21, 1992) "The Crisis in Antibiotic Resistance," Science 257.5073:1064-1073.
Obritsch et al. (2005) "Nosocomial Infections Due to Multidrug-Resistant *Pseudomonas aeruginosa*: Epidemiology and Treatment Options," *Pharmacotherapy* 25(10):1353-1364.
Oren et al. (Jun. 1997) "A Repertoire of Novel Antibacterial Diastereomeric Peptides with Selective Cytolytic Activity," *J. Biol. Chem.* 272(23):14643-14649.
Oren et al. (1997) "Selective Lysis of Bacteria but Not Mammalian Cells by Diasteromers of Melittin: Structure-Function Study," *Biochemistry* 36(7):1826-1835.
Paya, C. V. (1993) "Fungal Infections in Solid-Organ Transplantation," Clin Infect Dis 16:677-688.
Pierce, G.E. (2005) *Pseudomonas aeruginosa, Candida albicans*, and Device-Related Nosocomial Infections: Implications, Trends, and Potential Approaches for Control, *J. Ind. Microbiol. Biotechnol.* 32:309-318.
Pouny et al. (1992) "Interaction of Antimicrobial Dermaseptin and its Fluorescently Labeled Analogues with Phospholipid Membranes," *Biochemistry* 31:12416-12423.
Powers et al. (2004) "Structure-Activity Relationships for the β-Hairpin Cationic Antimicrobial Peptide Polyphemusin I," *Biochim. Biophys. Acta.* 1698:239-250.
Purcell et al. (1995) "Induction of amphipathic helical peptide structures in RP-HPLC," *Pept. Res.* 8(3):160-170. (Abstract only).
Reddy et al. (2004) "Antimicrobial Peptides: Premises and Promises," *Int. J. Antimicrob. Agents* 24:536-547.
Salgado et al. (2001) "Membrane-Bound Structure and Alignment of the Antimicrobial β-Sheet Peptide Gramicidin S Derived from Angular and Distance Constraints by Solid-State $^{19}$F-NMR," *J. Biomol. NMR* 21:191-208.
Shai et al. (Mar. 1996) "Diastereomers of Cytolysins, a Novel Class of Potent Antibacterial Peptides," *J. Biol. Chem.* 271(13):7305-7308.
Shai, Y. (1999) "Mechanism of the Binding, Insertion and Destabilization of Phospholipid Bilayer Membranes by α-Helical Antimicrobial and Cell Non-Selective Membrane-Lytic Peptides," *Biochim. Biophys. Acta.* 1462:55-70.
Sitaram et al. (1999) "Interaction of Antimicrobial Peptides with Biological and Model Membranes: Structural and Charge Requirements for Activity," *Biochim. Biophys. Acta* 1462:29-54.
Sitaram et al. (2002) "Host-Defense Antimicrobial Peptides: Importance of Structure for Activity," *Curr. Pharm. Des.* 8:727-742.
Speight, T. (1987) "Clinical-Assessment of Drug Effects," in Fundamentals of Clinical Pharmacology, *Avery's Drug Treatment: Prin-*

(56) References Cited

OTHER PUBLICATIONS ciples and Practice of Clinical Pharmacology and Therapeutics, 3rd ed., Williams and Wilkins, Baltimore, Chapter I, p. 50-56.
Spilker, B. (1984) "Preliminary Considerations Relating to Study Design," *Guide to Clinical Studies and Developing Protocols*, Raven Press, Ltd., New York, Chapter 2, pp. 7-13.
Spilker, B. (1991) "Dosing Schedule," *Guide to Clinical Trials*, Raven Press, Ltd., New York, Chapter 14, pp. 93-101.
Steinberg et al. (Aug. 1997) "Protegrin-1: A Broad-Spectrum, Rapidly Microbicidal Peptide with In Vivo Activity," *Antimicrob. Agents Chemother.* 41(8):1738-1742.
Tachi et al. (2002) "Position-Dependent Hydrophobicity of the Antimicrobial Magainin Peptide Affects the Mode of Peptide-Lipid Interactions and Selective Toxicity," *Biochemistry* 41:10723-10731.
Tallarida et al. (1988) "Dose-Effect Relations," *Principles in General Pharmacology*, Springer-Verlag, New York, Chapter 2, pp. 18-20.
Tossi et al. (2000) "Amphipathic, α-Helical Antimicrobial Peptides," Biopolymers 55:4-30.
Travis, J. (1994) "Reviving the Antibiotic Miracle," *Science* 264:360-362.
Van 'T Hof et al. (Apr. 2001) "Antimicrobial Peptides: Properties and Applicability," *Biol. Chem.* 382:597-619.
Wade et al. (1990) "All-d Amino Acid-Containing Channel-Forming Antibiotic Peptides," *Proc. Nat. Acad. Sci. USA* 87:4761-4765.
Wakabayashi et al. (1999) "N-Acylated and D Enantiomer Derivatives of a Nonamer Core Peptide of Lactoferricin B Showing Improved Antimicribial Activity," *Antimicrob. Agents Chemother.* 43:1267-1269.
Wieprecht et al. (1997) "Peptide Hydrophobicity Controls the Activity and Selectivity of Magainin 2 Amide in Interaction with Membranes," *Biochemistry* 36:6124-6132.
Wieprecht et al. (1997) "Modulation of Membrane Activity of Amphipathic, Antibacterial Peptides by Slight Modifications of the Hydrophobic Moment," *FEBS Lett.* 417:135-140.
Zasloff, M. (Aug. 1987) "Magainins, A Class of Antimicrobial Peptides from *Xenopus* Skin: Isolation, Characterization of Two Active Forms, and Partial cDNA Sequence of a Precursor," *Proc. Nat. Acad. Sci. USA* 84:5449-5453.
Zhang et al. (1999) "Influence of Proline Residues on the Antibacterial and Synergistic Activities of Alpha-Helical Antimicrobial Peptides," *Biochemistry* 38:8102-8111.
Zhang et al. (1998) "Determinants of Recombinant Production of Antimicrobial Cationic Peptides and Creation of Peptide Variants in Bacteria," *Biochem. Biophys. Res. Commun.* 247:674-680.
Zhang et al. (Sep. 21, 2001) "Interaction of Cationic Antimicrobial Peptides with Model Membranes," *J. Biol. Chem.* 276(38):35714-35722.
Zhou et al. (1990) "Effect of Preferred Binding Domains on Peptide Retention Behavior in Reversed-Phase Chromatography: Amphipathic α-Helices," *Pept. Res.* 3(1):8-20.
Zhou et al. (1994) "α-Helical Propensities of Amino Acids in the Hydrophobic Face of an Amphipathic α-Helix," *Protein Pept. Lett.* 1(2):114-119.
Zilberstein et al. (1979) "Proton Electrochemical Gradient in *Escherichia coli* Cells and Its Relation to Active Transport of Lactose," *Biochemistry* 18(4):669-673.
European Supplemental Search Report, dated Nov. 22, 2012, corresponding to European Application No. 05854163.2 (filed Dec. 15, 2005), of an identical inventor and related subject matter, 12 pp.
Hartmann et al. (2003) "Comparison of Reversed-Phase Liquid Chromatography and Hydrophilic Interaction/Cation-Exchange Chromatography for the Separation of Amphipathic α-Helical Peptides with L- and D-Amino Acid Substitutions in the Hydrophilic Face," J Chromatography 1009:61-71.
Prosecution history for related U.S. Appl. No. 12/574,545, filed Oct. 6, 2009, (downloaded Aug. 17, 2012), last document dated May 18, 2012, 76 pp.
Prosecution history for related U.S. Appl. No. 11/721,915, filed Jun. 6, 2008 (downloaded Aug. 17, 2012), last document dated Aug. 8, 2012, 58 pp.
Examination Report, dated Dec. 9, 2011, for European patent application serial No. 05854163.2, filed Dec. 15, 2005, a related application, 4 pp.
Supplemental EP Search Report, dated May 22, 2012, corresponding to EP Application No. EP 09819768 (filed Oct. 6, 2009), a related application, 13 pp.
Hodges et al. (Oct. 2004) "Monitoring the hydrophilicity/ hydrophobocity of amino acid side-chains in the non-polar and polar faces of amphipathic α-helices by reversed-phase and hydrophilic interaction/cation-exchange chromatography," J Chromatography 1053:161-172.

\* cited by examiner

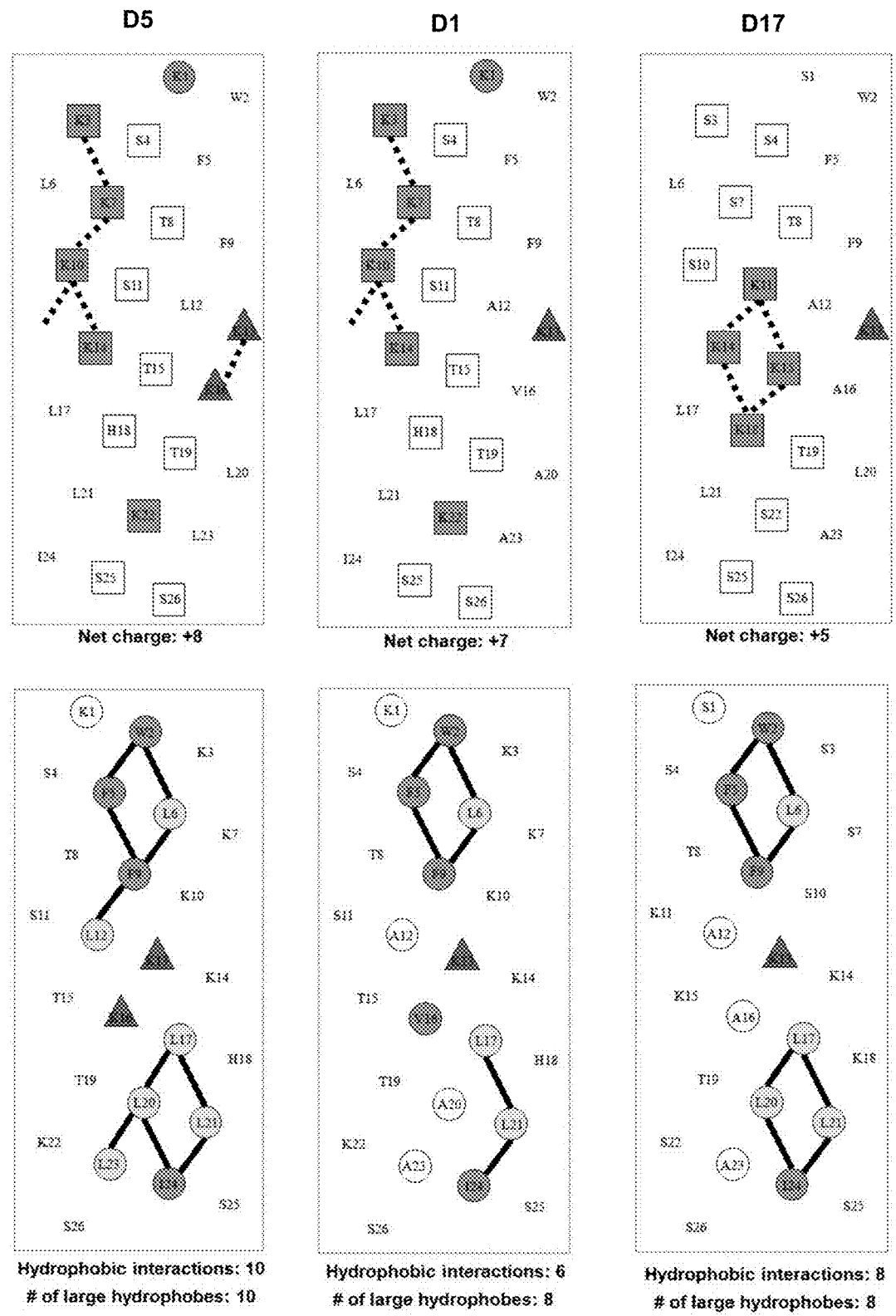
Fig. 1A1

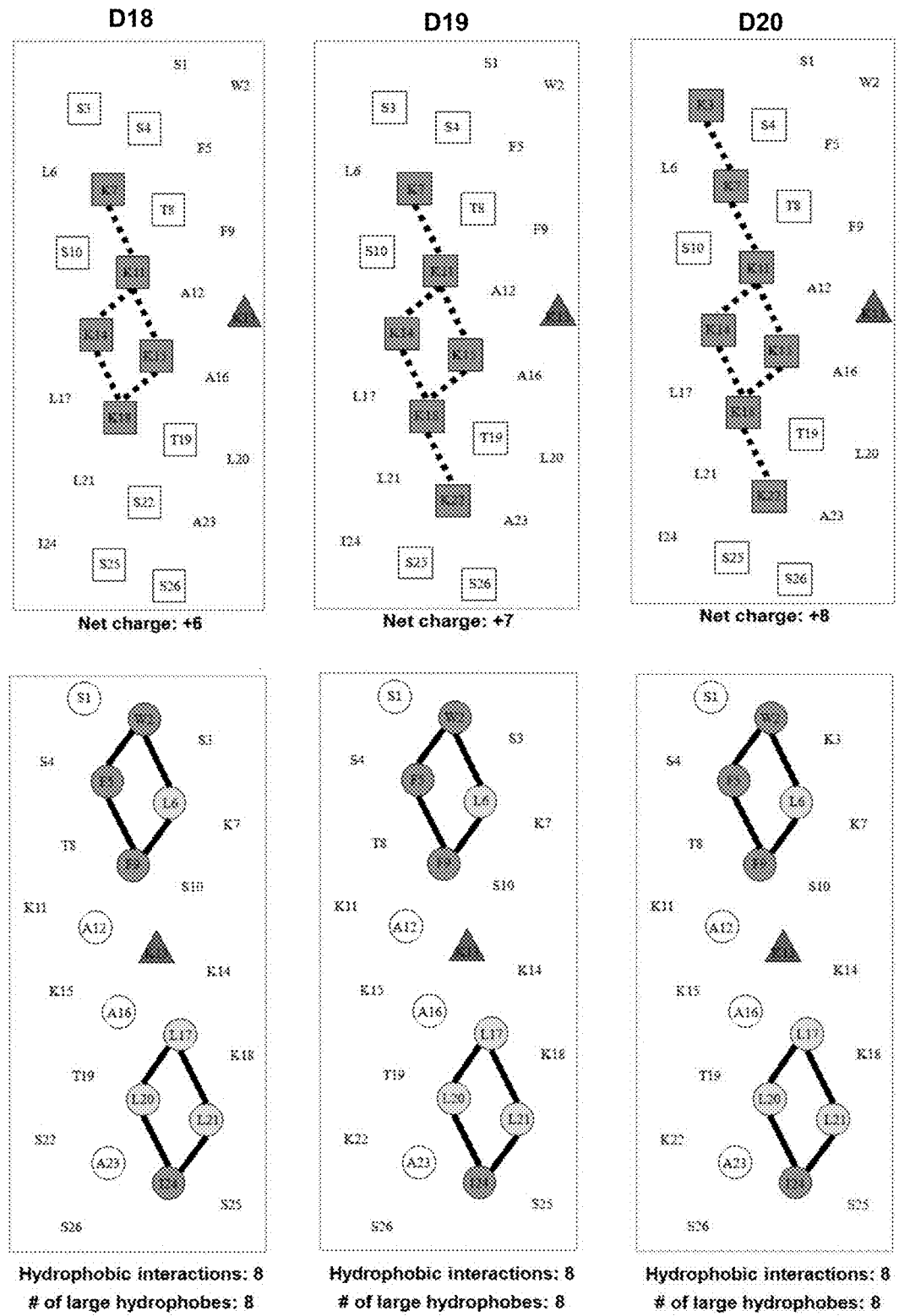
Fig. 1A2

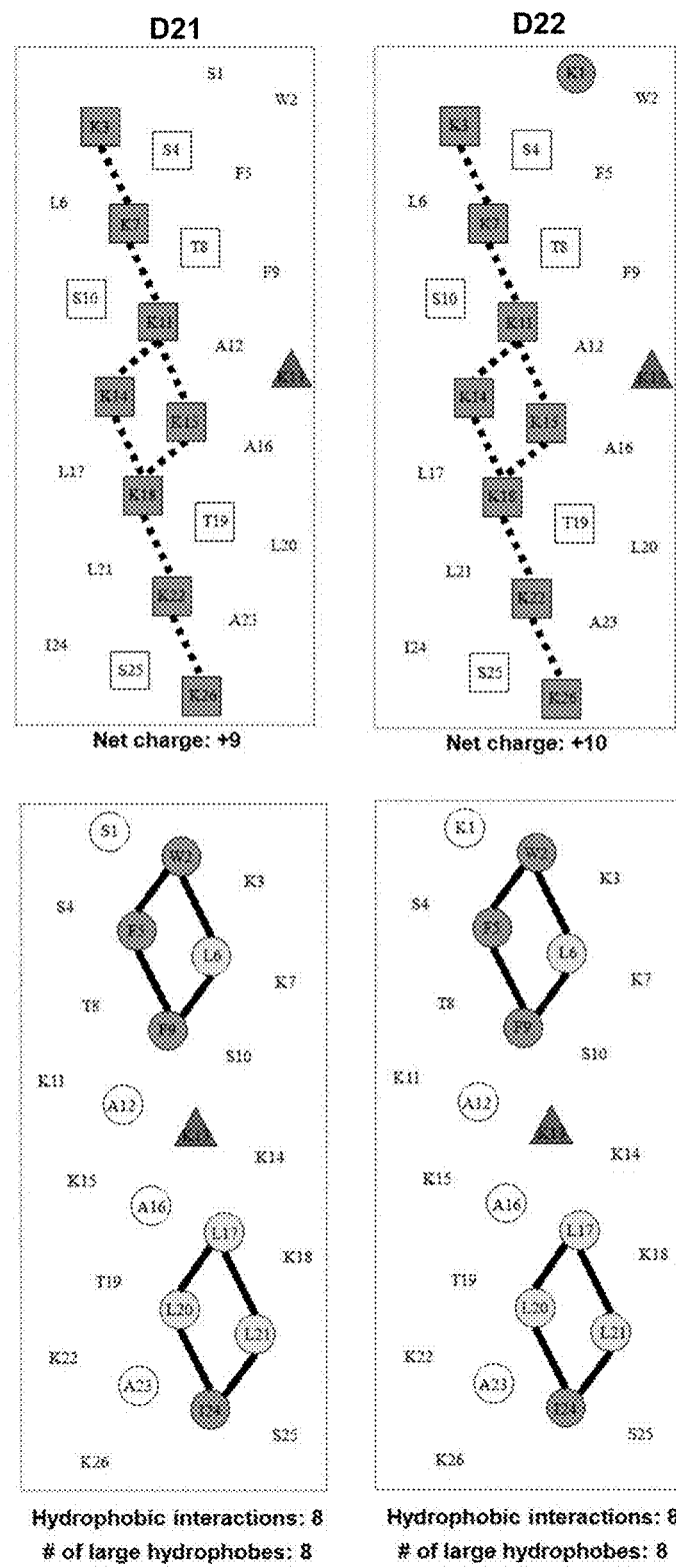
Fig. 1A3

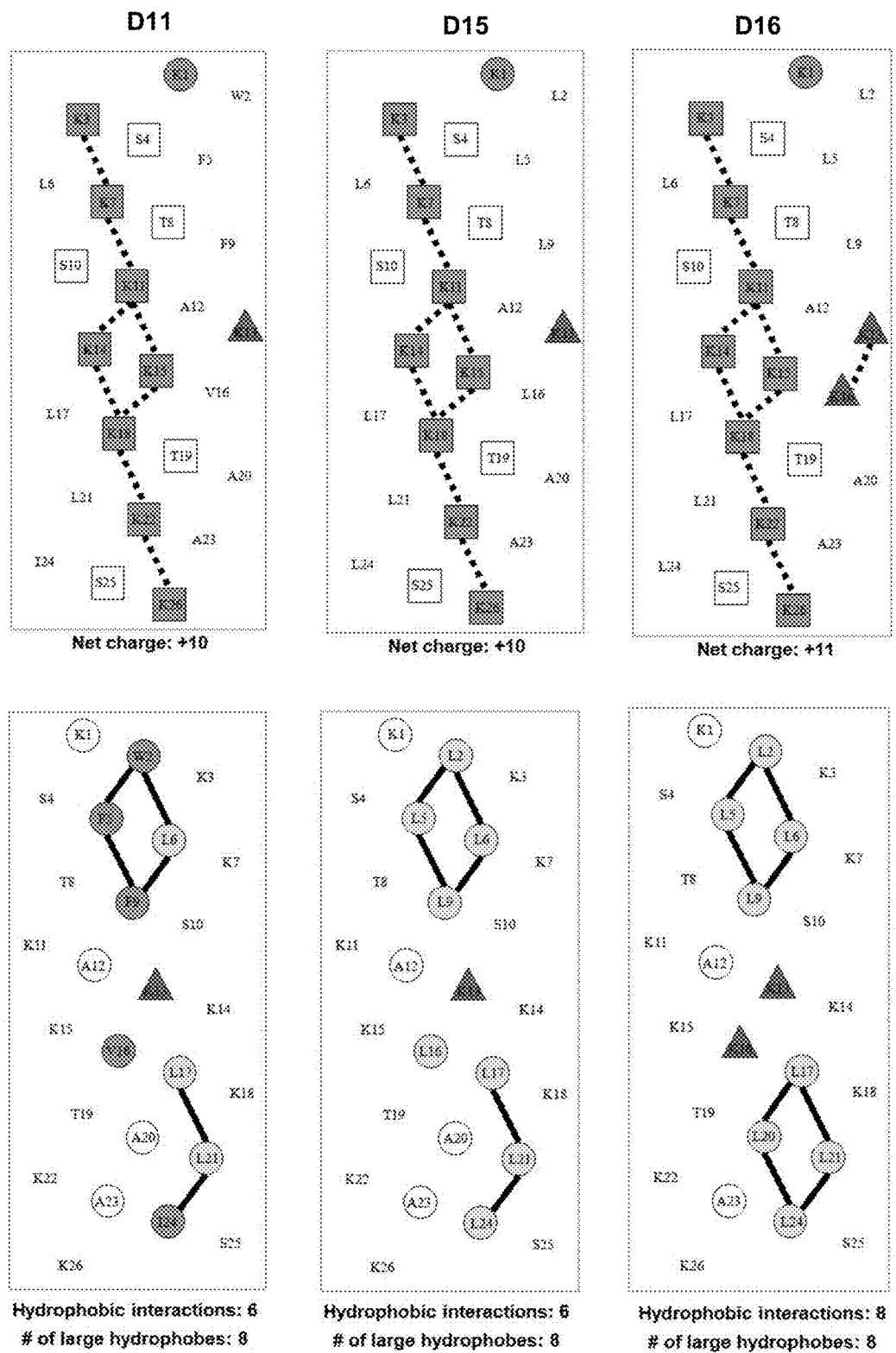
Fig. 1B1

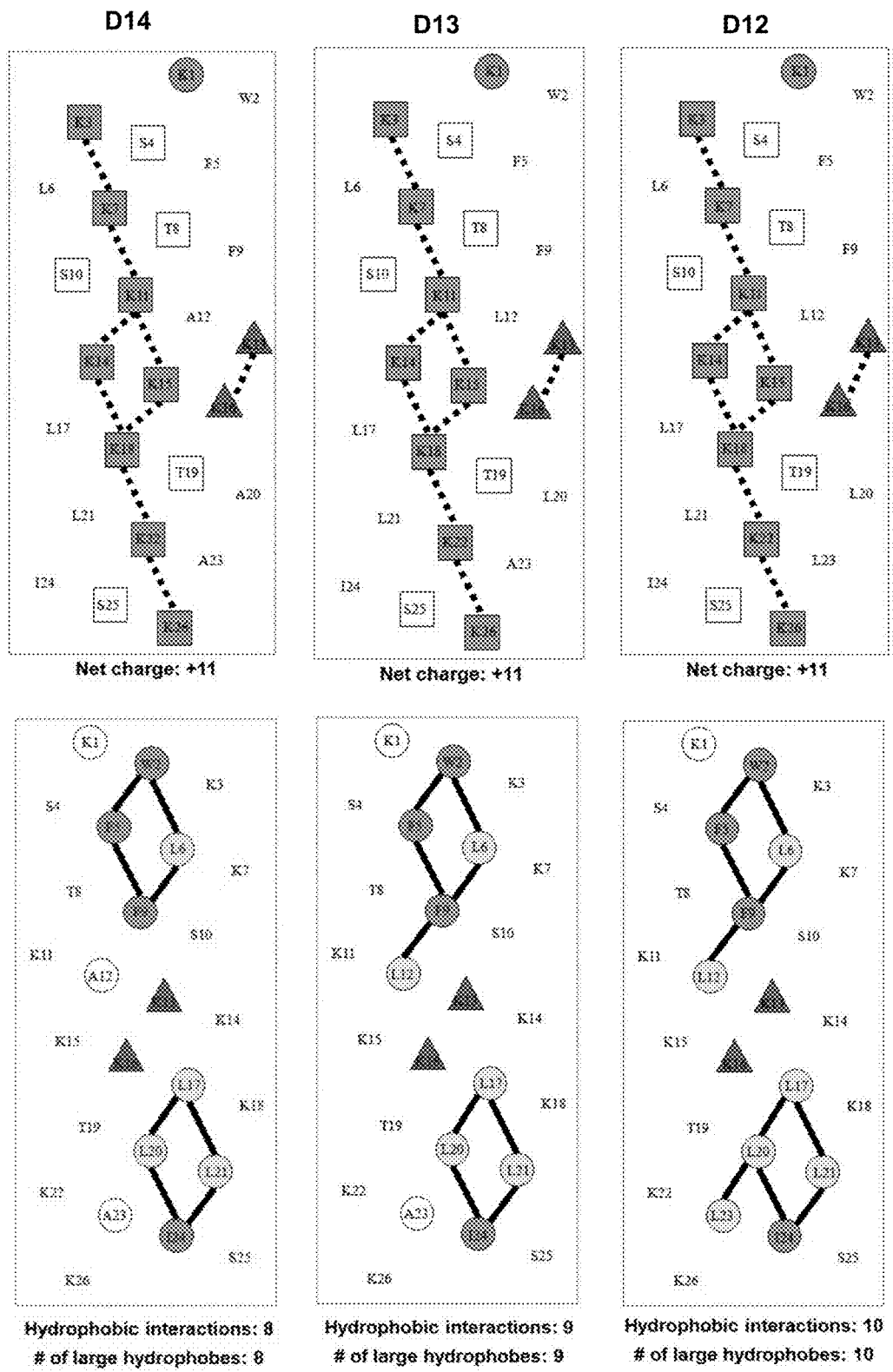
Fig. 1B2

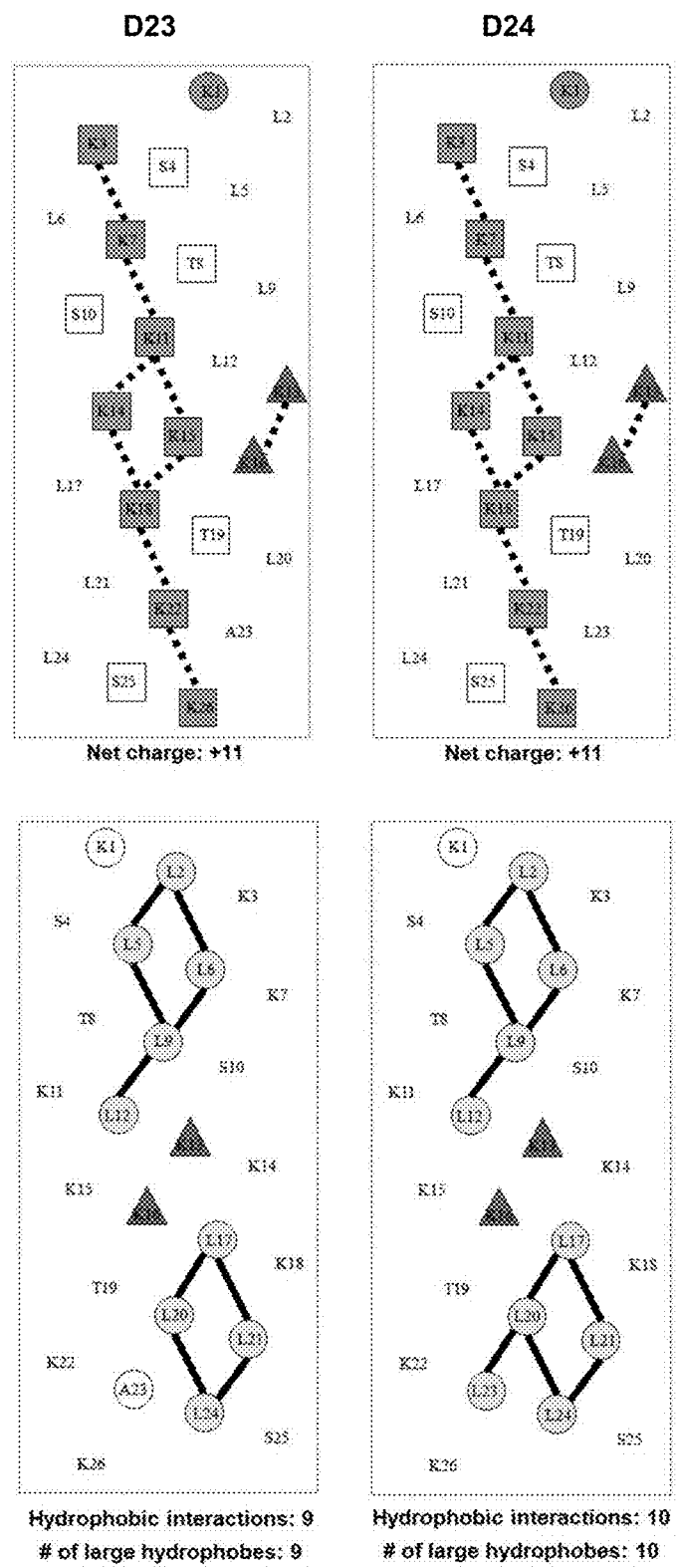
Fig. 1B3

Summary: *Acinetobacter baumannii* (11 Clinical Isolates)

| Peptide | Hemolytic activity | Antimicrobial activity | Therapeutic index |
|---|---|---|---|
| | $HC_{50}$ (μM) | MIC (μM) | $HC_{50}$/MIC |
| D1 | 140.9 | 1.1 | 128.1 |
| D11 | 254.1 | 0.6 | 423.5 |
| D22 | 81.3 | 0.8 | 101.6 |

Fig. 5B

Summary: *Acinetobacter baumannii* (11 Clinical Isolates)

| Peptide | Hemolytic activity HC$_{50}$ (μM) | Antimicrobial activity MIC (μM) | Therapeutic index HC$_{50}$/MIC |
|---|---|---|---|
| D14 | 351.5 | 0.8 | 439.4 |
| D22 | 81.3 | 0.8 | 101.6 |

Fig. 7-2

| Peptide | Hemolytic activity HC$_{50}$ (μM) | Antimicrobial activity MIC (μM) | Therapeutic index HC$_{50}$/MIC |
|---|---|---|---|
| D14 | 351.5 | 0.8 | 439.4 |
| D13 (D14 A12L) | 105.8 | 1.0 | 105.8 |
| D12 (D14 A12L, A23L) | 18.3 | 1.9 | 9.6 |
| D16 | 1342.0 | 0.4 | 3355.0 |
| D23 (D16 A12L) | 186.0 | 0.8 | 232.5 |
| D24 (D16 A12L, A23L) | 122.7 | 1.9 | 64.6 |

Fig. 8-3

Summary: *Acinetobacter baumannii* (11 Clinical Isolates)

| Peptide | Hemolytic activity HC$_{50}$ (μM) | Antimicrobial activity MIC (μM) | Therapeutic index HC$_{50}$/MIC |
|---|---|---|---|
| D1 | 140.9 | 1.1 | 128.1 |
| D16 | 1342.0 | 0.4 | 3355.0 |

Fig. 9B

```
SEQUENCE LISTING

<160> NUMBER OF SEQ ID NOS: 78

<210> SEQ ID NO 1
<211> LENGTH: 26
<212> TYPE: PRT
<213> ORGANISM: Artificial sequence
<220> FEATURE:
<223> OTHER INFORMATION: Synthetic peptide

<400> SEQUENCE: 1

Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25

<210> SEQ ID NO 2
<211> LENGTH: 26
<212> TYPE: PRT
<213> ORGANISM: Artificial sequence
<220> FEATURE:
<223> OTHER INFORMATION: Synthetic peptide

<400> SEQUENCE: 2
```

```
Lys Trp Lys Ser Phe Leu Lys Thr Phe Lys Ser Ala Leu Lys Thr Val
1               5                   10                  15

Leu His Thr Ala Leu Lys Ala Ile Ser Ser
            20                  25

<210> SEQ ID NO 3
<211> LENGTH: 26
<212> TYPE: PRT
<213> ORGANISM: Artificial sequence
<220> FEATURE:
<223> OTHER INFORMATION: Synthetic peptide

<400> SEQUENCE: 3

Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25

<210> SEQ ID NO 4
<211> LENGTH: 26
<212> TYPE: PRT
<213> ORGANISM: Artificial sequence
<220> FEATURE:
<223> OTHER INFORMATION: Synthetic peptide

<400> SEQUENCE: 4

Lys Trp Lys Ser Phe Leu Lys Thr Phe Lys Ser Ala Ala Lys Thr Val
1               5                   10                  15

Leu His Thr Ala Leu Lys Ala Ile Ser Ser
            20                  25

<210> SEQ ID NO 5
<211> LENGTH: 26
<212> TYPE: PRT
<213> ORGANISM: Artificial sequence
<220> FEATURE:
<223> OTHER INFORMATION: Synthetic peptide

<400> SEQUENCE: 5

Lys Trp Lys Ser Phe Leu Lys Thr Phe Lys Ser Ala Ser Lys Thr Val
1               5                   10                  15

Leu His Thr Ala Leu Lys Ala Ile Ser Ser
            20                  25

<210> SEQ ID NO 6
<211> LENGTH: 26
<212> TYPE: PRT
<213> ORGANISM: Artificial sequence
<220> FEATURE:
<223> OTHER INFORMATION: Synthetic peptide

<400> SEQUENCE: 6

Lys Trp Lys Ser Phe Leu Lys Thr Phe Lys Ser Ala Lys Lys Thr Val
1               5                   10                  15

Leu His Thr Ala Leu Lys Ala Ile Ser Ser
            20                  25

<210> SEQ ID NO 7
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
```

```
<222> LOCATION: (13)..(13)
<223> OTHER INFORMATION: L at losition 13 is D-Leu.

<400> SEQUENCE: 7

Lys Trp Lys Ser Phe Leu Lys Thr Phe Lys Ser Ala Leu Lys Thr Val
1               5                   10                  15

Leu His Thr Ala Leu Lys Ala Ile Ser Ser
            20                  25

<210> SEQ ID NO 8
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: V at position 13 is D-Val.

<400> SEQUENCE: 8

Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25

<210> SEQ ID NO 9
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: A at position 13 is D-Ala.

<400> SEQUENCE: 9

Lys Trp Lys Ser Phe Leu Lys Thr Phe Lys Ser Ala Ala Lys Thr Val
1               5                   10                  15

Leu His Thr Ala Leu Lys Ala Ile Ser Ser
            20                  25

<210> SEQ ID NO 10
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: S at position 13 is D-Ser.

<400> SEQUENCE: 10

Lys Trp Lys Ser Phe Leu Lys Thr Phe Lys Ser Ala Ser Lys Thr Val
1               5                   10                  15

Leu His Thr Ala Leu Lys Ala Ile Ser Ser
            20                  25

<210> SEQ ID NO 11
<211> LENGTH: 26
<212> TYPE: PRT
<213> ORGANISM: Artificial sequence
<220> FEATURE:
<223> OTHER INFORMATION: Synthetic peptide
<220> FEATURE:
```

```
<221> NAME/KEY: MISC_FEATURE
<222> LOCATION: (13)..(13)
<223> OTHER INFORMATION: K at position 13 is D-Lys.

<400> SEQUENCE: 11

Lys Trp Lys Ser Phe Leu Lys Thr Phe Lys Ser Ala Lys Lys Thr Val
1               5                   10                  15

Leu His Thr Ala Leu Lys Ala Ile Ser Ser
            20                  25

<210> SEQ ID NO 12
<211> LENGTH: 26
<212> TYPE: PRT
<213> ORGANISM: Artificial sequence
<220> FEATURE:
<223> OTHER INFORMATION: Synthetic peptide

<400> SEQUENCE: 12

Lys Trp Lys Ser Phe Leu Lys Thr Phe Lys Ser Ala Gly Lys Thr Val
1               5                   10                  15

Leu His Thr Ala Leu Lys Ala Ile Ser Ser
            20                  25

<210> SEQ ID NO 13
<211> LENGTH: 26
<212> TYPE: PRT
<213> ORGANISM: Artificial sequence
<220> FEATURE:
<223> OTHER INFORMATION: Synthetic peptide

<400> SEQUENCE: 13

Lys Trp Lys Ser Phe Leu Lys Thr Phe Lys Leu Ala Val Lys Thr Val
1               5                   10                  15

Leu His Thr Ala Leu Lys Ala Ile Ser Ser
            20                  25

<210> SEQ ID NO 14
<211> LENGTH: 26
<212> TYPE: PRT
<213> ORGANISM: Artificial sequence
<220> FEATURE:
<223> OTHER INFORMATION: Synthetic peptide

<400> SEQUENCE: 14

Lys Trp Lys Ser Phe Leu Lys Thr Phe Lys Ala Ala Val Lys Thr Val
1               5                   10                  15

Leu His Thr Ala Leu Lys Ala Ile Ser Ser
            20                  25

<210> SEQ ID NO 15
<211> LENGTH: 26
<212> TYPE: PRT
<213> ORGANISM: Artificial sequence
<220> FEATURE:
<223> OTHER INFORMATION: Synthetic peptide

<400> SEQUENCE: 15

Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25

<210> SEQ ID NO 16
<211> LENGTH: 26
```

```
<212> TYPE: PRT
<213> ORGANISM: Artificial sequence
<220> FEATURE:
<223> OTHER INFORMATION: Synthetic peptide

<400> SEQUENCE: 16

Lys Trp Lys Ser Phe Leu Lys Thr Phe Lys Val Ala Val Lys Thr Val
1               5                   10                  15

Leu His Thr Ala Leu Lys Ala Ile Ser Ser
            20                  25

<210> SEQ ID NO 17
<211> LENGTH: 26
<212> TYPE: PRT
<213> ORGANISM: Artificial sequence
<220> FEATURE:
<223> OTHER INFORMATION: Synthetic peptide

<400> SEQUENCE: 17

Lys Trp Lys Ser Phe Leu Lys Thr Phe Lys Lys Ala Val Lys Thr Val
1               5                   10                  15

Leu His Thr Ala Leu Lys Ala Ile Ser Ser
            20                  25

<210> SEQ ID NO 18
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: L at position 11 is D-Leu.

<400> SEQUENCE: 18

Lys Trp Lys Ser Phe Leu Lys Thr Phe Lys Leu Ala Val Lys Thr Val
1               5                   10                  15

Leu His Thr Ala Leu Lys Ala Ile Ser Ser
            20                  25

<210> SEQ ID NO 19
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: A at position 11 is D-Ala.

<400> SEQUENCE: 19

Lys Trp Lys Ser Phe Leu Lys Thr Phe Lys Ala Ala Val Lys Thr Val
1               5                   10                  15

Leu His Thr Ala Leu Lys Ala Ile Ser Ser
            20                  25

<210> SEQ ID NO 20
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
```

<223> OTHER INFORMATION: S at position 11 is D-Ser.

<400> SEQUENCE: 20

Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25

<210> SEQ ID NO 21
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: V at position 11 is D-Val.

<400> SEQUENCE: 21

Lys Trp Lys Ser Phe Leu Lys Thr Phe Lys Val Ala Val Lys Thr Val
1               5                   10                  15

Leu His Thr Ala Leu Lys Ala Ile Ser Ser
            20                  25

<210> SEQ ID NO 22
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: K at position 11 is D-Lys.

<400> SEQUENCE: 22

Lys Trp Lys Ser Phe Leu Lys Thr Phe Lys Lys Ala Val Lys Thr Val
1               5                   10                  15

Leu His Thr Ala Leu Lys Ala Ile Ser Ser
            20                  25

<210> SEQ ID NO 23
<211> LENGTH: 26
<212> TYPE: PRT
<213> ORGANISM: Artificial sequence
<220> FEATURE:
<223> OTHER INFORMATION: Synthetic peptide

<400> SEQUENCE: 23

Lys Trp Lys Ser Phe Leu Lys Thr Phe Lys Gly Ala Val Lys Thr Val
1               5                   10                  15

Leu His Thr Ala Leu Lys Ala Ile Ser Ser
            20                  25

<210> SEQ ID NO 24
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(26)
<223> OTHER INFORMATION: All amino acids are in D-conformation.

<400> SEQUENCE: 24

```
Lys Trp Lys Ser Phe Leu Lys Thr Phe Lys Ser Ala Lys Lys Thr Val
1               5                   10                  15

Leu His Thr Ala Leu Lys Ala Ile Ser Ser
            20                  25

<210> SEQ ID NO 25
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(26)
<223> OTHER INFORMATION: All amino acid except A at position 13 is in
      D-conformation.

<400> SEQUENCE: 25

Lys Trp Lys Ser Phe Leu Lys Thr Phe Lys Ser Ala Ala Lys Thr Val
1               5                   10                  15

Leu His Thr Ala Leu Lys Ala Ile Ser Ser
            20                  25

<210> SEQ ID NO 26
<211> LENGTH: 18
<212> TYPE: PRT
<213> ORGANISM: Artificial sequence
<220> FEATURE:
<223> OTHER INFORMATION: Synthetic peptide

<400> SEQUENCE: 26

Glu Leu Glu Lys Gly Gly Leu Glu Gly Glu Lys Gly Gly Lys Glu Leu
1               5                   10                  15

Glu Lys

<210> SEQ ID NO 27
<211> LENGTH: 26
<212> TYPE: PRT
<213> ORGANISM: Artificial sequence
<220> FEATURE:
<223> OTHER INFORMATION: Synthetic peptide

<400> SEQUENCE: 27

Lys Trp Lys Ser Phe Leu Lys Thr Lys Lys Ser Ala Val Lys Thr Val
1               5                   10                  15

Leu His Thr Ala Leu Lys Ala Ile Ser Ser
            20                  25

<210> SEQ ID NO 28
<211> LENGTH: 26
<212> TYPE: PRT
<213> ORGANISM: Artificial sequence
<220> FEATURE:
<223> OTHER INFORMATION: Synthetic peptide

<400> SEQUENCE: 28

Lys Trp Lys Ser Lys Leu Lys Thr Phe Lys Ser Ala Val Lys Thr Val
1               5                   10                  15

Leu His Thr Ala Leu Lys Ala Ile Ser Ser
            20                  25

<210> SEQ ID NO 29
<211> LENGTH: 26
<212> TYPE: PRT
```

```
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: A at position 9 is D-Ala.

<400> SEQUENCE: 29

Lys Trp Lys Ser Phe Leu Lys Thr Ala Lys Ser Ala Val Lys Thr Val
1               5                   10                  15

Leu His Thr Ala Leu Lys Ala Ile Ser Ser
            20                  25

<210> SEQ ID NO 30
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: A at position 5 is D-Ala.

<400> SEQUENCE: 30

Lys Trp Lys Ser Ala Leu Lys Thr Phe Lys Ser Ala Val Lys Thr Val
1               5                   10                  15

Leu His Thr Ala Leu Lys Ala Ile Ser Ser
            20                  25

<210> SEQ ID NO 31
<211> LENGTH: 26
<212> TYPE: PRT
<213> ORGANISM: Artificial sequence
<220> FEATURE:
<223> OTHER INFORMATION: Synthetic peptide

<400> SEQUENCE: 31

Lys Trp Lys Ser Phe Leu Lys Thr Phe Lys Ser Ala Arg Lys Thr Val
1               5                   10                  15

Leu His Thr Ala Leu Lys Ala Ile Ser Ser
            20                  25

<210> SEQ ID NO 32
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(26)
<223> OTHER INFORMATION: A at positions 6 and 21 is D-Ala.

<400> SEQUENCE: 32

Lys Trp Lys Ser Phe Ala Lys Thr Phe Lys Ser Ala Val Lys Thr Val
1               5                   10                  15

Leu His Thr Ala Ala Lys Ala Ile Ser Ser
            20                  25

<210> SEQ ID NO 33
<211> LENGTH: 26
<212> TYPE: PRT
<213> ORGANISM: Artificial sequence
<220> FEATURE:
<223> OTHER INFORMATION: Synthetic peptide
```

```
<400> SEQUENCE: 33

Lys Trp Lys Ser Phe Lys Thr Phe Lys Ser Ala Val Lys Thr Val
1               5                   10                  15

Leu His Thr Ala Lys Lys Ala Ile Ser Ser
            20                  25

<210> SEQ ID NO 34
<211> LENGTH: 25
<212> TYPE: PRT
<213> ORGANISM: Artificial sequence
<220> FEATURE:
<223> OTHER INFORMATION: Synthetic peptide

<400> SEQUENCE: 34

Trp Lys Ser Phe Leu Lys Thr Phe Lys Ser Ala Val Lys Thr Val Leu
1               5                   10                  15

His Thr Ala Leu Lys Ala Ile Ser Ser
            20                  25

<210> SEQ ID NO 35
<211> LENGTH: 24
<212> TYPE: PRT
<213> ORGANISM: Artificial sequence
<220> FEATURE:
<223> OTHER INFORMATION: Synthetic peptide

<400> SEQUENCE: 35

Lys Ser Phe Leu Lys Thr Phe Lys Ser Ala Val Lys Thr Val Leu His
1               5                   10                  15

Thr Ala Leu Lys Ala Ile Ser Ser
            20

<210> SEQ ID NO 36
<211> LENGTH: 24
<212> TYPE: PRT
<213> ORGANISM: Artificial sequence
<220> FEATURE:
<223> OTHER INFORMATION: Synthetic peptide

<400> SEQUENCE: 36

Lys Trp Lys Ser Phe Leu Lys Thr Phe Lys Ser Ala Val Lys Thr Val
1               5                   10                  15

Leu His Thr Ala Leu Lys Ala Ile
            20

<210> SEQ ID NO 37
<211> LENGTH: 23
<212> TYPE: PRT
<213> ORGANISM: Artificial sequence
<220> FEATURE:
<223> OTHER INFORMATION: Synthetic peptide

<400> SEQUENCE: 37

Lys Trp Lys Ser Phe Leu Lys Thr Phe Lys Ser Ala Val Lys Thr Val
1               5                   10                  15

Leu His Thr Ala Leu Lys Ala
            20

<210> SEQ ID NO 38
<211> LENGTH: 26
<212> TYPE: PRT
<213> ORGANISM: Artificial sequence
<220> FEATURE:
```

```
<223> OTHER INFORMATION: Synthetic peptide

<400> SEQUENCE: 38

Lys Ile Lys Ser Ala Leu Lys Thr Leu Lys Ser Phe Lys Thr Ala
1               5                   10                  15

Ala His Thr Leu Phe Lys Val Trp Ser Ser
            20                  25

<210> SEQ ID NO 39
<211> LENGTH: 26
<212> TYPE: PRT
<213> ORGANISM: Artificial sequence
<220> FEATURE:
<223> OTHER INFORMATION: Synthetic peptide

<400> SEQUENCE: 39

Ser Trp Ser Lys Phe Leu Lys Lys Phe Thr Lys Ala Lys Ser His Val
1               5                   10                  15

Leu Thr Thr Ala Leu Ser Ala Ile Lys Lys
            20                  25

<210> SEQ ID NO 40
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(13)
<220> FEATURE:
<221> NAME/KEY: MISC_FEATURE
<222> LOCATION: (11)..(13)
<223> OTHER INFORMATION: X at positions 11 and 13 is Gly, L- or D-Leu,
      Val, Ser, Ala, Lys.

<400> SEQUENCE: 40

Lys Trp Lys Ser Phe Leu Lys Thr Phe Lys Xaa Ala Xaa Lys Thr Val
1               5                   10                  15

Leu His Thr Ala Leu Lys Ala Ile Ser Ser
            20                  25

<210> SEQ ID NO 41
<211> LENGTH: 26
<212> TYPE: PRT
<213> ORGANISM: Artificial sequence
<220> FEATURE:
<223> OTHER INFORMATION: Synthetic peptide

<400> SEQUENCE: 41

Lys His Ala Val Ile Lys Trp Ser Ile Lys Ser Ser Val Lys Phe Lys
1               5                   10                  15

Ile Ser Thr Ala Phe Lys Ala Thr Thr Ile
            20                  25

<210> SEQ ID NO 42
<211> LENGTH: 26
<212> TYPE: PRT
<213> ORGANISM: Artificial sequence
<220> FEATURE:
<223> OTHER INFORMATION: Synthetic peptide

<400> SEQUENCE: 42

His Trp Ser Lys Leu Leu Lys Ser Phe Thr Lys Ala Leu Lys Lys Phe
1               5                   10                  15
```

```
Ala Lys Ala Ile Thr Ser Val Val Ser Thr
            20                  25

<210> SEQ ID NO 43
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is any amino acid in L- or
      D-conformation.

<400> SEQUENCE: 43

Lys Trp Lys Ser Phe Leu Lys Thr Phe Lys Xaa Ala Val Lys Thr Val
1               5                   10                  15

Leu His Thr Ala Leu Lys Ala Ile Ser Ser
            20                  25

<210> SEQ ID NO 44
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: X at position 13 is any amino acid in L- or
      D-conformation.

<400> SEQUENCE: 44

Lys Trp Lys Ser Phe Leu Lys Thr Phe Lys Ser Ala Xaa Lys Thr Val
1               5                   10                  15

Leu His Thr Ala Leu Lys Ala Ile Ser Ser
            20                  25

<210> SEQ ID NO 45
<211> LENGTH: 26
<212> TYPE: PRT
<213> ORGANISM: Artificial sequence
<220> FEATURE:
<223> OTHER INFORMATION: Synthetic peptide

<400> SEQUENCE: 45

Lys Trp Lys Ser Phe Leu Lys Thr Phe Lys Ser Ala Lys Lys Thr Val
1               5                   10                  15

Leu His Thr Ala Leu Lys Leu Ile Ser Ser
            20                  25

<210> SEQ ID NO 46
<211> LENGTH: 26
<212> TYPE: PRT
<213> ORGANISM: Artificial sequence
<220> FEATURE:
<223> OTHER INFORMATION: Synthetic peptide

<400> SEQUENCE: 46

Lys Trp Lys Ser Phe Leu Lys Thr Phe Lys Ser Leu Lys Lys Thr Val
1               5                   10                  15

Leu His Thr Ala Leu Lys Ala Ile Ser Ser
            20                  25

<210> SEQ ID NO 47
```

```
<211> LENGTH: 26
<212> TYPE: PRT
<213> ORGANISM: Artificial sequence
<220> FEATURE:
<223> OTHER INFORMATION: Synthetic peptide

<400> SEQUENCE: 47

Lys Trp Lys Ser Phe Leu Lys Thr Phe Lys Ser Ala Lys Lys Thr Val
1               5                   10                  15

Leu His Thr Leu Leu Lys Ala Ile Ser Ser
            20                  25

<210> SEQ ID NO 48
<211> LENGTH: 26
<212> TYPE: PRT
<213> ORGANISM: Artificial sequence
<220> FEATURE:
<223> OTHER INFORMATION: Synthetic peptide

<400> SEQUENCE: 48

Lys Trp Lys Ser Phe Leu Lys Thr Phe Lys Ser Leu Lys Lys Thr Val
1               5                   10                  15

Leu His Thr Ala Leu Lys Leu Ile Ser Ser
            20                  25

<210> SEQ ID NO 49
<211> LENGTH: 26
<212> TYPE: PRT
<213> ORGANISM: Artificial sequence
<220> FEATURE:
<223> OTHER INFORMATION: Synthetic peptide

<400> SEQUENCE: 49

Lys Trp Lys Ser Phe Leu Lys Thr Phe Lys Ser Leu Lys Lys Thr Val
1               5                   10                  15

Leu His Thr Leu Leu Lys Ala Ile Ser Ser
            20                  25

<210> SEQ ID NO 50
<211> LENGTH: 26
<212> TYPE: PRT
<213> ORGANISM: Artificial sequence
<220> FEATURE:
<223> OTHER INFORMATION: Synthetic construct: peptide

<400> SEQUENCE: 50

Lys Trp Lys Ser Phe Leu Lys Thr Phe Lys Ser Leu Lys Lys Thr Val
1               5                   10                  15

Leu His Thr Leu Leu Lys Leu Ile Ser Ser
            20                  25

<210> SEQ ID NO 51
<211> LENGTH: 22
<212> TYPE: PRT
<213> ORGANISM: Artificial sequence
<220> FEATURE:
<223> OTHER INFORMATION: Synthetic construct: peptide

<400> SEQUENCE: 51

Lys Ser Phe Leu Lys Thr Phe Lys Ser Ala Lys Leu Lys Thr Val Leu
1               5                   10                  15

His Thr Ala Leu Lys Ala
            20
```

-continued

```
<210> SEQ ID NO 52
<211> LENGTH: 22
<212> TYPE: PRT
<213> ORGANISM: Artificial sequence
<220> FEATURE:
<223> OTHER INFORMATION: Synthetic construct: peptide
<220> FEATURE:
<221> NAME/KEY: MISC_FEATURE
<222> LOCATION: (11)..(11)
<223> OTHER INFORMATION: K at position 11 is D-lysine.

<400> SEQUENCE: 52

Lys Ser Phe Leu Lys Thr Phe Lys Ser Ala Lys Leu Lys Thr Val Leu
1               5                   10                  15

His Thr Ala Leu Lys Ala
            20

<210> SEQ ID NO 53
<211> LENGTH: 26
<212> TYPE: PRT
<213> ORGANISM: Artificial Sequence
<220> FEATURE:
<223> OTHER INFORMATION: Synthetic construct: antimicrobial peptide D2

<400> SEQUENCE: 53

Lys Trp Lys Ser Phe Leu Lys Thr Phe Lys Ser Ala Lys Lys Thr Val
1               5                   10                  15

Leu His Thr Leu Leu Lys Ala Ile Ser Ser
            20                  25

<210> SEQ ID NO 54
<211> LENGTH: 26
<212> TYPE: PRT
<213> ORGANISM: Artificial Sequence
<220> FEATURE:
<223> OTHER INFORMATION: Synthetic construct: antimicrobial peptide D3

<400> SEQUENCE: 54

Lys Trp Lys Ser Phe Leu Lys Thr Phe Lys Ser Leu Lys Lys Thr Val
1               5                   10                  15

Leu His Thr Leu Leu Lys Ala Ile Ser Ser
            20                  25

<210> SEQ ID NO 55
<211> LENGTH: 26
<212> TYPE: PRT
<213> ORGANISM: Artificial Sequence
<220> FEATURE:
<223> OTHER INFORMATION: Synthetic construct: antimicrobial peptide D4

<400> SEQUENCE: 55

Lys Trp Lys Ser Phe Leu Lys Thr Phe Lys Ser Leu Lys Lys Thr Val
1               5                   10                  15

Leu His Thr Leu Leu Lys Leu Ile Ser Ser
            20                  25

<210> SEQ ID NO 56
<211> LENGTH: 26
<212> TYPE: PRT
<213> ORGANISM: Artificial Sequence
<220> FEATURE:
<223> OTHER INFORMATION: Synthetic construct: antimicrobial peptide D5

<400> SEQUENCE: 56

Lys Trp Lys Ser Phe Leu Lys Thr Phe Lys Ser Leu Lys Lys Thr Lys
1               5                   10                  15
```

```
Leu His Thr Leu Leu Lys Leu Ile Ser Ser
            20                  25

<210> SEQ ID NO 57
<211> LENGTH: 26
<212> TYPE: PRT
<213> ORGANISM: Artificial Sequence
<220> FEATURE:
<223> OTHER INFORMATION: Synthetic construct: antimicrobial peptide D6

<400> SEQUENCE: 57

Lys Trp Lys Ser Phe Leu Lys Thr Phe Lys Ser Leu Lys Lys Thr Lys
1               5                   10                  15

Leu His Thr Leu Leu Lys Val Ile Ser Ser
            20                  25

<210> SEQ ID NO 58
<211> LENGTH: 26
<212> TYPE: PRT
<213> ORGANISM: Artificial Sequence
<220> FEATURE:
<223> OTHER INFORMATION: Synthetic construct: antimicrobial peptide D7

<400> SEQUENCE: 58

Lys Trp Lys Ser Phe Leu Lys Thr Phe Lys Ser Val Lys Lys Thr Lys
1               5                   10                  15

Leu His Thr Leu Leu Lys Leu Ile Ser Ser
            20                  25

<210> SEQ ID NO 59
<211> LENGTH: 26
<212> TYPE: PRT
<213> ORGANISM: Artificial Sequence
<220> FEATURE:
<223> OTHER INFORMATION: Synthetic construct: antimicrobial peptide D8

<400> SEQUENCE: 59

Lys Trp Lys Ser Phe Leu Lys Thr Phe Lys Ser Val Lys Lys Thr Lys
1               5                   10                  15

Leu His Thr Leu Leu Lys Val Ile Ser Ser
            20                  25

<210> SEQ ID NO 60
<211> LENGTH: 26
<212> TYPE: PRT
<213> ORGANISM: Artificial Sequence
<220> FEATURE:
<223> OTHER INFORMATION: Synthetic construct: antimicrobial peptide D9

<400> SEQUENCE: 60

Lys Trp Lys Ser Phe Leu Lys Thr Phe Lys Ser Leu Lys Lys Thr Lys
1               5                   10                  15

Leu His Thr Leu Leu Lys Ala Ile Ser Ser
            20                  25

<210> SEQ ID NO 61
<211> LENGTH: 26
<212> TYPE: PRT
<213> ORGANISM: Artificial Sequence
<220> FEATURE:
<223> OTHER INFORMATION: Synthetic construct: antimicrobial peptide D10

<400> SEQUENCE: 61

Lys Trp Lys Ser Phe Leu Lys Thr Phe Lys Ser Ala Lys Lys Thr Lys
```

```
1               5                  10                 15

Leu His Thr Leu Leu Lys Leu Ile Ser Ser
            20                 25

<210> SEQ ID NO 62
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(26)
<223> OTHER INFORMATION: At positions 12, 20 and 23 Xaa is Leucine,
      Valine or Alanine and A; and at positions 13 and 16, Xaa can be
      Lysine, Arginine, Histidine, Ornithine, diaminobutyric acid or
      diaminopropionic acid.

<400> SEQUENCE: 62

Lys Trp Lys Ser Phe Leu Lys Thr Phe Lys Ser Xaa Xaa Lys Thr Xaa
1               5                  10                 15

Leu His Thr Xaa Leu Lys Xaa Ile Ser Ser
            20                 25

<210> SEQ ID NO 63
<211> LENGTH: 26
<212> TYPE: PRT
<213> ORGANISM: Artificial Sequence
<220> FEATURE:
<223> OTHER INFORMATION: Synthetic peptide: D11

<400> SEQUENCE: 63

Lys Trp Lys Ser Phe Leu Lys Thr Phe Ser Lys Ala Lys Lys Lys Val
1               5                  10                 15

Leu Lys Thr Ala Leu Lys Ala Ile Ser Lys
            20                 25

<210> SEQ ID NO 64
<211> LENGTH: 26
<212> TYPE: PRT
<213> ORGANISM: Artificial Sequence
<220> FEATURE:
<223> OTHER INFORMATION: Synthetic peptide: D12

<400> SEQUENCE: 64

Lys Trp Lys Ser Phe Leu Lys Thr Phe Ser Lys Leu Lys Lys Lys Lys
1               5                  10                 15

Leu Lys Thr Leu Leu Lys Leu Ile Ser Lys
            20                 25

<210> SEQ ID NO 65
<211> LENGTH: 26
<212> TYPE: PRT
<213> ORGANISM: Artificial Sequence
<220> FEATURE:
<223> OTHER INFORMATION: Synthetic peptide: D13

<400> SEQUENCE: 65

Lys Trp Lys Ser Phe Leu Lys Thr Phe Ser Lys Leu Lys Lys Lys Lys
1               5                  10                 15

Leu Lys Thr Leu Leu Lys Ala Ile Ser Lys
            20                 25

<210> SEQ ID NO 66
<211> LENGTH: 26
```

<212> TYPE: PRT
<213> ORGANISM: Artificial Sequence
<220> FEATURE:
<223> OTHER INFORMATION: Synthetic peptide: D14

<400> SEQUENCE: 66

Lys Trp Lys Ser Phe Leu Lys Thr Phe Ser Ala Lys Lys Lys
1               5                   10                  15

Leu Lys Thr Leu Leu Lys Ala Ile Ser Lys
            20                  25

<210> SEQ ID NO 67
<211> LENGTH: 26
<212> TYPE: PRT
<213> ORGANISM: Artificial Sequence
<220> FEATURE:
<223> OTHER INFORMATION: Synthetic peptide: D15

<400> SEQUENCE: 67

Lys Leu Lys Ser Leu Leu Lys Thr Leu Ser Lys Ala Lys Lys Leu
1               5                   10                  15

Leu Lys Thr Ala Leu Lys Ala Leu Ser Lys
            20                  25

<210> SEQ ID NO 68
<211> LENGTH: 26
<212> TYPE: PRT
<213> ORGANISM: Artificial Sequence
<220> FEATURE:
<223> OTHER INFORMATION: Synthetic peptide: D16

<400> SEQUENCE: 68

Lys Leu Lys Ser Leu Leu Lys Thr Leu Ser Lys Ala Lys Lys Lys
1               5                   10                  15

Leu Lys Thr Leu Leu Lys Ala Leu Ser Lys
            20                  25

<210> SEQ ID NO 69
<211> LENGTH: 26
<212> TYPE: PRT
<213> ORGANISM: Artificial Sequence
<220> FEATURE:
<223> OTHER INFORMATION: Synthetic peptide: D17

<400> SEQUENCE: 69

Ser Trp Ser Ser Phe Leu Ser Thr Phe Ser Ala Lys Lys Lys Ala
1               5                   10                  15

Leu Lys Thr Leu Leu Ser Ala Ile Ser Ser
            20                  25

<210> SEQ ID NO 70
<211> LENGTH: 26
<212> TYPE: PRT
<213> ORGANISM: Artificial Sequence
<220> FEATURE:
<223> OTHER INFORMATION: Synthetic peptide: D18

<400> SEQUENCE: 70

Ser Trp Ser Ser Phe Leu Lys Thr Phe Ser Ala Lys Lys Lys Ala
1               5                   10                  15

Leu Lys Thr Leu Leu Ser Ala Ile Ser Ser
            20                  25

<210> SEQ ID NO 71

```
<211> LENGTH: 26
<212> TYPE: PRT
<213> ORGANISM: Artificial Sequence
<220> FEATURE:
<223> OTHER INFORMATION: Synthetic peptide: D19

<400> SEQUENCE: 71

Ser Trp Ser Ser Phe Leu Lys Thr Phe Ser Lys Ala Lys Lys Lys Ala
1               5                   10                  15

Leu Lys Thr Leu Leu Lys Ala Ile Ser Ser
            20                  25

<210> SEQ ID NO 72
<211> LENGTH: 26
<212> TYPE: PRT
<213> ORGANISM: Artificial Sequence
<220> FEATURE:
<223> OTHER INFORMATION: Synthetic peptide: D20

<400> SEQUENCE: 72

Ser Trp Lys Ser Phe Leu Lys Thr Phe Ser Lys Ala Lys Lys Lys Ala
1               5                   10                  15

Leu Lys Thr Leu Leu Lys Ala Ile Ser Ser
            20                  25

<210> SEQ ID NO 73
<211> LENGTH: 26
<212> TYPE: PRT
<213> ORGANISM: Artificial Sequence
<220> FEATURE:
<223> OTHER INFORMATION: Synthetic peptide: D21

<400> SEQUENCE: 73

Ser Trp Lys Ser Phe Leu Lys Thr Phe Ser Lys Ala Lys Lys Lys Ala
1               5                   10                  15

Leu Lys Thr Leu Leu Lys Ala Ile Ser Lys
            20                  25

<210> SEQ ID NO 74
<211> LENGTH: 26
<212> TYPE: PRT
<213> ORGANISM: Artificial Sequence
<220> FEATURE:
<223> OTHER INFORMATION: Synthetic peptide: D22

<400> SEQUENCE: 74

Lys Trp Lys Ser Phe Leu Lys Thr Phe Ser Lys Ala Lys Lys Lys Ala
1               5                   10                  15

Leu Lys Thr Leu Leu Lys Ala Ile Ser Lys
            20                  25

<210> SEQ ID NO 75
<211> LENGTH: 26
<212> TYPE: PRT
<213> ORGANISM: Artificial Sequence
<220> FEATURE:
<223> OTHER INFORMATION: Synthetic peptide: D23

<400> SEQUENCE: 75

Lys Leu Lys Ser Leu Leu Lys Thr Leu Ser Lys Leu Lys Lys Lys Lys
1               5                   10                  15

Leu Lys Thr Leu Leu Lys Ala Leu Ser Lys
            20                  25
```

```
<210> SEQ ID NO 76
<211> LENGTH: 26
<212> TYPE: PRT
<213> ORGANISM: Artificial Sequence
<220> FEATURE:
<223> OTHER INFORMATION: Synthetic peptide: D24

<400> SEQUENCE: 76

Lys Leu Lys Ser Leu Leu Lys Thr Leu Ser Lys Leu Lys Lys Lys Lys
1               5                   10                  15

Leu Lys Thr Leu Leu Lys Leu Leu Ser Lys
            20                  25

<210> SEQ ID NO 77
<211> LENGTH: 26
<212> TYPE: PRT
<213> ORGANISM: Artificial Sequence
<220> FEATURE:
<223> OTHER INFORMATION: Synthetic construct: consensus sequence for
      antimicrobial peptide
<220> FEATURE:
<221> NAME/KEY: MISC_FEATURE
<222> LOCATION: (2)..(2)
<223> OTHER INFORMATION: X is a large hydrophobic amino acid, W or L
<220> FEATURE:
<221> NAME/KEY: MISC_FEATURE
<222> LOCATION: (5)..(9)
<223> OTHER INFORMATION: X is a large hydrophobic amino acid, F, L or I
<220> FEATURE:
<221> NAME/KEY: MISC_FEATURE
<222> LOCATION: (12)..(24)
<223> OTHER INFORMATION: At positions 12, 20, 23 and 24, X is a A or L
      or I or V
<220> FEATURE:
<221> NAME/KEY: MISC_FEATURE
<222> LOCATION: (16)..(16)
<223> OTHER INFORMATION: X is a K or  L

<400> SEQUENCE: 77

Lys Xaa Lys Ser Xaa Leu Lys Thr Xaa Ser Lys Xaa Lys Lys Lys Xaa
1               5                   10                  15

Leu Lys Thr Xaa Leu Lys Xaa Xaa Ser Lys
            20                  25

<210> SEQ ID NO 78
<211> LENGTH: 26
<212> TYPE: PRT
<213> ORGANISM: Artificial Sequence
<220> FEATURE:
<223> OTHER INFORMATION: Synthetic peptide: alternate consensus sequence
      of antimicrobial peptide
<220> FEATURE:
<221> NAME/KEY: MISC_FEATURE
<222> LOCATION: (1)..(26)
<223> OTHER INFORMATION: At positions 1, 3, 7, 22, and 26, X is K or S
<220> FEATURE:
<221> NAME/KEY: MISC_FEATURE
<222> LOCATION: (1)..(26)
<223> OTHER INFORMATION: At positions 12 and 23, X is or L or A
<220> FEATURE:
<221> NAME/KEY: MISC_FEATURE
<222> LOCATION: (16)..(16)
<223> OTHER INFORMATION: X is A, V, I, L or K
<220> FEATURE:
<221> NAME/KEY: MISC_FEATURE
<222> LOCATION: (24)..(24)
<223> OTHER INFORMATION: X is I or L or A or V
```

-continued

```
<400> SEQUENCE: 78

Xaa Trp Xaa Ser Phe Leu Xaa Thr Phe Ser Lys Xaa Lys Lys Lys Xaa
1               5                   10                  15

Leu Lys Thr Leu Leu Xaa Xaa Xaa Ser Xaa
            20                  25
```

ANTIMICROBIAL PEPTIDES

CROSS-REFERENCE TO RELATED APPLICATIONS

This application claims benefit of U.S. Provisional Application 61/217,915, filed Jun. 5, 2009, which application is incorporated by reference herein to the extent there is no inconsistency with the present disclosure.

STATEMENT ON FEDERALLY SPONSORED RESEARCH OR DEVELOPMENT

This invention was made with government support under grant number R01 AI067296 awarded by The National Institutes of Health. The government has certain rights in the invention.

THE SEQUENCE LISTING

This application contains a Sequence Listing submitted as an electronic text file entitled "Sequence Listing_CU2374H-US1" having a size in bytes of 29 kb, and created Oct. 2, 2015. The information contained in this electronic file is hereby incorporated by reference in its entirety pursuant to 37 CFR §1.52(e)(5).

BACKGROUND OF THE INVENTION

The present invention relates to novel antimicrobial peptides and methods of making and using such peptides to inhibit microbial growth and in pharmaceutical compositions for treatment or prevention of infections caused by a broad range of microorganisms including gram-positive and gram-negative bacteria, especially *Pseudomonas aeruginosa* and *Acinetobacter baumannii*.

The extensive clinical use of classical antibiotics has led to the growing emergence of many medically relevant resistant strains of bacteria (1,2). Moreover, only three new structural classes of antibiotics (the oxazolidinone, linezolid, the streptogramins and the lipopeptide-daptomycin) have been introduced into medical practice in the past 40 years. Therefore, the development of a new class of antibiotics has great significance. The cationic antimicrobial peptides could represent such a new class of antibiotics (3-5). Although the exact mode of action of the cationic antimicrobial peptides has not been established, all cationic amphipathic peptides interact with membranes and it has been proposed that the cytoplasmic membrane is the main target of some peptides, where peptide accumulation in the membrane may cause increased permeability and loss of barrier function (6,7). Therefore, the development of resistance to these membrane active peptides is less likely because this would require substantial changes in the lipid composition of cell membranes of microorganisms.

Two major classes of the cationic antimicrobial peptides are the α-helical and the β-sheet peptides (3,4,8,9). The β-sheet class includes cyclic peptides constrained in this conformation either by intramolecular disulfide bonds, e.g., defensins (10) and protegrins (11), or by an N-terminal to C-terminal covalent bond, e.g., gramicidin S (12) and tyrocidines (13). Unlike the β-sheet peptides, α-helical peptides are more linear molecules that mainly exist as disordered structures in aqueous media and become amphipathic helices upon interaction with the hydrophobic membranes, e.g., cecropins (14), magainins (15) and melittins (16).

The major barrier to the use of antimicrobial peptides as antibiotics is their toxicity or ability to lyse eukaryotic cells, at least in some instances. This is perhaps not a surprising result if the target is indeed the cell membrane (3-6). To be useful as a broad-spectrum antibiotic, it is necessary to dissociate deleterious effects on mammalian cells from antimicrobial activity, i.e., to increase the antimicrobial activity and reduce toxicity to normal cells.

A synthetic peptide approach to examining the effect of changes, including small or incremental changes in hydrophobicity/hydrophilicity, amphipathicity and helicity of cationic antimicrobial peptides can facilitate rapid progress in rational design of peptide antibiotics. Generally, L-amino acids are the isomers found throughout natural peptides and proteins; D-amino acids are the isomeric forms rarely seen in natural peptides/proteins, except in some bacterial cell walls. In certain circumstances, the helix-destabilizing properties of D-amino acids offer a potential systematic approach to the controlled alteration of the hydrophobicity, amphipathicity, and helicity of amphipathic α-helical model peptides (26).

A particular structural framework of an amphipathic α-helical antimicrobial peptide, $V_{681}$ (28) and its related peptide D1, has been used to change peptide amphipathicity, hydrophobicity, net charge and helicity by single D- or L-amino acid substitutions in the center of either the polar or nonpolar faces of the amphipathic helix so that the effects on antimicrobial activity and host toxicity can be determined. Portions of this work have been described in International Patent Publication WO 2006/065977 and U.S. Ser. No. 61/195,299, which are incorporated by reference herein. See also references 53, 92-94.

By introducing different D- or L-amino acid substitutions, it was shown that hydrophobicity, amphiphilicity and helicity have dramatic effects on the biophysical and biological activities and, thus that significant improvements in antimicrobial activity and specificity can be achieved. High peptide hydrophobicity and amphipathicity can result in greater peptide self-association in solution. Temperature profiling in reversed-phase chromatography has proven useful for measuring self-association of small amphipathic molecules (29, 30). This technique has been applied to the investigation of the influence of peptide dimerization ability on biological activities of α-helical antimicrobial peptides.

Widespread bacterial resistance to all commercially available antibiotic classes and their respective mechanisms of action is well documented (102). Recent reports reveal that the incidence of resistant gram-positive and gram-negative bacteria isolates generated in hospital patients exceeds 25% in several EU Member States (103). Bacterial resistance to antibiotics is having a dramatic impact on the global healthcare system. For example, 37,000 patients die in the EU annually from a multidrug-resistant hospital-acquired infection, resulting in healthcare costs of at least EUR 1.5 billion ($2.3B) each year (103), while in the U.S., annual healthcare costs related to the treatment of *P. aeruginosa*, alone, is estimated at $2.7 billion (104). Despite the tremendous expenditures to treat the problem, the CDC estimates that 99,000 deaths occurred in the U.S. in 2007 due to resistant infections within the healthcare system (105).

There is a long felt need in the art for new antibiotics to circumvent the development of resistance to many of the antibiotics currently in use and for new antibiotics with relatively low toxicity for use in human and veterinary medicine, especially for use in treatments for infections with multiply drug resistant and/or difficult to treat microorganisms.

SUMMARY OF THE INVENTION

Provided herein are peptide compounds useful as antimicrobial agents and related methods. In embodiments of the invention, the antimicrobial peptides range in size from about 23 to about 28 or about 23 to about 26 amino acids in length joined by peptide bonds and having a core amino acid sequence of about 21 amino acids. The amino acids in the peptide compounds can be all in the L configuration, all in the D configuration or in a combination of D or L configurations. Furthermore, the peptides can be acylated (e.g., acetylated) at the N-terminus, and they may terminate in an amide at the C-terminus. Exemplary peptides include those of D11-24, comprising the amino acid sequences set forth in SEQ ID NOs:63-76, all of which exhibit broad spectrum antimicrobial activity and are useful in treating infections and inhibiting microbial growth. Advantageously, therapeutic peptides are D11 (SEQ ID NO:63), D14 (SEQ ID NO:66), D15 (SEQ ID NO:67) or D16 (SEQ ID NO:68).

The peptides disclosed herein have potent antimicrobial activities and are useful against bacteria, fungi and other pathogens, importantly against *Pseudomonas aeruginosa* and *Acinetobacter baumannii*. These peptides are effective compounds for use in human and/or veterinary medicine, or as agents in agricultural, food science, or industrial applications. Peptides of the present invention are also useful for inhibiting the growth of *Pseudomonas aeruginosa, Acinetobacter baumannii* or *Staphylococcus aureus* or methicillin resistant *Staphylococcus aureus* and for treating infections in humans or animals caused by these and other organisms.

Without wishing to be bound by any particular theory, from structure/activity studies on both natural and synthetic antimicrobial peptides, it is believed that a number of factors are important for antimicrobial activity. These are identified as including the presence of both hydrophobic and basic residues in the peptide, an amphipathic nature that segregates basic and hydrophobic residues to opposite sides of the molecule, and an inducible or preformed secondary structure (α-helical or β-sheet). Also without wishing to be bound by any particular theory, substituting different D-amino acids into the center of the hydrophobic face of an amphipathic α-helical model peptide can vary the net charge of the peptide, hydrophobicity and the toxicity to mammalian cells (for example, as measured by hemolysis) can be reduced, for example, by choice of a specificity determinant on the nonpolar face of the peptide. An advantage of such variation(s) is that it provides an opportunity for greater understanding of the mechanism of action of these peptides as well as optimizing the therapeutic index of the antimicrobial peptides.

For certain α-helical and β-sheet peptides, there have been attempts to delineate features responsible for anti-eukaryotic or toxic activities and for antimicrobial activities. High amphipathicity (17-20), high hydrophobicity (17, 20-22), as well as high helicity or β-sheet structure (20,23,24) may correlate with increased toxicity as measured by hemolytic activity. In contrast, antimicrobial activity may be less dependent on these factors than is hemolytic activity (17-21,23-25). Here, specificity (or therapeutic index (TI) which is defined as the ratio of hemolytic activity and antimicrobial activity) for bacteria over erythrocytes could be increased in one of three ways: increasing antimicrobial activity, decreasing hemolytic activity while maintaining antimicrobial activity, or a combination of both, increasing antimicrobial activity and decreasing hemolytic activity.

Provided herein are methods for treating a patient in need of therapy comprising administering to the patient a peptide of the invention in an amount sufficient to inhibit microbial growth and/or to kill microorganisms. Methods of treating a microbial infection or of reducing the likelihood of contracting a microbial infection are provided herein. The microbial infection can be the result of one or more of a bacterium (especially *P. aeruginosa* or *Acinetobacter baumannii*), or a virus, a fungus, or protozoan, or one or more within a class of those infectious agents, e.g. two different kinds of bacteria, and so on.

In an embodiment, there is a method for increasing antimicrobial activity and/or decreasing toxicity to animal cells, especially human cells, of a peptide compound. In an embodiment, provided herein is a method for decreasing hemolytic activity of a peptide compound while maintaining antimicrobial activity or minimizing a reduction of antimicrobial activity. In an embodiment, the invention provides a method of increasing antimicrobial activity and decreasing hemolytic activity of a peptide compound while maintaining antimicrobial activity or minimizing a reduction of antimicrobial activity; as specifically exemplified this is accomplished by increasing the net positive charge on the peptide by increasing the number of lysine residues on the polar face, especially by increasing positive charge in the center of the nonpolar face of the peptide. See the amino acid sequences of peptides D1 and D17-D22; see Table 3 and SEQ ID NO:24 and 69-74.

The antimicrobial peptides disclosed herein are based, in part, on the recognition that controlled alteration of the net positive charge on the polar face of the helical antimicrobial peptide while maintaining amphipathicity and helicity to yield a peptide with improved therapeutic index. The increase in therapeutic index is achieved via a decrease in toxicity to animal cells as measured by hemolysis, rather than due to a significant affect on antimicrobial activity as measured by MIC. Exemplified herein are peptides derived from the 26-residue peptide sequence, Ac-KWKSFLKTFKS-AVK-TVLHTALKAISS-amide ($V_{681}$, SEQ ID NO: 1), for example, those of D17-D22 (See Table 3; SEQ ID NOs:69-74) or D11-D16 (SEQ ID NOs:63-68) or D23-D24 (see SEQ ID NOs:75-76).

The terms "derived from" or "derivative" are meant to indicate that the inventive peptides are the same or shorter than the $V_{681}$ peptide in size and have one or more amino acid residues substituted, or a combination of both; further variations are also described herein. The peptide compound $V_{681}$ was used as the framework to study the effects of peptide hydrophobicity/hydrophilicity, amphipathicity and helicity on biological activities, for example antimicrobial and hemolytic activities, by substituting one or more amino acid residues at certain locations. These locations can include points at or near the center of the polar and nonpolar faces of the amphipathic helix in addition to other locations. The peptide $V_{681}$ is disclosed in Zhang et al., 1999 (28) and Zhang et al., 2001 (91).

In an embodiment, there are provided compositions and methods relating to a peptide having an amino acid sequences as shown in Table 3, peptides D17-D22, and D23-D24. Other embodiments relate to the antimicrobial peptides D11-D16 and/or D23-24. While the specifically exemplified peptides are comprised entirely of D amino acids, there can be peptides synthesized from L amino acids or combinations of D and L amino acids. Acylation may be at the N-terminus and/or there may be an amide at the C-terminus rather than a carboxyl group. See Table 3 and SEQ ID NOs:63-76).

In a further embodiment, the compositions and methods relate to an antimicrobial peptide conforming to the consensus sequence X1-W-X1-S-F-L-X1-T-F-S-K-X4-K-K-K-X2-L-K-T-L-X1-X4-X3-S-X1 (SEQ ID NO:78), wherein X1 is K or S, X2 is A, V, I, L or K; and X3 is I or L or A or V; X4 is A or L; or D17, D18, D19, D20, D21 and D22, or peptide D11-D16, or D23 or D24 and a peptide of corresponding L amino acids or a peptide in which there is a mixture of L-amino acids and D-amino acids, optionally substituted with an acyl group at the N-terminus and/or having an amide at the C-terminus in place of a carboxyl group.

In yet another embodiment, the compositions and peptides related to an antimicrobial peptide conforming to the consensus sequence K-Xa-K-S-Xb-L-K-T-Xb-S-K-Xd-K-K-K-Xc-L-K-T-Xd-L-K-Xd-Xd-S-K (SEQ ID NO:77), wherein Xa is a large hydrophobic amino acid, for example W or L, Xb is a large hydrophobic amino acid, (F, L, I or V, especially L or F), Xc is K or L or V or A, and Xd is a hydrophobic amino acid (A, L, I or V, especially A or L). Specific examples include D11, D14, D15 and D16, which have significantly improved therapeutic indices as compared to certain other antimicrobial peptides tested, especially as compared to peptide D1.

TABLE 1

Summary of partial sequence listing information.

| SEQ ID NO: | Peptide Name | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|---|
| | Enantiomer* | L | L | L | L | L | L | L | L | L | L | L | L | L | L | L | L | L | L | L | L | L | L | L | L | L | L |
| 1 | V681 | K | W | K | S | F | L | K | T | F | K | S | A | V | K | T | V | L | H | T | A | L | K | A | I | S | S |
| 2 | NL$_L$ | K | W | K | S | F | L | K | T | F | K | S | A | L | L | K | T | V | L | H | T | A | L | K | A | I | S | S |
| 3 | NV$_L$ | K | W | K | S | F | L | K | T | F | K | S | A | V | L | K | T | V | L | H | T | A | L | K | A | I | S | S |
| 4 | NA$_L$ | K | W | K | S | F | L | K | T | F | K | S | A | A | L | K | T | V | L | H | T | A | L | K | A | I | S | S |
| 5 | NS$_L$ | K | W | K | S | F | L | K | T | F | K | S | A | S | L | K | T | V | L | H | T | A | L | K | A | I | S | S |
| 6 | NK$_L$ | K | W | K | S | F | L | K | T | F | K | S | A | K | L | K | T | V | L | H | T | A | L | K | A | I | S | S |
| 7 | NL$_D$ | K | W | K | S | F | L | K | T | F | K | S | A | L | D | K | T | V | L | H | T | A | L | K | A | I | S | S |
| 8 | NV$_D$ | K | W | K | S | F | L | K | T | F | K | S | A | V | D | K | T | V | L | H | T | A | L | K | A | I | S | S |
| 9 | NA$_D$ | K | W | K | S | F | L | K | T | F | K | S | A | A | D | K | T | V | L | H | T | A | L | K | A | I | S | S |
| 10 | NS$_D$ | K | W | K | S | F | L | K | T | F | K | S | A | S | D | K | T | V | L | H | T | A | L | K | A | I | S | S |
| 11 | NK$_D$ | K | W | K | S | F | L | K | T | F | K | S | A | K | D | K | T | V | L | H | T | A | L | K | A | I | S | S |
| 12 | NG | K | W | K | S | F | L | K | T | F | K | S | A | G | K | T | V | L | H | T | A | L | K | A | I | S | S |
| 13 | PL$_L$ | K | W | K | S | F | L | K | T | F | K | L | L | A | V | K | T | V | L | H | T | A | L | K | A | I | S | S |
| 14 | PA$_L$ | K | W | K | S | F | L | K | T | F | K | A | L | A | V | K | T | V | L | H | T | A | L | K | A | I | S | S |
| 15 | PS$_L$ | K | W | K | S | F | L | K | T | F | K | S | L | A | V | K | T | V | L | H | T | A | L | K | A | I | S | S |
| 16 | PV$_L$ | K | W | K | S | F | L | K | T | F | K | V | L | A | V | K | T | V | L | H | T | A | L | K | A | I | S | S |
| 17 | PK$_L$ | K | W | K | S | F | L | K | T | F | K | K | L | A | V | K | T | V | L | H | T | A | L | K | A | I | S | S |
| 18 | PL$_D$ | K | W | K | S | F | L | K | T | F | K | L | D | A | V | K | T | V | L | H | T | A | L | K | A | I | S | S |
| 19 | PA$_D$ | K | W | K | S | F | L | K | T | F | K | A | D | A | V | K | T | V | L | H | T | A | L | K | A | I | S | S |
| 20 | PS$_D$ | K | W | K | S | F | L | K | T | F | K | S | D | A | V | K | T | V | L | H | T | A | L | K | A | I | S | S |
| 21 | PV$_D$ | K | W | K | S | F | L | K | T | F | K | V | D | A | V | K | T | V | L | H | T | A | L | K | A | I | S | S |
| 22 | PK$_D$ | K | W | K | S | F | L | K | T | F | K | K | D | A | V | K | T | V | L | H | T | A | L | K | A | I | S | S |
| 23 | PG | K | W | K | S | F | L | K | T | F | K | G | A | V | K | T | V | L | H | T | A | L | K | A | I | S | S |
| | Enantiomer | D | D | D | D | D | D | D | D | D | D | D | D | D | D | D | D | D | D | D | D | D | D | D | D | D | D |
| 24 | D-NK$_D$ | K | W | K | S | F | L | K | T | F | K | S | A | K | K | T | V | L | H | T | A | L | K | A | I | S | S |
| 25 | D-NA$_L$ | K | W | K | S | F | L | K | T | F | K | S | A | A | L | K | T | V | L | H | T | A | L | K | A | I | S | S |
| 1 | D-V681 | K | W | K | S | F | L | K | T | F | K | S | A | V | K | T | V | L | H | T | A | L | K | A | I | S | S |

*L-enantiomer unless otherwise indicated in the Enantiomer column or subscript

TABLE 2

Summary of partial sequence listing information.

| | | | | | | | | | | | | | | | | | | | | | | | | | |
|---|---|---|---|---|---|---|---|---|---|---|---|---|---|---|---|---|---|---|---|---|---|---|---|---|---|
| 31 | V13 to R13 | K | W | K | S | F | L | K | T | F | K | S | A | R | K | T | V | L | H | T | A | L | K | A | I | S |
| 32 | L6-$A_D$6, L21-$A_D$21 | K | W | K | S | F | $A_D$ | K | T | F | K | S | A | V | K | T | V | L | H | T | A | $A_D$ | K | A | I | S |
| 33 | L6-$K_L$6, L21-$K_L$21 | K | W | K | S | F | K | K | T | F | K | S | A | V | K | T | V | L | H | T | A | K | K | A | I | S |
| 34 | Remove K1 | | W | K | S | F | L | K | T | F | K | S | A | K | K | T | V | L | H | T | A | L | K | A | I | S |
| 35 | Remove K1, W2 | | | K | S | F | L | K | T | F | K | S | A | K | K | T | V | L | H | T | A | L | K | A | I | S |
| 36 | Remove S25, S26 | K | W | K | S | F | L | K | T | F | K | S | A | K | K | T | V | L | H | T | A | L | K | A | I | |
| 37 | Remove I24, S25, S26 | K | W | K | S | F | L | K | T | F | K | S | A | K | K | T | V | L | H | T | A | L | K | A | | |
| 38 | non-polar face shuffle | K | I | K | S | $A_D$ | L | K | T | L | K | S | F | K | K | T | A | A | H | T | L | F | K | V | W | S |
| 39 | polar face shuffle | S | W | S | K | F | L | T | K | F | T | K | A | K | S | H | V | L | T | T | A | L | S | A | I | K |

*L-enantiomer unless otherwise indicated.

In an embodiment, the peptide comprises an amino acid sequence as given below, peptides D17-D24. D1 has the sequence shown in Table 1 and SEQ ID NO:24. D5 is Ac-K-W-K-S-F-L-K-T-F-K-S-L-K-K-T-K-L-H-T-L-L-K-L-I-S-S-amide (SEQ ID NO:56); D17 is Ac-S-W-S-S-S-F-L-S-T-F-S-K-A-K-K-K-A-L-K-T-L-L-S-A-I-S-S-amide (SEQ ID NO:69); D18 is Ac-S-W-S-S-F-L-K-T-F-S-K-A-K-K-K-A-L-K-T-L-L-S-A-I-S-S-amide (SEQ ID NO:70); D19 is Ac-S-W-S-S-F-L-K-T-F-S-K-A-K-K-K-A-L-K-T-L-L-K-A-I-S-S-amide (SEQ ID NO:71); D20 is Ac-S-W-K-S-F-L-K-T-F-S-K-A-K-K-K-A-L-K-T-L-L-K-A-I-S-S-amide (SEQ ID NO:72); D21 is Ac-S-W-K-S-F-L-K-T-F-S-K-A-K-K-K-A-L-K-T-L-L-K-A-I-S-K-amide (SEQ ID NO:73), and D22 is Ac-K-W-K-S-F-L-K-T-F-S-K-A-K-K-K-A-L-K-T-L-L-K-A-I-S-K-amide (SEQ ID NO:74). In certain other embodiments there can be conservative amino acid substitutions of hydrophobic amino acids at one or more of positions 2, 5, 6, 9, 12, 16, 17, 20, 21, 23, and 24, especially with leucine as the amino acid which is substituted for the amino acid in peptide D1. In further embodiments the D23 peptide comprises an amino acid sequence as forth in SEQ ID NO:73; D24 comprises the amino acid sequence set forth in (SEQ ID NO:76); see also Table 3 herein.

TABLE 3

Antimicrobial Peptide Sequence Information

| Peptide Name | Substitution[a] | Sequence[b] 1 ··· 13 ··· 26 |
|---|---|---|
| D1 | D-(V13K) (SEQ ID NO: 24) | Ac-K-W-K-S-F-L-K-T-F-K-S-A-K-T-V-L-H-T-A-L-K-A-I-S-S-amide |
| D5 | D-(V13K, V16K, A12L, A20L, A23L) (SEQ ID NO: 56) | |
| D17 | D-(V13K, V16A, A20L, K10S, S11K, T15K, H18K, K1S, K3S, K7S, K22S) (SEQ ID NO: 69) | Ac-S-W-S-S-S-F-L-S-T-F-S-K-A-K-K-K-A-L-K-T-L-L-S-A-I-S-S-amide |
| D18 | D-(V13K, V16A, A20L, K10S, S11K, T15K, H18K, K1S, K3S, K22S) (SEQ ID NO: 70) | Ac-S-W-S-S-F-L-K-T-F-S-K-A-K-K-K-A-L-K-T-L-L-S-A-I-S-S-amide |
| D19 | D-(V13K, V16A, A20L, K10S, S11K, T15K, H18K, K1S, K3S) (SEQ ID NO: 71) | Ac-S-W-S-S-F-L-K-T-F-S-K-A-K-K-K-A-L-K-T-L-L-K-A-I-S-S-amide |
| D20 | D-(V13K, V16A, A20L, K10S, S11K, T15K, H18K, K1S) (SEQ ID NO: 72) | Ac-S-W-K-S-F-L-K-T-F-S-K-A-K-K-K-A-L-K-T-L-L-K-A-I-S-S-amide |
| D21 | D-(V13K, V16A, A20L, S11K, K10S, T15K, H18K, K1S, S26K) (SEQ ID NO: 73) | Ac-S-W-K-S-F-L-K-T-F-S-K-A-K-K-K-A-L-K-T-L-L-K-A-I-S-K-amide |
| D22 | D-(V13K, V16A, A20L, K10S, S11K, T15K, H18K, S26K) (SEQ ID NO: 74) | Ac-K-W-K-S-F-L-K-T-F-S-K-A-K-K-K-A-L-K-T-L-L-K-A-I-S-K-amide |
| D11 | D-(V13K, K10S, S11K, H18K, T15K, S26K) (SEQ ID NO: 63) | Ac-K-W-K-S-F-L-K-T-F-S-K-A-K-K-K-V-L-K-T-A-L-K-A-I-S-K-amide |
| D12 | D-(V13K, V16K, A12L, A20L, A23L, K10S, S11K, H18K, T15K, S26K) (SEQ ID NO: 64) | Ac-K-W-K-S-F-L-K-T-F-S-K-L-K-K-K-K-L-K-T-L-L-K-L-I-S-K-amide |
| D13 | D-(V13K, V16K, A12L, A20L, K10S, S11K, H18K, T15K, S26K) (SEQ ID NO: 65) | Ac-K-W-K-S-F-L-K-T-F-S-K-L-K-K-K-K-L-K-T-L-L-K-A-I-S-K-amide |
| D14 | D-(V13K, V16K, A20L, K10S, S11K, H18K, T15K, S26K) (SEQ ID NO: 66) | Ac-K-W-K-S-F-L-K-T-F-S-K-A-K-K-K-K-L-K-T-L-L-K-A-I-S-K-amide |

TABLE 3-continued

Antimicrobial Peptide Sequence Information

| Peptide Name | Substitution[a] | Sequence[b] 1                13                26 |
|---|---|---|
| D15 | D-(V13K, V10L, K10S, S11K, H18K, T15K, S26K, W2L, F5L, F9L, I24L) (SEQ ID NO: 67) | Ac-K-L-K-S-L-L-K-T-L-S-K-A-K-K-K-L-L-K-T-A-L-K-A-L-S-K-amide |
| D16 | D-(V13K, V16K, A20L, K10S, S11K, H18K, T15K, S26K, W2L, F5L, F9L, I24L) (SEQ ID NO: 68) | Ac-K-L-K-S-L-L-K-T-L-S-K-A-K-K-K-K-L-K-T-L-L-K-A-L-S-K-amide |
| D23 | D-(V13K, V16K, A20L, A12L, K10S, S11K, H18K, T15K, S26K, W2L, F5L, F9L, I24L) (SEQ ID NO: 75) | Ac-K-L-K-S-L-L-K-T-L-S-K-L-K-K-K-K-L-K-T-L-L-K-A-L-S-K-amide |
| D24 | D-(V13K, V16K, A20L, A12L, A23L, K10S, S11K, H18K, T15K, S26K, W2L, F5L, F9L, I24L) (SEQ ID NO: 76) | Ac-K-L-K-S-L-L-K-T-L-S-K-L-K-K-K-K-L-K-T-L-L-K-L-L-S-K-amide |

[a]The D- denotes that all amino acid residues in each peptide are in the D conformation.
[b]Peptide sequences are shown using the one-letter code for amino acid residues;
Ac- denotes Nα-acetyl and -amide denotes C- amide. The specificity determinants K13 and K16 are bolded.

In an embodiment, the molecule (peptide) is helical in a hydrophobic environment. Circular dichroism spectroscopy can be used to monitor α-helical structure in 50% trifluoroethanol, a mimic of the hydrophobic environment of the cytoplasmic membrane. Specifically exemplified sequences are those of D11-D24.

In certain embodiments, successful peptides that are helical analogs with the desired biological activities have very little alpha-helical structure in benign medium (a non-denaturing medium like phosphate buffered saline, e.g., 50 mM $PO_4$ buffer containing 100 mM KCl, pH 7) monitored by circular dichroism spectroscopy. In an embodiment, this structural property can have importance in one or more of several potential mechanisms, for example: a) decreasing dimerization of molecule in benign medium (measured as described herein); b) allowing the peptide to more easily penetrate through the cell wall to reach the membrane of the microbe. Furthermore, disruption of the α-helical structure in benign medium can still allow a positively-charged peptide to be attracted to the negatively-charged cell wall surface of the microbe (e.g. lipopolysaccharide), but the lack of structure can decrease the affinity of peptide for this surface which allows the peptide to more easily pass through the cell wall and enter the interface region of the membrane where the peptide is parallel to the surface of membrane. Here the alpha-helical structure of the peptide can be induced by the hydrophobic environment of the membrane. In this alpha-helical structure, we hypothesize that the non-polar face of the peptide can interact with the hydrophobic portion of the membrane, and its polar and positively-charged groups on the polar face can interact with the negatively-charged groups of the phospholipids on the surface of the membrane.

In an embodiment, a peptide is net positively-charged and amphipathic (amphiphilic) when in an alpha-helical structure. For example, the alpha-helical peptide has a non-polar face or hydrophobic surface on one side of the molecule and a polar and positively-charged surface on the other side of the molecule; i.e., the molecule is amphipathic. Amphipathicity of the molecule can be calculated as described herein.

Certain peptide analogs were studied by temperature profiling in RP-HPLC from 5° C. to 80° C., to evaluate the self-associating ability of the molecules in solution. The ability to self-associate can be another important parameter in understanding peptide antimicrobial and hemolytic activities. It was generally found that a high ability to self-associate in solution, which is due to high hydrophobicity on the non-polar face, was correlated with weak antimicrobial activity and strong hemolytic activity of the peptides. Biological studies showed that strong hemolytic activity of the peptides generally correlated with high hydrophobicity, high amphipathicity and high helicity. In most cases, the D-amino acid substituted peptides possessed an enhanced average antimicrobial activity compared with L-diastereomers. The therapeutic index of $V_{681}$ was improved 90-fold and 23-fold against gram-negative and gram-positive bacteria, respectively (using geometric means comparison of antimicrobial activity). By replacing the central hydrophobic or hydrophilic amino acid residue on the nonpolar or the polar face of these amphipathic molecules with a series of selected D- and L-amino acids, we further demonstrate that this method can be used for the rational design of other antimicrobial peptides with enhanced activities.

TABLE 4

Additional Amino Acid Sequence Information

| Peptide Name | Amino acid sequence (one letter code) |
| --- | --- |
| $NK_L$ | $A_C$-$K_L$-$W_L$-$K_L$-$S_L$-$F_L$-$L_L$-$K_L$-$T_L$-$F_L$-$K_L$-$S_L$-$A_L$-$\boxed{K_L}$-$K_L$-$T_L$-$V_L$-$L_L$-$H_L$-$T_L$-$A_L$-$L_L$-$K_L$-$A_L$-$I_L$-$S_L$-$S_L$-amide (SEQ ID NO: 6) |
| $D$-$NK_D$ | $A_C$-$K_D$-$W_D$-$K_D$-$S_D$-$F_D$-$L_D$-$K_D$-$T_D$-$F_D$-$K_D$-$S_D$-$A_D$-$\boxed{K_D}$-$K_D$-$T_D$-$V_D$-$L_D$-$H_D$-$T_D$-$A_D$-$L_D$-$K_D$-$A_D$-$I_D$-$S_D$-$S_D$-amide (SEQ ID NO: 24) |
| $NA_D$ | $A_C$-$K_L$-$W_L$-$K_L$-$S_L$-$F_L$-$L_L$-$K_L$-$T_L$-$F_L$-$K_L$-$S_L$-$A_L$-$\boxed{A_D}$-$K_L$-$T_L$-$V_L$-$L_L$-$H_L$-$T_L$-$A_L$-$L_L$-$K_L$-$A_L$-$I_L$-$S_L$-$S_L$-amide (SEQ ID NO: 9) |
| $D$-$NA_L$ | $A_C$-$K_D$-$W_D$-$K_D$-$S_D$-$F_D$-$L_D$-$K_D$-$T_D$-$F_D$-$K_D$-$S_D$-$A_D$-$\boxed{A_L}$-$K_D$-$T_D$-$V_D$-$L_D$-$H_D$-$T_D$-$A_D$-$L_D$-$K_D$-$A_D$-$I_D$-$S_D$-$S_D$-amide (SEQ ID NO: 25) |

Herein, a subscript D following an amino acid residue denotes that the residue is a D-amino acid residue; similarly a subscript L denotes an L-amino acid residue. In the peptide name, an initial D- (not subscripted) denotes all D-amino acids in the peptide except where specified (e.g. D-$NA_L$ denotes all D-amino acids with the exception of a single substitution of L-Ala in the center of the non-polar face specified by N). The boxed residues denote the differences at position 13 in the sequence which is in the center of the non-polar face.

In an embodiment, an antimicrobial peptide is integrated in a larger peptide or protein. In an embodiment, a peptide of the invention is covalently or non-covalently associated with another compound, for example, a polymer.

The peptides disclosed have antimicrobial activity against a wide range of microorganisms including gram-positive and gram-negative bacteria. Detailed description of the microorganisms belonging to gram-positive and gram-negative bacteria can be found in Medical Microbiology (1991), $3^{rd}$ edition, edited by Samuel Baron, Churchill Livingstone, New York. Examples of potentially susceptible bacteria include, but are not limited to, *Escherichia coli, Salmonella typhimurium, Pseudomonas aeruginosa, Staphylococcus aureus, Staphylococcus epidermidis, Bacillus subtilis, Acinetobacter baumannii, Enterococcus faecalis, Corynebacterium xerosis,* and *Bacillus anthracis*. The antimicrobial activities of the D11-16, D17-22 and D23-24 peptides have been demonstrated herein against *Pseudomonas aeruginosa, Acinetobacter baumannii* and other bacteria. It is understood that additional gram-positive and gram-negative bacteria are sensitive, and it is further appreciated that the in vitro tests described herein model the effects of the present antimicrobial peptides in topical, local, respiratory or systemic use in a human or animal.

The antimicrobial peptides of the invention are useful as bactericides and/or bacteriostats for modification of infectivity, killing microorganisms, or inhibiting microbial growth or function and thus useful for the treatment of an infection or contamination caused by such microorganisms.

Also provided are therapeutic or otherwise active compositions suitable for human, veterinary, agricultural or pharmaceutical use, comprising one or more of the antimicrobial peptides of the invention and a suitable pharmaceutical carrier. Such therapeutic compositions can be formulated and administered as known in the art, e.g., for oral, mucosal, inhalation, parenteral or topical application for controlling and/or preventing infection by a wide range of microorganisms including gram-positive and gram-negative bacteria.

In vitro antimicrobial activity of these peptides, as demonstrated herein, is an accurate predictor of in vivo antimicrobial activity.

Pharmaceutical compositions contain a therapeutically effective amount of one or more of the antimicrobial peptides and a suitable carrier. The carrier is chosen according to the intended use and route of administration. A therapeutically effective amount of an antimicrobial peptide can be readily determined according to methods well known in the art. For example, the amount will vary depending on the severity of an infection, concomitant therapy, subject parameters such as the age and the size/weight of a subject with an actual or potential infection of a given microorganism, and the route of administration and the like.

The present disclosure relates to compositions comprising one or more antimicrobial peptides disclosed herein in a microbicidal effective amount and a pharmaceutically acceptable carrier. Such compositions may additionally comprise a detergent. The addition of a detergent to such peptide compositions is useful to enhance antibacterial characteristics of the peptides. Although any suitable detergent may be used, the presently preferred detergent is a nonionic detergent such as Tween 20 or 1% NP40. Such antimicrobial pharmaceutical compositions can be formulated and administered in ways, as understood in the art for use local or systemic injection, for oral or topical application. In an embodiment, the antimicrobial peptides of the present invention can comprise from 0.0001% to 50% by weight of such compositions.

It will be understood that a composition for application, e.g. by systemic injection, contains an antimicrobial peptide in a therapeutically effective amount or a therapeutically effective amount of an antimicrobial peptide can be conjugated to another molecule with specificity for the target cell type. The other molecule can be an antibody, ligand, receptor, or other recognition molecule. In an embodiment, the choice of the peptide is made with consideration of immunogenicity and toxicity for an actually or potentially infected host, effective dose of the peptide, and the sensitivity of the target microbe to the peptide, as known in the art. In another embodiment the antimicrobial peptide(s) can be incorporated in a therapeutically effective amount into a composition for topical application, such as an ointment, gel, salve, lotion or other form, in which instance, the hemolytic activity is less important than for internal or oral administration.

In an embodiment, the method of inhibiting the growth of bacteria using the peptides disclosed herein may further include the addition of one or more other antimicrobial agents (e.g. a conventional antibiotic) for combination or synergistic therapy. The appropriate amount of the peptide administered will typically depend on the susceptibility of a bacterium such as whether the bacterium is Gram-negative or Gram-positive, and is easily discerned by one of ordinary skill in the art.

In an embodiment there is a composition that comprises the peptide, in an amount effective to kill a microorganism, and a suitable carrier. Such compositions may be used in numerous ways to combat microorganisms, for example in household or laboratory antimicrobial formulations using carriers well known in the art.

In an embodiment, there is a peptide comprising a derivative of D1 with respect to sequence, with the proviso that amino acids on the polar face can be varied with respect to positively charged residues at positions 1, 3, 7, 10, 11, 14, 15, 18, 22, and 26. Desirably these residues are lysine residues (or serine or threonine residues). At positions on the nonpolar face of the helix, 13 and 16 or others can be substituted with a conservative amino acid substitution or a nonconservative substitution such that there is the desired balance of net charge, distribution of hydrophobes and specificity determinants on the nonpolar face. In an embodiment, a derivative comprises a substitution of at least one amino acid residue. In an embodiment, a derivative comprises a truncation of at least one residue from an end. In an embodiment, a derivative comprises a truncation of at least two residues from an end. In an embodiment, a substitution replaces a hydrophilic residue for a hydrophobic residue. In an embodiment, a substitution replaces a hydrophobic residue for a hydrophilic residue. In an embodiment, a substitution replaces a hydrophilic residue with a different hydrophilic residue. In an embodiment, a substitution replaces a hydrophobic residue with a different hydrophobic residue. In an embodiment, a substitution replaces a residue with a different residue having a similar property, e.g., a polar side chain, a positively charged side chain, a negatively charged side chain, etc. In an embodiment, a substitution replaces an L-residue with a D-residue. In an embodiment, a substitution replaces a D-residue with an L-residue. In an embodiment, all residues are D-residues.

In an embodiment, there are provided peptide compositions as described herein, including fragments thereof; wherein the fragment length comprises a continuous stretch of at least about 14, at least about 17, at least about 20, at least about 23, at least about 24, or at least about 25 or about 26 amino acids or all integers between 14 and 28. In an embodiment, there is provided a peptide composition wherein said composition is at least about 70%, at least about 80%, at least about 90%, or at least about 95% homologous to a sequence of a peptide described herein, and all integers between 70 and 100. In an embodiment, there is provided a nucleic acid capable of encoding a peptide described herein. In an embodiment, a peptide of the invention is not SEQ ID NO:1 or any of SEQ ID NOs:2-62.

Where the peptides are to be used as antimicrobial agents, they can be formulated, for example, in buffered aqueous media containing a variety of salts and buffers. Examples of the pharmaceutical salts include, but are not limited to, halides, phosphates and sulfates, e.g., sodium chloride, potassium chloride or sodium sulfate. Various buffers may be used, such as citrate, phosphate, HEPES, Tris or the like to the extent that such buffers are physiologically acceptable to the host being treated and appropriate to the site of administration. Advantageously, preparations for intravenous or other use are sterile and/or meet standards for the intended route of administration, as known to the art.

Various excipients or other additives may be used, where the peptides are formulated as lyophilized powders, for subsequent use in solution. The excipients may include, without limitation, various emulsions, polyols, inert powders or other extenders and hydrophobic, amphiphilic or hydrophilic vehicles for formulation as salves, ointments or lotions for topical use.

"Therapeutically effective" as used herein, refers to an amount of formulation, composition, or reagent, optionally in a pharmaceutically acceptable carrier, that is of sufficient quantity to ameliorate the state of the patient or animal so treated. "Ameliorate" refers to a lessening of the detrimental effect of the infection or disorder in the recipient of the therapy. In an embodiment, a peptide of the invention is administered to a subject in need of treatment.

Pharmaceutically acceptable carrier preparations for administration include sterile or aqueous or nonaqueous solutions, suspensions, and emulsions. Examples of nonaqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solutions, Ringer's dextrose, dextrose and sodium chloride, lactated Ringer's, or fixed oils. Active therapeutic ingredients are often mixed with excipients that are pharmaceutically acceptable and compatible with the active ingredients. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antioxidants, chelating agents, and inert gases and the like. The actual dosage of the peptides, formulations or compositions containing such peptides can depend on many factors, including the size/weight, age, and health of an organism, however, one of ordinary skill in the art can use the following teachings and others known in the art describing the methods and techniques for determining clinical dosages (Spiker B., Guide to Clinical Studies and Developing Protocols, Raven Press, Ltd., New York, 1984, pp. 7-13, 54-60; Spiker B., Guide to Clinical Trials, Raven Press, Ltd., New York 1991, pp. 93-101; C. Craig. and R. Stitzel, eds., Modern Pharmacology, 2d ed., Little, Brown and Co., Boston, 1986, pp. 127-133; T. Speight, ed., Avery's Drug Treatment: Principles and Practice of Clinical Pharmacology and Therapeutics, 3d ed., Williams and Wilkins, Baltimore, 1987, pp. 50-56; R. Tallarida, R. Raffa and P. McGonigle, Principles in General Pharmacology, Springer-Verlag, new York, 1988, pp. 18-20) to determine the appropriate dosage to use.

In an embodiment, the dosages are generally in the range of about 0.001 mg/kg body weight of peptide to about 100 mg/kg peptide and preferably from about 0.001 mg/kg body weight to about 1 mg/kg of peptide are administered per day to an adult in any pharmaceutically acceptable carrier. The choice of carrier is determined, at least in part, by the route of administration of the pharmaceutical composition.

In another embodiment, an antimicrobial peptide may be used as a food preservative or in treating food products to control, reduce, or eliminate potential pathogens or contaminants. A peptide disclosed herein may be used as a disinfectant, for use in or with any product that must remain microbial free or be within certain tolerances. In an embodiment, treatment with a peptide provides at least partial regulation of infection or contamination.

In an embodiment it is also possible to incorporate or distribute the peptides within materials, on devices, or on objects (e.g. on an accessible surface), where microbial growth or viable presence is undesirable, as a method of microbicidal or microbistatic inhibition of microbial growth by administering to the devices or objects a microbicidal or microbistatic effective amount of peptide. In an embodiment, such devices or objects include, but are not limited to, linens, cloth, plastics, latex, fabrics, natural rubber, implantable devices, surfaces, or storage containers.

In an embodiment, there is provided a method of disinfecting a surface of an article, said method comprising the step of applying to said surface an effective amount of a composition comprising at least one microbial peptide of the invention. In an embodiment, the invention provides a disinfecting solution comprising at least one microbial peptide of the invention and optionally an acceptable carrier.

BRIEF DESCRIPTION OF THE DRAWINGS

FIGS. 1A1, 1A2, 1A3, 1B1, 1B2 and 1B3 illustrate the peptide D1 (SEQ ID NO:24) as a helical net and the sequences of certain synthetic peptide analogs of peptide D1 used in the present studies. These peptides are designed to vary charge on the polar face of the peptides. The substitution sites are triangled on the polar face and on the non-polar face. The specificity determinants (a single lysine residue K13 in the center of the non-polar face are triangled blue for peptides D1, D17-D22, peptide D5 contains two specificity determinants K13 and K16 in the center of the non-polar face, both of which are shown as blue triangles. In the peptide sequences of the present invention, all amino acids are D-amino acids. The polar face and non-polar face views of the peptides are shown. Conventional one-letter codes are used for the amino acid residues. Sequences of the other peptides are given in the Sequence Listing as follows: D17, SEQ ID NO:69; D18, SEQ ID NO:70; D19, SEQ ID NO:71; D20, SEQ ID NO:72; D21, SEQ ID NO:73 and D22, SEQ ID NO:74.

FIG. 6 shows D11, D15, D14 and D16 peptide sequences represented as helical nets showing the polar faces (top) and the non-polar faces (bottom). Colored blue are lysine residues on the polar face and lightly shaded circles are large hydrophobic Leu residues on the non-polar face and darker shaded circles are all other large hydrophobes on the non-polar face (Trp, Phe, Val and Ile). These four peptide's specificity determinant(s) dark shaded triangles (Lys) are shown in the center of the non-polar face. See also SEQ ID NO:63 (D11), SEQ ID NO:66 (D14), SEQ ID NO:67 (D15) and SEQ ID NO:68 (D16).

FIG. 7 shows D22 and D14 peptide sequences represented as helical nets showing the polar face (top) and the non-polar face (bottom). Shaded triangles are lysine residues on the polar face and lightly shaded circles are large hydrophobic Leu residues on the non-polar face and darker shaded circles are other large hydrophobes on the non-polar face (Trp, Phe, Val and Ile). These two peptides have one and two specificity determinants, respectively, shown as shaded triangles (Lys residue(s)) in the center of the non-polar face. See also SEQ ID NO:66 (D14) and SEQ ID NO:74 (D22).

FIG. 8 shows D14, D13, D12, D23, D24 and D16 peptide sequences represented as helical nets showing the polar faces (top) and the non-polar faces (bottom). Shaded triangles are lysine residues on the polar face and lightly shaded circles are large hydrophobic Leu residues on the non-polar face and darker shaded circles are all other large hydrophobes on the non-polar face (Trp, Phe, Val and Ile). These six peptides have two specificity determinants shown as shaded triangles (two Lys residues) in the center of the non-polar face. See also SEQ ID NO:64 (D12), SEQ ID NO:65 (D13), SEQ ID NO:66 (D14), SEQ ID NO:68 (D16), SEQ ID NO:75 (D23) and SEQ ID NO: 67 (D24).

DETAILED DESCRIPTION OF THE INVENTION

Figure 2A:
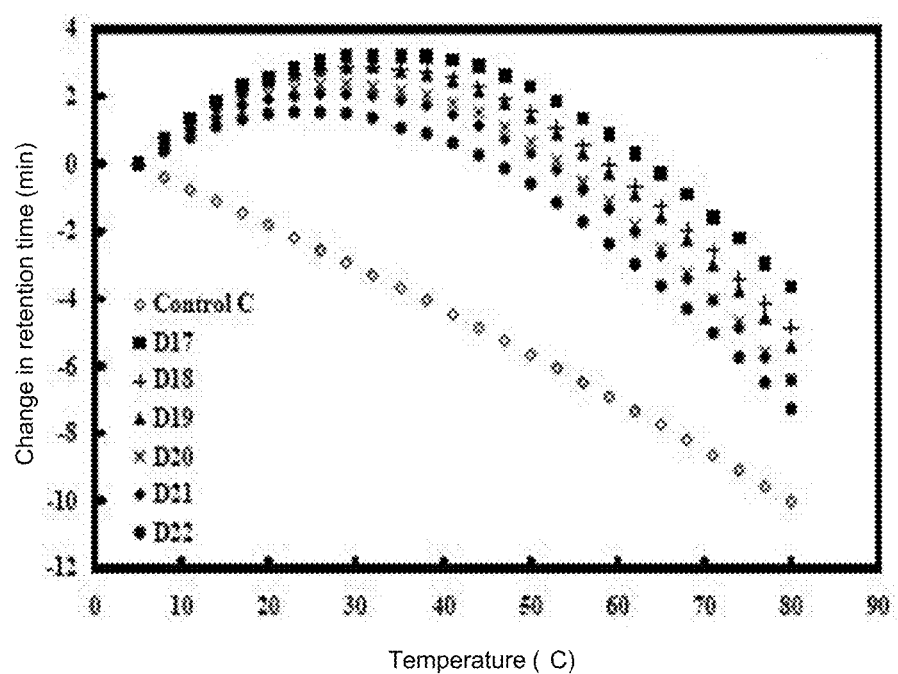
FIG. 2A, illustrates results of temperature profiling between 5 and 80° C. for peptides D17-D22 and control peptide C.

Due to the growing increase in antibiotic resistance, antimicrobial peptides (AMPs) have become important candidates as potential therapeutic agents. They have two unique features: a net positive charge of +2 or greater, or +5 to +11, owing to an excess of basic amino acids (Lys, Arg) over acidic amino acids (Asp, Glu); and an amphipathic nature, with a non-polar face and a polar face. The main target of such antimicrobial peptides is the cell membrane of microorganisms. A prior 26 amino acid residue peptide, V13K, showed that a single valine to lysine substitution (compared to its parent peptide) in the center of the non-polar face dramatically reduced toxicity and increased the therapeutic index. We then systematically substituted positively charged residues on the polar face to give a net positive charge from +5 to +11 as well as changing the relative location of these charged residues while maintaining the identical non-polar face for all analogs. We evaluated these peptide analogs for their antimicrobial activity against six clinical strains of *Pseudomonas aeruginosa* and their hemolytic activity to human red blood cells. Increasing net positive charge and varying the location of these charged residues had a dramatic effect on antimicrobial activity, hemolytic activity and the resulting therapeutic index. Also examined were antimicrobial activities against *Acinetobacter baumannii* and certain *Staphylococcus aureus* strains of clinical interest.

In general the terms and phrases used herein have their art-recognized meaning, which can be found by reference to standard texts, journal references and contexts known to those skilled in the art. The following definitions are provided to clarify their specific use in the context of the invention.

When used herein, the term "amino acid" is intended to refer to any natural or unnatural amino acid, whether made naturally or synthetically, including any such in L- or D-configuration. The term can also encompass amino acid analog compounds used in peptidomimetics or in peptoids. The term can include a modified or unusual amino acid or a synthetic derivative of an amino acid, e.g. diamino butyric acid and diamino propionic acid and the like. In the context of a peptide, an amino acid is synonymous with amino acid residue, as understood in the art.

The antimicrobial peptides of the invention are composed of amino acid residues linked together by peptide bonds. The peptides are in general in alpha helical conformation under hydrophobic conditions. Sequences are conventionally given from the amino terminus to the carboxyl terminus. Unless otherwise noted, the amino acids are L-amino acids. When all the amino acids are of L-configuration, the peptide is said to be an L-enantiomer. When all the amino acids are of D-configuration, the peptide is said to be a D-enantiomer.

The term "minimal inhibitory concentration" (MIC) refers to the lowest concentration of an antimicrobial agent (e.g., a peptide) required to prevent growth or otherwise modify a function of a microorganism under certain conditions, for example in liquid broth medium, and can be determined for a number of different microorganisms according to standard techniques well known in the art.

The term "minimal hemolytic concentration" (MHC) refers to the lowest concentration of an agent or peptide required to cause hemolysis of blood cells. MHC can be determined with red blood cells (RBC) from various species including human red blood cells (hRBC). $HC_{50}$ is the peptide concentration that causes 50% lysis of human red blood cells.

The term "therapeutic index" (TI) is the ratio of minimal hemolytic concentration (MHC) over minimal inhibitory concentration (MIC) of an antimicrobial agent. It can also be defined as the ratio of HC50 to the MIC value. Larger values generally indicate greater antimicrobial specificity.

The term "stability" can refer to an ability to resist degradation, to persist in a given environment, and/or to maintain a particular structure. For example, a peptide property of stability can indicate resistance to proteolytic degradation and to maintain an alpha-helical structural conformation.

An "aqueous environment" is a water based environment, including salt solutions and plasma and water-based gels and pharmaceutical excipients. Such an environment may or may not include surfactants or amphiphilic compounds for solubilizing hydrophobes.

The following abbreviations are used herein: A, Ala, Alanine; M, Met, Methionine; C, Cys, Cysteine; D, Asp, Aspartic Acid; E, Glu, Glutamic Acid; F, Phe, Phenylalanine; G, Gly, Glycine; H, H is, Histidine; I, Ile, Isoleucine; K, Lys, Lysine; L, Leu, Leucine; N, Asn, Asparagine; P, Pro, Proline; Q, Glu, Glutamine; R, Arg, Arginine; S, Ser, Serine; T, Thr, Threonine; V, Val, Valine; W, Trp, Tryptophan; Y, Tyr, Tyrosine; RP-HPLC, reversed-phase high performance liquid chromatography; MIC, minimal inhibitory concentration; MHC, minimal hemolytic concentration; CD, circular dichroism spectroscopy; TFE, trifluoroethanol; TFA, trifluoroacetic acid; RBC, red blood cells; hRBC, human red blood cells; $HC_{50}$, the peptide concentration that causes 50% lysis of human red blood cells.

The term "antimicrobial activity" refers to the ability of a peptide of the present invention to modify a function or metabolic process of a target microorganism, for example so as to at least partially affect replication, vegetative growth, toxin production, survival, viability in a quiescent state, or other attribute. In an embodiment, the term relates to inhibition of growth of a microorganism. In a particular embodiment, antimicrobial activity relates to the ability of an inventive peptide to kill at least one bacterial species. In a particular embodiment, the bacterial species is selected from the group consisting of gram-positive and gram-negative bacteria. In an embodiment, the term can be manifested as microbicidal or microbistatic inhibition of microbial growth.

The phrase "improved biological property" is meant to indicate that a test peptide exhibits less hemolytic activity and/or better antimicrobial activity, or better antimicrobial activity and/or less hemolytic activity, compared to the control peptide (e.g. $V_{681}$), when tested by the protocols described herein or by any other art-known standard protocols. In general, the improved biological property of the peptide is reflected in the therapeutic index (TI) value which is better that that of the control peptide.

The term "microorganism" herein refers broadly to bacteria, fungi, viruses, and protozoa. In particular, the term is applicable for a microorganism having a cellular or structural component of a lipid bilayer membrane. In specific embodiments, the membrane is a cytoplasmic membrane. Pathogenic bacteria, fungi, viruses, and protozoa as known in the art are generally encompassed. Bacteria can include gram-negative and gram-positive bacteria in addition to organisms classified in orders of the class Mollicutes and the like, such as species of the *Mycoplasma* and *Acholeplasma* genera. Specific examples of potentially sensitive gram-negative bacteria include, but are not limited to, *Escherichia coli, Acinetobacter baumannii, Pseudomonas aeruginosa, Salmonella, Hemophilus influenza, Neisseria, Vibrio cholerae, Vibrio parahaemolyticus* and *Helicobacter pylori*. Examples of potentially sensitive gram-positive bacteria include, but are not limited to, *Staphylococcus aureus, Staphylococcus epidermis, Streptococcus agalactiae*, Group A streptococcus, *Streptococcus pyogenes, Enterococcus faecalis*, Group B gram-positive streptococcus, *Corynebacterium xerosis*, and *Listeria monocytogenes*. Examples of sensitive fungi can include yeasts such as *Candida albicans*. Examples of sensitive viruses can include measles virus, herpes simplex virus (HSV-1 and -2), herpes family members (HIV, hepatitis C, vesicular, stomatitis virus (VSV), visna virus, and cytomegalovirus (CMV). Examples of sensitive protozoa can include *Giardia*.

"Therapeutically effective" as used herein, refers to an amount of formulation, composition, or reagent in a pharmaceutically acceptable carrier or a physiologically acceptable salt of an active compound, that is of sufficient quantity to ameliorate the undesirable state of the patient, animal, material, or object so treated. "Ameliorate" refers to a lessening of the detrimental effect of the disease state or disorder, or reduction in contamination, in the receiver of the treatment.

The peptides of the invention have antimicrobial activity by themselves or when covalently conjugated or otherwise coupled or associated with another molecule, e.g., polyethylene glycol or a carrier protein such as bovine serum albumin, so long as the peptides are positioned such that they can come into contact with a cell or unit of the target microorganism. These peptides may be modified by methods known in the art provided that the antimicrobial activity is not destroyed or substantially compromised.

The invention may be further understood by the following non-limiting examples.

Derivatives of Peptide $V_{681}$ with Modified Activity.

In prior studies discussed hereinafter, the 26-residue peptide having the sequence Ac-KWKSFLKTFKSAVKTV-LHTALKAISS-amide ($V_{681}$, SEQ ID NO:1) was utilized as the framework to study the effects of peptide hydrophobicity/hydrophilicity, amphipathicity and helicity by one or more amino acid substitutions in the center of the polar and non-polar faces of the amphipathic helix on biological activities. These studies demonstrate i) the importance of the peptide self-association parameter in the de novo design of amphipathic α-helical antimicrobial peptides; ii) that disruption of α-helical structure in benign conditions by D-amino acid substitutions or substitutions of hydrophilic/charged L-amino acids on the non-polar face can dramatically alter specificity; and iii) that these substitutions enhance antimicrobial activity, decrease toxicity and improve antimicrobial specificity while maintaining broad spectrum activity for gram-negative and gram-positive bacteria.

Peptide $V_{681}$, a 26-residue amphipathic antimicrobial peptide with a polar and non-polar face (28), was selected as the native parent peptide in this study. Its polar face consists of 14 residues: six lysine residues, one histidine, four serines, and three threonines. In contrast, the non-polar face consists of 12 residues: three alanines, two valines, three leucines, two phenylalanines, one isoleucine and one tryptophan residue. In this study, we chose D-/L-amino acid substitution sites at the center of the hydrophobic face (position 13) and at the center of the hydrophilic face (position 11) of the helix, such that these substitution sites were also located in the center of the overall peptide sequence. This was based on our previous model peptide studies (26,31,34) that demonstrated that these central location substitutions had the greatest effect on peptide secondary structure. To study the effects of varying hydrophobicity/hydrophilicity on peptide biological activities, in the design of $V_{681}$ analogs, five L-amino acids (Leu, Val, Ala, Ser, Lys) and Gly were selected out of the 20 natural amino acids as the substituting residues, representing a wide range of hydrophobicity. The hydrophobicity of these six amino acid residues decreases in the order Leu>Val>Ala>Gly>Ser>Lys (26). Based on the relative hydrophobicity of amino acid side-chains (26), leucine was used to replace the native valine on the non-polar face to increase peptide hydrophobicity and amphipathicity; alanine was selected to reduce peptide hydrophobicity and/or amphipathicity while maintaining high helicity; a hydrophilic amino acid, serine, was selected to decrease the hydrophobicity/amphipathicity of $V_{681}$ in the non-polar face; positively-charged lysine was used to decrease further peptide hydrophobicity and amphipathicity. In contrast, the same amino acid substitutions on the polar face would have different effects on the alteration of hydrophobicity/hydrophilicity and amphipathicity, since the native amino acid residue is serine on the polar face of $V_{681}$. As a result, on the polar face, leucine, valine and alanine were used to increase peptide hydrophobicity as well as decrease the amphipathicity of $V_{681}$, while lysine was selected to increase peptide hydrophilicity and amphipathicity. Previously, Kondejewski et al. (20, 35) and Lee et al. (25) successfully utilized D-amino acid substitutions to dissociate the antimicrobial activity and hemolytic activity of gramicidin S analogs. D-enantiomers of the five L-amino acid residues were also incorporated at the same positions on the non-polar/polar face of $V_{681}$ to change not only peptide hydrophobicity/hydrophilicity and amphipathicity but, more importantly, disrupt peptide helical structure. Since glycine does not exhibit optical activity and has no side-chain, the Gly-substituted analog was used as a reference for diastereomeric peptide pairs.

Since most peptide analogs were made based on a single amino acid substitution in either the polar or nonpolar faces of $V_{681}$, peptides were divided into two categories, N-peptides (nonpolar face substitutions) and P-peptides (polar face substitutions). Each peptide was named after the substituting amino acid residue, e.g., the peptide analog with L-leucine substitution on the nonpolar face of $V_{681}$ is called $NL_L$. It is important to note that since the L-valine of the non-polar face and L-serine of the polar face are the original amino acid residues in the $V_{681}$ sequence, peptide analogs $NV_L$ and $PS_L$ are the same peptide as $V_{681}$.

A control peptide (peptide C) designed to exhibit negligible secondary structure, i.e., a random coil, was employed as a standard peptide for temperature profiling during RP-HPLC to monitor peptide dimerization. As shown in the previous study (29), this 18-residue peptide, with the sequence of Ac-ELEKGGLEGEKGGKELEK-amide (SEQ ID NO:26) exhibited negligible secondary structure, even in the presence of the strong alpha-helix inducing properties of 50% trifluoroethanol (TFE) and at the low temperature of 5° C. ($[\theta]_{222}$=–3,950).

To determine the secondary structure of peptides in different environments, circular dichroism (CD) spectra of the peptide analogs were measured under physiologically related pH and ionic strength (100 mM KCl, 50 mM aq. $PO_4$, pH 7 referred to as benign conditions) and also in 50% TFE to mimic the hydrophobic environment of the membrane. The native peptide, $V_{681}$, exhibited low alpha-helical content in benign conditions, i.e., $[\theta]_{222}$ of –12,900 compared to –27,300 in 50% TFE, an increase in α-helical content from 45% to 94%, respectively. In benign conditions, D-amino acid substituted peptides generally exhibited considerably less α-helical structure compared to their L-diastereomers. The negligible secondary structure characteristics of the D-peptides underlines the helix-disrupting properties of a single D-amino acid substitution, as demonstrated in our previous model (26). On the non-polar face, the native L-Val residue was critical in maintaining α-helical structure. Substitution of L-Val with less hydrophobic amino acids (L-Ala, Gly, L-Ser and L-Lys) dramatically decreased the α-helical structure ($NV_L$, $[\theta]_{222}$ of –12,900 to values ranging from –1,300 to –3,450 for $NS_L$, $NK_L$, NG and $NA_L$). Even the substitution with L-Ala, which is known to have the highest α-helical propensity of all 20 amino acids (34), could not stabilize the α-helical structure. This shows the importance of hydrophobicity on the non-polar face in maintaining the α-helical structure. In contrast, substitution with a more hydrophobic amino acid (L-Leu for L-Val) on the non-polar face significantly increased α-helical structure ($[\theta]_{222}$ for peptide $NL_L$ of –20,600 compared to peptide $NV_L$ of –12,900). It is noteworthy that, on the non-polar face, the magnitude of the helical content of L-peptides in benign buffer was related to the hydrophobicity of the substituting amino acids, i.e., $NL_L$>$NV_L$>$NA_L$>$NS_L$, $NK_L$, again showing the importance of hydrophobicity on the non-polar face in maintaining the α-helical structure. Due to their helix-disruptive ability, on the non-polar face, the D-amino acid substitutions D-Val and D-Leu dramatically decreased α-helical structure in benign medium compared to their L-counterparts. However, whether L- or D-substitutions were made on the non-polar face, high helical structure could be induced by the hydrophobic environment of 50% TFE, a mimic of the membrane's hydrophobicity and α-helix inducing ability. Although D-amino acid substituted peptides were strongly induced into helical structure in 50% TFE, they were still generally less helical than the L-diastereomers, indicating that D-substitutions were still destabilizing of α-helical structure compared to their L-diastereomers in a hydrophobic environment.

The L-substitutions on the polar face in benign medium had dramatically different effects on α-helical structure than the same substitutions on the non-polar face. For example, $NL_L$ ($[\theta]_{222}$ of $-20,600$) differed from $PL_L$ ($[\theta]_{222}$ $-10,850$), indicating that Leu stabilized α-helical structure on the non-polar face and destabilized α-helical structure on the polar face. Similarly, Val destabilized α-helical structure on the polar face; on the other hand, Ala and Ser destabilized helical structure on the non-polar face, whilst, Ala and Ser stabilized α-helical structure when substituted in the polar face, compared to the other amino acid substitutions. Taken together, even though Ala had the highest α-helical propensity of all 20 amino acids (34), its α-helical propensity could not overcome the need for hydrophobicity on the non-polar face ($[\theta]_{222}$ for peptides $NA_L$, $-3,450$ and $NL_L$, $-20,600$); whereas, on the polar face, peptide $PA_L$ exhibited high helical structure in benign ($[\theta]_{222}$ $-13,600$) in contrast to peptide $PL_L$ ($[\theta]_{222}$ $-10,850$). It is noteworthy that Val and Leu substitutions on the polar face decreased the amphipathicity of the helix as well as increased the hydrophobicity; however, the lower helical content compared with the native $PS_L$ indicated that there should be a balance of amphipathicity and hydrophobicity to enhance the helical content. Similar to the substitutions on the non-polar face, all D-amino acid substitutions on the polar face were destabilizing to α-helical structure in benign medium; however, highly helical structure could be induced by adding 50% TFE. Non-polar face substitutions exhibit a greater range of molar ellipticity values in benign conditions than polar face analogs, demonstrating that the amino acid residues on the non-polar face of the helix played a more important role in peptide secondary structure than those on the polar face. As expected, Gly was destabilizing to α-helical structure whether on the non-polar or polar face due to its low α-helical propensity (34).

In benign conditions, peptide $NL_D$ showed much less helical structure than $NL_L$ due to the helix-destabilizing ability of the D-amino acid; whilst, in 50% TFE, both peptides could be induced to a fully helical structure. In contrast, in benign condition, peptides $NK_L$ and $NK_D$ were random coils, due to the combined effects of decreasing hydrophobicity and amphipathicity by replacing the native L-Val to D-/L-Lys on the non-polar face; again, in 50% TFE, both of them were induced into highly helical structures, albeit that peptide $NK_L$ demonstrated slightly more helical content than peptide $NK_D$.

Enantiomeric peptides of $V_{681}$ and analogs $NK_L$ and $NA_D$ were analyzed. Peptides $V_{681}$ and $NK_L$ contain all L-amino acids and $D-V_{681}$ and $D-NK_D$ contain all D-amino acids. In the case of $NA_D$ and $D-NA_L$, position 13 is D-alanine and L-alanine, respectively (Table 1). Thus, $D-V_{681}$, $D-NK_D$ and $D-NA_L$ are opposite in stereochemistry to the corresponding L-peptides, $V_{681}$, $NK_L$ and $NA_D$, respectively. A control peptide C designed to exhibit negligible secondary structure, i.e., a random coil, was employed as a standard peptide for temperature profiling during RP-HPLC to monitor peptide dimerization (53, 19, 29).

To determine the secondary structure of the D-enantiomeric peptides in different environments, CD spectra of the peptide analogs were measured under benign conditions (100 mM KCl, 50 mM $KH_2PO_4/K_2HPO_4$, pH 7.4, referred to as KP buffer) and also in 50% trifluoroethanol (TFE) to mimic the hydrophobic environment of the membrane. The parent peptide, $V_{681}$, was only partially helical in KP buffer; peptides $NK_L$ and $NA_D$ exhibited negligible secondary structure in KP buffer due to disruption of the non-polar face of the helix by introducing a hydrophilic L-lysine residue into peptide $NK_L$ or a helix-disruptive D-alanine residue into peptide $NA_D$. However, in the presence of 50% TFE, all three L-peptides were fully folded α-helical structures with similar ellipticities and helicity. As expected, the D-peptides showed spectra that were exact mirror images compared to their L-enantiomers, with ellipticities equivalent but of opposite sign both in benign KP buffer and in 50% TFE.

Temperature profiling during RP-HPLC has been used to determine the self-association ability of the various analogs of $V_{681}$ which would occur through interaction of the non-polar faces of these amphipathic α-helices. See WO 2006/065977. Using model amphipathic α-helical peptides with all 20 amino acid substitutions in the center of the non-polar face, we had shown previously that the model amphipathic peptides were maximally induced into an α-helical structure in 40% TFE and that the stability of the α-helix during temperature denaturation was dependent on the substitution (26). In order to investigate the stability of $V_{681}$ in a hydrophobic environment, we carried out a temperature denaturation study in solution, as monitored by circular dichroism spectroscopy. We used 50% aqueous TFE in 0.05% TFA to mimic the hydrophobic conditions in the reversed-phase column since the hydrophobic environment of a reversed-phase column (hydrophobic stationary phase and the hydrophobic organic solvent in the mobile phase) could induce α-helical structure in a similar manner to TFE. The change of $V_{681}$ helical conformation over the temperature range from 5° C. to 80° C. in the hydrophobic medium has been demonstrated. At 5° C., 50% TFE induced full α-helical structure of $V_{681}$. During the temperature denaturation, the helical content of $V_{681}$ decreased with increasing temperature but even at 80° C. $V_{681}$ remained significantly α-helical. The stability profile of $V_{681}$ with a transition temperature $T_m$ of 79.3° C., where $T_m$ is defined as the temperature when 50% of α-helical structure is denatured compared with the fully folded conformation of the peptide in 50% TFE at 5° C. has been shown in WO 2006/065977. These data support the view, that during temperature profiling in RP-HPLC, the peptides are fully helical at low temperatures such as 5° C. and can remain in the α-helical conformation at 80° C. in solution during partitioning in RP-HPLC. In addition, due to their hydrophobic preferred binding domains, the peptides will remain α-helical when bound to the hydrophobic matrix. Overall, these results indicate that $V_{681}$ is a very stable α-helical peptide in a hydrophobic environment, whether it is in solution (such as 50% TFE), under the conditions of RP-HPLC or in the hydrophobic environment of the membrane.

The formation of a hydrophobic binding domain due to peptide secondary structure can affect peptide interactions with reversed-phase matrices, this effect having been observed especially for amphipathic α-helical peptides (26, 36-39). Indeed, Zhou et al. (39) clearly demonstrated that, because of this preferred binding domain, amphipathic α-helical peptides are considerably more retentive than non-amphipathic peptides of the same amino acid composition. In addition, the chromatography conditions characteristic of RP-HPLC (hydrophobic stationary phase, nonpolar eluting solvent) are able to induce and stabilize helical structure in potentially helical polypeptides (39-41) in a manner similar to that of the helix-inducing solvent TFE. It has been shown (WO 2006/065977) that the substitution site at position 13, in the center of the nonpolar face of the helix, ensures a maximal effect on the intimate interaction of the substituting side-chain with the reversed-phase stationary phase; thus, any differences in effective hydrophobicity via amino acid substitutions in the preferred binding domain can be readily monitored through consequent differences in RP-HPLC retention time.

Temperatures of 5° C. and 80° C. were the lower and upper temperature limits of temperature profiling in RP-HPLC, representing dimerization of the peptides at 5° C. and the monomerization of peptides at 80° C. due to dissociation of the dimers. The maximal retention times represent the threshold points at which peptides transform from dimeric to monomeric form. Among the non-polar face substituted peptides, peptides with more hydrophobic substitutions (whether L- or D-amino acid substitutions) were more retained during RP-HPLC, i.e., peptides were eluted in the order of Lys, Gly, Ser, Ala, Val and Leu. In addition, on the non-polar face, the L-analogs were always more retained than the D-diastereomers. Because the aforementioned preferred binding domain of amphipathic helices is actually the non-polar face of the helix, D-peptides had a smaller preferred binding domain compared with L-diastereomers, due to the helix disruptive ability of D-amino acids, resulting in lower retention times during RP-HPLC. In contrast, on the polar face, the elution order of peptides was not correlated with the order of amino acid side-chain hydrophobicity, e.g., $PA_L$ and $PS_L$ were more retained than $PV_L$; $PS_D$ was the most retained peptide among the D-amino acid substituted analogs on the polar face. Indeed, on the polar face, peptides $PL_L$ and $PA_L$, with the replacement of L-Ser by L-Leu or L-Ala, had increased overall hydrophobicity as revealed by higher retention times compared with $V_{681}$.

Although amino acid L-Val is much more hydrophobic than L-Ser, the observation that peptide $PV_L$ was less retained than the native peptide $V_{681}$ (with L-Ser at position 11 of the polar face) could be attributed to the helix-disrupting characteristics of the β-branched Val residue. In contrast, at 80° C., $PV_L$ was better retained than $PS_L$. Due to the unfolding of the helical structure at high temperature, the side-chain hydrophobicity of the substituting amino acid in the peptide plays a more important role in the overall hydrophobicity. In a similar manner to the non-polar face substituted peptides, peptides with D-amino acids substituted into the polar face were dramatically less retained than their L-diastereomers. Due to the effect of the preferred binding domain, peptides with substitutions on the non-polar face had a greater retention time range than those with polar face substitutions, e.g., 11.31 min for the L-peptides with non-polar face substitutions versus 2.40 min for the L-peptides with polar face substitutions at 5° C., and 11.05 min versus 3.27 min for the D-peptides with non-polar or polar face substitutions, respectively, at 5° C.

The ability of the D-peptides to self-associate was determined by RP-HPLC temperature profiling over a temperature range of 5° C. to 80° C. As expected, L- and D-peptide enantiomers were totally inseparable over this temperature range, since each pair of peptides is identical in sequence and must adopt identical conformations on interacting with the reversed-phase matrix, whether in an all-L- or all-D-conformation. RP-HPLC retention behavior has been frequently utilized to represent overall peptide hydrophobicity (53,26). In the present study, the hydrophobicity of the three peptide pairs is in the order $V_{681}$/D-$V_{681}$>$NA_D$/D-$NA_L$>$NK_L$/D-$NK_D$, which agrees with the change in hydrophobicity of the substitutions at position 13 in order of the most hydrophobic to the least hydrophobic amino acid residue (Val in $V_{681}$>Ala in NA>Lys in NK) (54). For example, the retention times of peptides $V_{681}$/D-$V_{681}$ increase with increasing temperature (up to ~30° C.) followed by a retention time decrease with a further temperature increase. Such a temperature profile is characteristic of a peptide exhibiting self-association (53, 29, 19). The peptide self-association parameter, $P_A$, represents the maximum change in peptide retention time relative to the random coil peptide C. Since peptide C is a monomeric random coil peptide in both aqueous and hydrophobic media, its retention behavior over the temperature range 5° C. to 80° C. represents only general temperature effects on peptide retention behavior, i.e., a linear decrease in peptide retention time with increasing temperature due to greater solute diffusivity and enhanced mass transfer between the stationary and mobile phases at higher temperatures (55). Thus, after normalization to the retention times of peptide C, the retention behavior of the peptides represents only peptide self-association ability. Note that the higher the $P_A$ value, the greater the self-association ability. The order of peptide self-association ability of the three pairs of peptide enantiomers is identical to the order of peptide hydrophobicity, i.e., $V_{681}$/D-$V_{681}$ have the highest dimerization ability in solution among the three pairs of peptide enantiomers ($P_A$=7.2); in contrast, $NA_D$/D-$NA_L$ showed a weaker ability to self-associate when compared to $V_{681}$/D-$V_{681}$ ($P_A$=4.1); $NK_L$/D-$NK_D$ exhibited the lowest dimerization ability ($P_A$=2.1). It was determined that peptide retention times at 80° C. were dramatically lower than those at 5° C. Apart from the decrease in retention time due to the general temperature effects noted above, unraveling of the α-helix also occurs with increasing temperature, resulting in the loss of the non-polar face of the amphipathic α-helical peptides and, hence, reduced retention times as the peptides become increasingly random coils.

Elution times during RP-HPLC have frequently been utilized as a measure of relative hydrophobicity of peptide analogs (26,31). In the current study, peptide analogs differed only by a single amino acid substitution on either the non-polar face or the polar face of $V_{681}$; thus, retention time data can be considered to reflect the hydrophobicity difference between peptide analogs. In order to more easily visualize the variation in hydrophobicity of the peptide analogs, the retention time data in Table 5 were normalized relative to that of the native peptide $V_{681}$ at 5° C. and 80° C., respectively. Hydrophobicity relative to the native peptide $V_{681}$ indicates an increase or decrease of the apparent peptide hydrophobicity with the different amino acid substitutions on the polar or non-polar face. Again, from Table 5 and FIG. 5, for non-polar face substituted peptides, there was a wide range of peptide hydrophobicity in the order L-Leu>L-Val>L-Ala>L-Ser>Gly>L-Lys at both 5° C. and 80° C. On both the non-polar and polar faces, the relative hydrophobicities of the D-peptides was always less than their L-diastereomers, indicating the helix-disrupting characteristic of D-amino acids also leads to disruption of the preferred binding domain of the helices. On both non-polar and polar faces, peptides exhibited a greater retention time range at 80° C. than at 5° C., also indicating that, due to the unfolding of the helical structures at 80° C., the side-chain hydrophobicity of the substituted amino acids played a more essential role in determining the overall hydrophobicity of the peptide analogs.

The hydrophobicity/hydrophilicity effects of substitutions on the non-polar face relative to the native peptide $V_{681}$ were large. For example, $NV_L$ to $NA_L$, to $NS_L$, and to $NK_L$ resulted in decreases in hydrophobicity of −4.45, −8.21 and −12.61 min at 80° C., respectively (Table 5). In fact, the same substitutions, i.e., $PV_L$ to $PA_L$, to $PS_L$, and to $PK_L$, resulted in overall hydrophobicity changes of the peptide by +0.45, −0.35 and −2.29 min at 80° C., respectively. This indicates that the polar face substitutions affected overall hydrophobicity of the peptide in a minor way relative to substitutions on the non-polar face. In fact, the effect was of 10 times less for Ala, >20 times less for Ser and >5 times less for Lys.

Since its introduction, the technique of RP-HPLC temperature profiling has been applied on several types of molecules, including cyclic β-sheet peptides (30), monomeric α-helices and α-helices that dimerize (29), as well as α-helices that dimerize to form coiled-coils (42). Although peptides are eluted from a reversed-phase column mainly by an adsorption/desorption mechanism (43), even a peptide strongly bound to a hydrophobic stationary phase will partition between the matrix and the mobile phase when the acetonitrile content becomes high enough during gradient elution. The proposed mechanism of action for temperature profiling of α-helical peptides in RP-HPLC has been explained in detail by Mant, et al. (29). In summary, the mechanism is based on four assumptions: (i) at low temperature, just as an amphipathic α-helical peptide is able to dimerize in aqueous solution (through its hydrophobic, nonpolar face), it will dimerize in solution during partitioning in reversed-phase chromatography; (ii) at higher temperatures, the monomer-dimer equilibrium favors the monomer as the dimer is disrupted; (iii) at sufficiently high temperatures, only monomer is present in solution; and (iv) peptide is always bound in its monomeric helical form to the hydrophobic stationary phase, i.e., the dimer can only be present in solution and disruption of the dimer is required for rebinding to the RP-HPLC matrix.

It is well accepted that the amphipathicity of antimicrobial peptides is necessary for their mechanism of action, since the positively-charged polar face will help the molecules reach the biomembrane through electrostatic interaction with the negatively-charged head groups of phospholipids, and then the nonpolar face of the peptides will allow insertion into the membrane through hydrophobic interactions, causing increased permeability and loss of barrier function of target cells (6,7). Thus, we believe that peptide self-association (i.e., the ability to dimerize) in aqueous solution is a very important parameter to understand antimicrobial activity. If the self-association ability of a peptide in aqueous media is too strong (forming dimers and burying the non-polar face), it could decrease the ability of the peptide to dissociate and penetrate into the biomembrane and to kill target cells.

As mentioned above, the dimerization is temperature-dependent. At low temperatures, peptides exist in a dimer-monomer equilibrium during RP-HPLC partitioning, with the dimeric unbound state favored and dissociation required for rebinding; thus, the retention times are relatively low. With the increase of temperature, equilibrium is shifted toward the monomeric form in solution due to the disruption of the dimer. The higher solution concentration of monomer during partitioning increases the on-rate for the bound state, and the retention time therefore increases. It should be noted that the increased temperature also introduces other general effects on retention time because of lower mobile phase viscosity and a significant increase in mass transfer between the stationary phase and mobile phase. These effects decrease retention time with increasing temperature in a linear fashion, as shown for the random coil control peptide C. Conversely, for the dimerized peptides, at a given temperature dimers are disrupted and converted to monomers and the retention time reaches the maximal value. Above this critical temperature, one will observe a decrease in retention time with increasing temperature because of the low mobile phase viscosity and increase in mass transfer. In addition, the above described temperature-induced conformational changes, as monitored by CD, may also have an impact by decreasing the retention time with increasing temperature, largely due to the destabilization of peptide α-helical structure and loss of preferred binding domain at high temperatures. To eliminate these general effects during RP-HPLC, the data were normalized relative to the temperature profile of the random coil peptide standard C, and normalized to the retention time at 5° C.

It was observed that the peptide analogs in this study showed dramatic varying dimerization ability in solution. The maximal values of the change of retention times (($(t_R^t-t_R^5$ for peptide)-($t_R^t-t_R^5$ for C)) were defined as the peptide association parameter ($P_A$) to quantify the association ability of peptide analogs in solution (Table 5). Peptides with higher relative hydrophobicity generally showed stronger self-association ability in solution. The $P_A$ values of the peptide with non-polar face substitutions were of the same order as their relative hydrophobicity, indicating that the hydrophobicity on the hydrophobic face of the amphipathic helix was essential during dimerization, since the dimers are formed by the binding together of the non-polar faces of two amphipathic molecules. In contrast, the different relationship between $P_A$ and the relative hydrophobicity of the peptides with polar face substitutions demonstrated that the hydrophobicity on the polar face of the helices plays a less important role in peptide association. Generally speaking, the $P_A$ values of L-peptides were significantly greater than those of their D-diastereomers, indicating the importance of helical structure during dimerization. In most cases, the peptides with polar face substitutions had greater $P_A$ values than the corresponding peptide analogs with the same amino acid substitutions on the non-polar face. This is exactly what one would expect since polar face substitutions have little effect on the preferred dimerization domain, whereas non-polar face substitutions would dramatically affect the hydrophobicity and dimerization ability of the peptide.

Amphipathicity of the L-amino acid substituted peptides was determined by the calculation of hydrophobic moment (32) using the software package Jemboss version 1.2.1 (33), modified to include the hydrophobicity scale determined in our laboratory (see WO 2006/065977 for details). Peptide amphipathicity, for the non-polar face substitutions, was directly correlated with side-chain hydrophobicity of the substituted amino acid residue, i.e., the more hydrophobic the residue the higher the amphipathicity (values of 6.70 and 5.60 for $NL_L$ and $NK_L$, respectively); in contrast, on the polar face, peptide amphipathicity was inversely correlated with side-chain hydrophobicity of the substituted amino acid residue, i.e., the more hydrophobic the residue, the lower the amphipathicity (compare $PK_L$ and $PL_L$ with amphipathicity values of 6.62 and 5.45, respectively).

The native sequence, $V_{681}$ was very amphipathic with a value of 6.35. To place this value in perspective, the sequence of $V_{681}$ can be shuffled to obtain an amphipathic value of 0.96 (KHAVIKWSIKSSVKFKISTAFKATTI, SEQ ID NO: 41) or a maximum value of 8.10 for the sequence of HWSKLLKS-FTKALKKFAKAITSWST (SEQ ID NO:42). The range of amphipathicity values achieved by single substitutions on the polar and non-polar faces varied from a low of 5.45 for $PL_L$ to a high of 6.70 for $NL_L$ (Table 5). Even though single substitutions changed the amphipathicity, all the analogs remained very amphipathic, e.g., even with a lysine substitution on the non-polar face, $NK_L$ has a value of 5.60.

TABLE 5

Amphipathicity of peptide analogs.

| Peptide | Amphipathicity[a] | Peptide | Amphipathicity[a] |
|---|---|---|---|
| $NL_L$[b] | 6.70 | $PL_L$ | 5.45 |
| $NV_L$[b] | 6.35 | $PV_L$ | 5.82 |
| $NA_L$ | 5.98 | $PA_L$ | 6.21 |

TABLE 5-continued

Amphipathicity of peptide analogs.

| Peptide | Amphipathicity[a] | Peptide | Amphipathicity[a] |
|---|---|---|---|
| NG | 5.85 | PG | 6.35 |
| $NS_L$ | 5.85 | $PS_L$[b] | 6.35 |
| $NK_L$ | 5.60 | $PK_L$ | 6.62 |

Amphipathicity was determined by the calculation of hydrophobic moment (31) using hydrophobicity coefficients determined by reversed-phase chromatography (see Materials and Methods for details).
Peptides $NV_L$ and $PS_L$ are the same peptide as $V_{681}$.

Concerning the mechanism of action of antimicrobial peptides, many models have been proposed, among which the "barrel-stave" mechanism and the "carpet" model are two (44). In brief, the "barrel-stave" mechanism describes the formation of transmembrane channels/pores by bundles of amphipathic α-helices, as their hydrophobic surfaces interact with the lipid core of the membrane and the hydrophilic surfaces point inward, producing an aqueous pore (45); in contrast, the "carpet" model was proposed for the first time to describe the mechanism of action of dermaseptin S (46), describing the contact of antimicrobial peptides with the phospholipid head group throughout the entire process of membrane permeation which occurs only if there is a high local concentration of membrane-bound peptide. The major difference between the two mechanisms is, in the carpet model, peptides lie at the interface with their hydrophobic surface interacting with the hydrophobic component of the lipids but are not in the hydrophobic core of the membrane, and neither do they assemble the aqueous pore with their hydrophilic faces. A NMR study has shown that the cyclic β-sheet peptide analog of gramicidin S lays in the interface region parallel with the membrane where its hydrophobic surface interacts with the hydrophobic fatty acyl chains and the positively charged residues can still interact with the negatively charged head groups of the phospholipids (47).

Whichever the mechanism, the prerequisite step is the attraction of the peptide molecule to the membrane, followed by insertion into the bilayer. If peptide molecules self-associate in aqueous solution, peptides with lower self-associating ability in an aqueous medium can more easily penetrate into the lipid membrane. Peptides with higher relative hydrophobicity on their non-polar face created higher amphipathicity and generally showed stronger self-associating ability in solution; in contrast, for peptides with polar face substitutions, increasing hydrophobicity lowers amphipathicity yet the peptides still strongly self-associate, which indicates that peptide amphipathicity plays a less important role in peptide self-association when changes in amphipathicity are created on the polar face. In addition, self-associating ability is correlated with the secondary structure of peptides, i.e., in this study, disrupting the peptide helical structure by replacing the L-amino acid with its D-amino acid counterpart decreases the $P_A$ values.

The hemolytic activity of the peptides against human erythrocytes was determined as a major measure of peptide toxicity toward higher eukaryotic cells. As mentioned before, the native peptide $V_{681}$ (also named as $NV_L$ or $PS_L$) had strong hemolytic activity, with a minimal hemolytic concentration (MHC value) of 15.6 µg/ml. In this study, due to the alteration of hydrophobicity, amphipathicity and stability, the hemolytic activity of the best variants of peptide $V_{681}$ was significantly decreased to no detectable activity, a >32 fold decrease for $NK_L$.

For the non-polar face substituted peptides, hemolytic activity was correlated, at least in part, with the side-chain hydrophobicity of the substituting amino acid residue, i.e., the more hydrophobic the substituting amino acid, the more hemolytic the peptide, consistent with our previous study on the β-sheet antimicrobial peptide gramicidin S (22). For example, the MHC of peptide $NL_L$ was 7.8 µg/ml; in contrast, the MHC was decreased, parallel with the reduction of hydrophobicity, to an undetectable level for peptide $NK_L$. Peptide hydrophobicity and amphipathicity on the non-polar face were also correlated with peptide self-associating ability, thus peptides with less self-association in benign conditions also exhibited less hemolytic activity against eukaryotic cells. In contrast, for polar face substituted peptides, the relationships between self-association, hydrophobicity/amphipathicity and hemolytic activity were less clear. Of course, the hydrophobic non-polar face remained very similar when L-substitutions were made on the polar face; thus, dimerization and hydrophobicity of the non-polar face would be less affected and hemolytic activity would remain relatively strong.

In addition to hydrophobicity/amphipathicity, peptide helicity seemed to have an additional effect on hemolytic activity. In general, on both the non-polar and polar faces, D-amino acid substituted peptides were less hemolytic than their L-diastereomers. For example, $NA_L$ had a MHC value of 31.2 µg/ml compared to $NA_D$ with a value of 250 µg/ml, an 8-fold decrease in hemolytic activity. Similarly, $PV_L$ had a MHC value of 7.8 µg/ml compared to $PV_D$ with a value of 125 µg/ml, a 16-fold decrease in hemolytic activity. This phenomenon generally correlated with peptide self-associating ability, since D-diastereomeric analogs exhibited weaker self-associating ability than L-analogs. Additionally, D-substitutions disrupt helicity which, in turn, disrupts hydrophobicity of the non-polar face. This result was also consistent with the data of Shai and coworkers (23,24), who demonstrated that, through multiple D-amino acid substitutions, the helicity of peptides is substantially reduced leading to decreased hemolytic activity. Thus, peptide structure is important in the cytotoxicity towards mammalian cells although these disturbed helices can still maintain antibacterial activity.

Peptide analogs with non-polar face substitutions exhibited a greater range of hemolytic activity (7.8 µg/ml to not detectable) than the polar face substitutions (4 to 125 µg/ml), again indicating that the non-polar face of the helix may play a more essential role during the interaction with the biomembrane of normal cells. As expected, the peptides with the polar face substitutions showed stronger hemolytic activity than the peptides with the same amino acid substitutions on the non-polar face, which may be attributed to the different magnitude of the hydrophobicity change by the same amino acid substitutions on different sides of the amphipathic helix. Interestingly, in this study, all polar face substituted peptides except $PL_D$, $PV_D$ and $PK_D$ showed stronger hemolysis of erythrocytes than $V_{681}$; in contrast, on the non-polar face, only peptides $NL_D$ and $NL_L$ were more hemolytic than $V_{681}$.

For gram-negative bacteria, disruption of peptide helicity out weighted other factors in the improvement of antimicrobial activity; i.e., in most cases, the peptides with D-amino acid substitutions showed better antimicrobial activity than L-diastereomers. The exceptions were peptides $NS_D$ and $NK_D$. The reason for the low activity of peptides $NS_D$ and $NK_D$ was possibly the combined effects of the destabilization of the helix, the decrease of hydrophobicity on the non-polar face and the disruption of amphipathicity, highlighting the importance of maintaining a certain magnitude of hydrophobicity and amphipathicity on the non-polar face of the helix for biological activity, i.e., perhaps there is a combined threshold of helicity and hydrophobicity/amphipathicity required for biological activity of α-helical antimicrobial peptides. In this study, peptide self-associating ability (relative hydrophobicity) seemed to have no general relationship to MIC; however, interestingly, for peptides with L-hydrophobic amino acid substitutions (Leu, Val and Ala) in the polar and non-polar faces, the less hydrophobic the substituting amino acid, the more active the peptide against gram-negative bacteria.

Therapeutic index is a widely employed parameter to represent the specificity of antimicrobial reagents. It is calculated by the ratio of MHC (hemolytic activity) and MIC (antimicrobial activity); thus, larger values in therapeutic index indicate greater antimicrobial specificity. As mentioned above, the native peptide $V_{681}$ is a peptide with good antimicrobial activity coupled with strong hemolytic activity; hence, its therapeutic index is low (1.8 and 2.5 for gram-negative and gram-positive bacteria, respectively) and comparable to general toxins like melittin. By altering peptide hydrophobicity/hydrophilicity, amphipathicity and helicity, the therapeutic index of peptide $V_{681}$ against gram-negative bacteria was significantly increased by 90-fold and Gram-positive bacteria by 23-fold as previously demonstrated. There was a greater range of therapeutic indices for peptides with the non-polar face substitutions compared with the polar face substitutions, which was consistent with peptide self-association studies, indicating that the non-polar face of the helix may play a more important role in the mechanism of action.

*Pseudomonas aeruginosa* strains used in this study are a diverse group of clinical isolates from different places in the world. Antibiotic susceptibility tests show that these *Pseudomonas aeruginosa* strains share similar susceptibility to most antibiotics except that there is about a 64-fold difference for the range of ciprofloxacin susceptibility.

The "barrel-stave" and the "carpet" mechanisms are the two main theories used to explain the mechanism of action of antimicrobial peptides. However, neither mechanism alone can fully explain the data herein. For example, the hemolytic activity is correlated to the peptide hydrophobicity and amphipathicity on the non-polar face, which may be consistent with the "barrel-stave" mechanism, i.e., peptides interact with the hydrophobic core of the membrane by their non-polar face to form pores/channels. In contrast, the antimicrobial activity is not correlated with peptide hydrophobicity/amphipathicity, showing that the "barrel-stave" mechanism may not be suitable to explain the mechanism of antimicrobial action. Indeed, the "carpet" mechanism may best explain the interaction between the peptides and the bacterial membrane. Based on the above observations, we propose that both mechanisms are in operation for the peptides used in this study, i.e., the mechanism depends upon the difference in membrane composition between prokaryotic and eukaryotic cells. If the peptides form pores/channels in the hydrophobic core of the eukaryotic bilayer, they would cause the hemolysis of human red blood cells; in contrast, for prokaryotic cells, the peptides lyse cells in a detergent-like mechanism as described in the "carpet" mechanism.

Indeed, it is believed that the extent of interaction between peptide and biomembrane is dependent on the composition of lipid bilayer. For example, Liu, et al. (48-50) utilized a polyleucine-based α-helical transmembrane peptide to demonstrate that the peptide reduced the phase transition temperature to a greater extent in phosphatidylethanolamine (PE) bilayers than in phosphatidylcholine (PC) or phosphatidylglycerol (PG) bilayers, indicating a greater disruption of PE organization. The zwitterionic PE is the major lipid component in prokaryotic cell membranes and PC is the major lipid component in eukaryotic cell membranes (51,52). In addition, although PE also exists in eukaryotic membranes, due to the asymmetry in lipid distribution, PE is mainly found in the inner leaflet of the bilayer while PC is mainly found in the outer leaflet of the eukaryotic bilayer. Without wishing to be bound by theory, it is believed that the antimicrobial specificity of the antimicrobial α-helical peptides is a result of the composition differences of the lipid bilayer between eukaryotic and bacterial cells.

Two examples were selected for further study. The results for peptide $NK_L$, the peptide with the highest therapeutic index against Gram-negative bacteria, can be explained using the combined model. For example, if hemolysis of eukaryotic cells requires insertion of the peptide into the hydrophobic core of the membrane, which depends on the composition of the bilayer, and interaction of the non-polar face of the amphipathic α-helix with the hydrophobic lipid environment, it is believed that disruption of the hydrophobic surface with the Lys substitution ($NK_L$) would both disrupt dimerization of the peptide and its interaction with the hydrophobic lipid. Thus, the peptide is unable to penetrate the hydrophobic core of the membrane and unable to cause hemolysis. The effects of the Lys residue substituted in the center of the non-polar face are reflected in its being called a "specificity determinant." That is, this substitution gives the peptide specificity for prokaryotic membranes compared to eukaryotic membranes. On the other hand, if the mechanism for prokaryotic cells allows the interaction of monomeric peptides with the phospholipid headgroups in the interface region, then no insertion into the hydrophobic core of the membrane is required for antimicrobial activity.

The biological activities of the D-enantiomeric peptides illustrated herein are consistent with the proposed model; each enantiomeric peptide pair has the same activities against prokaryotic and eukaryotic cell membranes supporting the prediction that the sole target for these antimicrobial peptides is the cell membrane. This model predicts that hemolysis of eukaryotic cells requires the peptides to be inserted into the hydrophobic core of the membrane, perpendicular to the membrane surface, and interaction of the non-polar face of the amphipathic α-helix with the hydrophobic lipid core of the bilayer. The peptide may thus form transmembrane channels/pores and the hydrophilic surfaces point inward, producing an aqueous pore ("barrel-stave" mechanism). In contrast, antimicrobial activity in prokaryotic cells, while maintaining specificity, requires the peptide to lie at the membrane interface parallel with the membrane surface and interaction of the non-polar face of the amphipathic α-helix with the hydrophobic component of the lipid and interaction of the positively charged residues with the negatively charged head groups of the phospholipid ("carpet" mechanism). What dictates the two different modes of interaction is the difference in lipid composition of prokaryotic and eukaryotic membranes. This mode of interaction of antimicrobial peptides which combines the above two mechanisms is termed a "membrane discrimination mechanism".

Using this model, it is understood that peptide $NK_L$ and D-$NK_D$ of the present study are non-hemolytic but at the same time possess excellent antimicrobial activity compared to the native sequence $V_{681}$ or D-$V_{681}$. Thus, the single substitution of Lys for Val at position 13 ($NK_L$ and D-$NK_D$) in the center of the non-polar face disrupts the hydrophobic surface due to the presence of the positive charge, preventing the peptide from penetrating the bilayer as a transmembrane helix in eukaryotic cells. The peptide is then excluded from the bilayer and, hence, is non-hemolytic. Discrimination is further improved with two positively charged residues (specificity determinants) on the nonpolar face of the peptides. In prokaryotic cells, the peptide is also excluded from penetrating the bilayer as a transmembrane helix but this is not required for excellent antimicrobial activity. Instead, the peptide can enter the interface region of the bilayer where disruption of the peptide hydrophobic surface by Lys can be tolerated and antimicrobial activity maintained.

In contrast, the observation that the antimicrobial activity of peptide $NL_L$ (with Leu at the substitution site) was less than that of $NK_L$, while its hemolytic activity was stronger (MIC values of 12.7 µg/ml for $NL_L$ versus 3.1 µg/ml for $NK_L$ against Gram-negative bacteria; hemolytic activity of 7.8 µg/ml for $NL_L$ versus no detectable hemolytic activity for $NK_L$) can also be explained by our combined model. Thus, peptide $NL_L$ has a fully accessible non-polar face required for insertion into the bilayer and for interaction with the hydrophobic core of the membrane to form pores/channels ("barrel-stave" mechanism), while the hemolytic activity of peptide $NL_L$ is dramatically stronger than peptide $NK_L$. On the other hand, due to the stronger tendency of peptide $NL_L$ to be inserted into the hydrophobic core of the membrane than peptide $NK_L$, peptide $NL_L$ actually interacts less with the water/lipid interface of the bacterial membrane; hence, the antimicrobial activity is 4-fold weaker than the peptide $NK_L$ against Gram-negative bacteria. This supports the view that the "carpet" mechanism is essential for strong antimicrobial activity and if there is a preference by the peptide for penetration into the hydrophobic core of the bilayer, the antimicrobial activity will actually decrease.

The studies disclosed herein demonstrate that a high ability of a peptide to self-associate in solution correlates with weak antimicrobial activity and strong hemolytic activity of the peptides. Biological studies further show that strong hemolytic activity of the peptides generally correlates with high hydrophobicity, high amphipathicity and high helicity. In most cases, the D-amino acid substituted peptides possessed an enhanced average antimicrobial activity compared with L-diastereomers. The therapeutic index of $V_{681}$ was improved 90-fold and 23-fold against gram-negative and gram-positive bacteria, respectively, by substitution of Lys in the center of the non-polar face, i.e., the substitution of a "specificity determinant" in the center of the non-polar face. Although the antimicrobial peptides exemplified are the analogs having five amino acid (L, V, A, S, K) substitutions at position 11 or 13 in the 26-residue peptide, $V_{681}$, other substitutions such as ornithine, arginine, histidine or other positively charged residues at these sites are believed to also improve antimicrobial activity of the peptides. It is further believed that similar substitutions at position 16 or 17 of $V_{681}$ yield peptides with enhanced biological activity. Based on the studies disclosed herein, a person of ordinary skill in the art can design antimicrobial peptides with enhanced activities by simply replacing the central hydrophobic amino acid residue on the nonpolar face of an amphipathic molecule with a series of selected D-/L-amino acids.

Significant features of two specific antimicrobial peptides generated from this study in structural terms are as follows. In the case of $NK_L$, a positively-charged residue, lysine, is introduced in the center of the hydrophobic face. This substitution disrupts alpha-helical structure in benign medium, decreases dimerization, decreases toxicity to mammalian cells as measured by hemolytic activity, enhances antimicrobial activity and provides a 90-fold increase in the therapeutic index compared with the starting sequence against Gram-negative bacteria (substitution of starting material having Val 13 with a change to Lys 13). The therapeutic index is the ratio of hemolytic activity/antimicrobial activity. This same peptide has a 17-fold increase in the therapeutic index for Gram-positive bacteria. Lys substituted at position 13 is a "specificity determinant".

In the case of $NA_D$, a D-Ala residue is introduced into the center of the hydrophobic face. This disrupts alpha-helical structure, decreases dimerization, decreases toxicity to mammalian cells as measured by hemolytic activity, enhances antimicrobial activity and provides a 42-fold increase in the therapeutic index compared to the starting sequence against Gram-negative bacteria (substitution is Val 13 to D-Ala 13). This same peptide has a 23-fold increase in the therapeutic index for Gram-positive bacteria. D-Ala substituted at position 13 is a "specificity determinant".

Alpha-helical antimicrobial peptides are amphipathic. If the self-association ability of a peptide (forming dimers by interaction of the two non-polar faces of two molecules) is too strong in aqueous media, it could decrease the ability of the peptide monomers to dissociate, pass through the cell wall of microorganisms and penetrate into the biomembranes to kill target cells. It is clearly demonstrated in the studies using the D-enantiomeric peptides that there is a direct correlation of the ability of peptides to dimerize and specificity is generated, that is, disruption of dimerization generates specificity between eukaryotic and prokaryotic cells. From Table 7, the $P_A$ values of peptides derived from their temperature profiling data (FIG. 8) reflect the ability of the amphipathic α-helices to associate/dimerize. Clearly, $V_{681}$ and D-$V_{681}$, due to their uniform non-polar faces, show the greatest ability to dimerize in aqueous solution and lowest specificity or the strongest ability to lyse human erythrocytes. This is consistent with the view that a peptide with a fully accessible non-polar face tends to form pores/channels in the membranes of eukaryotic cells. In the case of $NA_D$ and D-$NA_L$, the introduction of D-Ala and L-Ala into all-L- and all-D-amino acid peptides, respectively, disrupts α-helical structure and, thus, lowers dimerization ability relative to $V_{681}$ and D-$V_{681}$ and improves specificity. The introduction of Lys into non-polar position 13 of $NK_L$ and D-$NK_D$ lowers this dimerization ability even further and improves specificity. Thus, the lack of ability of a peptide to dimerize, as exemplified by its $P_A$ value, is an excellent measure of the peptide's ability to be non-hemolytic concomitant with maintenance of sufficient hydrophobicity of the non-polar face to ensure antimicrobial activity. It is important to note that D-enantiomeric peptides exhibited the same self-association ability as their corresponding L-enantiomers; thus, similar biological activities can be expected. This is further supported by the fact that the hemolytic activity and antimicrobial activity of D-peptides against human red blood cells and microbial cells, respectively, were indeed quantitatively equivalent to those of the L-enantiomers. These results further demonstrate that there is no chiral selectivity by the membrane or other stereoselective interactions in the cytoplasm with respect to the hemolytic and antimicrobial activities.

Because of the different results on the hemolytic activity of peptide $NA_D$ as shown in WO 2006/065977 (250 µg/ml after 12 hours versus 31.3 µg/ml after 18 hours, respectively), albeit using the standard microtiter dilution method (see Methods), it became apparent that an investigation of the relationship between hemolysis and time was required. It is noteworthy that there is no universal protocol of determination of hemolytic activity, which makes it difficult to compare data from different sources. For example, some researchers use 4 hours of incubation and take the minimal concentration of peptide to give 100% hemolysis as peptide hemolytic activity (28, 56); in contrast, some use 12 hours or longer (e.g., 18 hours used herein) of incubation and take the maximal concentration of peptide to give no hemolysis as peptide hemolytic activity (53, 57). Hence, the hemolysis time study is important to understand the process of erythrocyte lysis. It is clear that the degree of cell lysis is correlated with time, which may be the main reason for the different values of hemolytic activity of $NA_D$ in the two studies. Regardless, the hemolytic activity of each test peptide can readily be appreciated by a skilled artisan by comparing the value of the test peptide with that of the control peptide ($V_{681}$) within a given study. Hence, we have established a stringent criterion for toxicity, which is no hemolysis at a peptide concentration of 500 μg/ml after 8 hours. We believe that this time study at this very high peptide concentration gives a much more accurate evaluation of hemolytic activity and this method should be established as the gold standard test.

It is important to note that peptides $NA_D$ and $NK_L$ are effective against a diverse group of Pseudomonas aeruginosa clinical isolates. Peptide $D-NA_L$ exhibited the highest antimicrobial activity against Pseudomonas aeruginosa strains; in contrast, $D-NK_D$ has the best overall therapeutic index due to its lack of hemolytic activity. As mentioned before, Pseudomonas aeruginosa is a family of notorious Gram-negative bacterial strains which are resistant to most of current antibiotics, thus, it is one of the most severe threats to human health (58-60). Only a few antibiotics are effective against Pseudomonas, including fluoroquinolones (61), gentamicin (62) and imipenem (63), and even these antibiotics are not effective against all strains. In the studies disclosed herein, MIC values for Pseudomonas aeruginosa and other Gram-negative and Gram-positive bacteria were determined in two different collaborating laboratories; in addition to different media used, the inoculum numbers of cells were also different, which may explain some variations of MIC values of Pseudomonas aeruginosa strains. Another particularly difficult gram-negative pathogen to treat is Acinetobacter baumannii, a pathogen endemic to the Middle East and on which is becoming a significant problem in hospitals in the United States.

In general, there is no significant difference in peptide antimicrobial activities against Pseudomonas aeruginosa strains, other Gram-negative and Gram-positive bacteria and a fungus between L- and D-enantiomeric peptides, or among peptides with different amino acid substitutions, i.e., $V_{681}$, $NA_D$ and $NK_L$. This observation provides understanding of the mechanism of action of α-helical antimicrobial enantiomeric peptides as follows: there is a dramatic difference in peptide hydrophobicity at position 13 between Val and Lys. The Lys disrupts the continuous non-polar surface due to the positive charge and causes the peptide to locate in the interface region of the microbial membrane. This supports the view that the "carpet" mechanism is essential for strong antimicrobial activity, i.e., for both L- and D-peptide enantiomers, the peptides kill bacteria by a detergent-like mechanism, without penetrating deeply into the hydrophobic core of membrane.

Based on the peptide degradation study, all-D-peptides were totally resistant to enzymatic digestion; hence, this may explain the slightly higher antimicrobial activity of D-peptides than that of their L-enantiomers against Pseudomonas aeruginosa and Gram-positive bacteria. The relatively high susceptibility of L-peptides to trypsin is no doubt due to the presence of multiple lysine residues in sequences, i.e., 6 lysines for $V_{681}$ and $NA_D$, 7 lysines for $NK_L$, resulting in the fast degradation of the L-peptides in 30 minutes even at a molar ratio of 20,000:1 (peptide:trypsin).

By comparing the biophysical and biological properties of L- and D-enantiomeric peptides, we showed that L- and D-enantiomeric peptide pairs behave the same in self-association ability in solution, had the same hemolytic activity against human red blood cells, and exhibited similar antimicrobial activity against Pseudomonas aeruginosa strains, and other Gram-negative and Gram-positive bacteria and a fungus. No chiral selectivity was found in the antimicrobial and hemolytic activities of the peptides. Thus, the results disclosed support the "membrane discrimination" model as the mechanism of action for both L- and D-enantiomeric peptides. It is important to note that peptide $D-NK_D$ showed dramatic improvements in therapeutic indices compared to the parent peptide $V_{681}$ i.e., 53-fold against Pseudomonas aeruginosa strains, 80-fold against Gram-negative bacteria, 69-fold against Gram-positive bacteria and 33-fold against C. albicans. The proteolytic stability of $D-NK_D$, its broad spectrum of activity and lack of hemolytic activity demonstrate its clinical potential as a new therapeutic (92).

Peptide Synthesis and Purification—

Syntheses of the peptides were carried out by solid-phase peptide synthesis using t-butyloxycarbonyl chemistry and MBHA (4-methylbenzhydrylamine) resin (0.97 mmol/g), as described previously, with cleavage of the peptides from the resin as described (26, 53, 92, 93). However, it is understood in the art that there are other suitable peptide synthetic devices or that manual peptide synthesis could be carried out to produce the peptides described herein.

The crude peptides were purified by reversed-phase chromatography (RP-HPLC) using a Zorbax 300 SB-$C_8$ column (250×9.4 mm I.D.; 6.5 μm particle size, 300 Å pore size; Agilent Technologies, Little Falls, Del.) with a linear AB gradient (0.1% acetonitrile/min) at a flow rate of 2 ml/min, where mobile phase A was 0.2% aqueous TFA in water and B was 0.2% trifluoroacetic acid (TFA) in acetonitrile, where the shallow 0.1% acetonitrile/min gradient started 12% below the acetonitrile concentration required to elute the peptide on injection of an analytical sample and employing a gradient of 1% acetonitrile/min (94).

The purities of the peptides were verified by analytical RP-HPLC as described below and were further characterized by mass spectrometry and amino acid analysis.

Analytical RP-HPLC and Temperature Profiling of the Peptides—

Crude and purified peptides were analyzed on an Agilent 1100 series liquid chromatograph (Little Falls, Del.). Runs were performed on a Zorbax 300 SB-$C_8$ column (150×2.1 mm I.D.; 5 μm particle size, 300 Å pore size) from Agilent Technologies using linear AB gradient (1% acetonitrile/min) and a flow rate of 0.25 ml/min, where eluant A was 0.2% aqueous TFA, pH 2 and eluant B was 0.2% TFA in acetonitrile.

Temperature profiling analyses were performed on the same column in 3° C. increments, from 5° C. to 80° C., using a linear AB gradient of 0.5% acetonitrile/min, as described previously (30, 53, 92, 93).

Characterization of Helical Structure—

The mean residue molar ellipticities of peptides are determined by circular dichroism (CD) spectroscopy, using a Jasco J-720 spectropolarimeter (Jasco, Easton, Md.), at 25° C. under benign conditions (50 mM $KH_2PO_4$/$K_2HPO_4$/100 mM KCl, pH 7), as well as in the presence of an α-helix inducing solvent, 2,2,2-trifluoroethanol (TFE) (50 mM $KH_2PO_4$/$K_2HPO_4$/100 mM KCl, pH 7 buffer/50% TFE). A 10-fold dilution of a ~500 μM stock solution of the peptide analogs is loaded into a 0.02 cm fused silica cell, and its ellipticity is scanned from 190 to 250 nm. The values of molar ellipticities of the peptide analogs at a wavelength of 222 nm are used to estimate the relative α-helicity of the peptides.

CD Temperature Denaturation Study of Peptide $V_{681}$—

The native peptide $V_{681}$ is dissolved in 0.05% aqueous TFA containing 50% TFE, pH 2, loaded into a 0.02 cm fused silica cell and peptide ellipticity scanned from 190 to 250 nm at temperatures of 5, 15, 25, 35, 45, 55, 65 and 80° C. The spectra at different temperatures are used to mimic the alteration of peptide conformation during temperature profiling analysis in RP-HPLC. The ratio of the molar ellipticity at a particular temperature (t) relative to that at 5° C. $([\theta]_t-[\theta]_u)/([\theta]_5-[\theta]_u)$ is calculated and plotted against temperature in order to obtain the thermal melting profiles, where $[\theta]_5$ and $[\theta]_u$ represent the molar ellipticity values for the fully folded and fully unfolded species, respectively. $[\theta]_u$ is determined in the presence of 8M urea with a value of 1500 deg·cm$^2$·dmol$^{-1}$ to represent a totally random coil state (31). The melting temperature ($T_m$) is calculated as the temperature at which the α-helix was 50% denatured $(([\theta]_t-[\theta]_u)/([\theta]_5-[\theta]_u)=0.5)$ and the values are taken as a measure of α-helix stability.

Determination of Peptide Amphipathicity—

Amphipathicity of peptide analogs is determined by the calculation of hydrophobic moment (32) using the software package Jemboss version 1.2.1 (33), modified to include a hydrophobicity scale determined in our laboratory. The hydrophobicity scale used in this study is as follows: Trp, 32.31; Phe, 29.11; Leu, 23.42; Ile 21.31; Met, 16.13; Tyr, 15.37; Val, 13.81; Pro, 9.38; Cys, 8.14; Ala, 3.60; Glu, 3.60; Thr, 2.82; Asp, 2.22; Gln, 0.54; Ser, 0.00; Asn, 0.00; Gly, 0.00; Arg, −5.01; His, −7.03; Lys, −7.03. These hydrophobicity coefficients are determined from reversed-phase chromatography at pH 2 of a model random coil peptide with single substitution of all 20 naturally occurring amino acids. In this case, the amphipathicity is valid for neutral and acidic pH since $V_{681}$ and analogs do not have Asp and Glu residues in their sequences. Without wishing to be bound by any particular theory, the inventors believe that that this HPLC-derived scale reflects the relative differences in hydrophilicity/hydrophobicity of the 20 amino acid side-chains more accurately than previously determined scales (see also references 54, 92).

Measurement of Antimicrobial Activity—

Minimal inhibitory concentrations (MICs) are determined using a standard microtiter dilution method, with 3 sets of determinations, in LB (Luria-Bertani) no-salt medium (10 g of tryptone and 5 g of yeast extract per liter). In some cases, Mueller Hinton (MH) medium or Brain Heart Infusion (BHI) medium is used.

Briefly, cells were grown overnight at 37° C. in LB and diluted in the same medium. Serial dilutions of the peptides are added to the microtiter plates in a volume of 100 μl followed by 10 μl of bacteria to give a final inoculum of $5\times10^5$ colony-forming units/ml. Plates are incubated at 37° C. for 24 hours and MICs determined as the lowest peptide concentration that inhibited growth. Alternatively, minimal inhibitory concentrations are determined using a standard microtiter dilution method in a Mueller-Hinton (MH) medium. Briefly, cells are grown overnight at 37° C. in MH broth and diluted in the same medium. In some cases, serial dilutions of the peptides are added to the microtiter plates in a volume of 100 μl followed by 10 μl of bacteria to give a final inoculum of $1\times10^5$ colony-forming units/ml. Plates are incubated at 37° C. for 24 hours and MICs are determined as the lowest peptide concentration that inhibited growth.

Pseudomonas aeruginosa Strains Used in this Study—

Strain PAO1 was isolated from a human wound in 1955 in Australia (95); strain WR5 was isolated from a burn patient at Walter Reed Army Hospital, Washington, D.C., in 1976 and is a natural toxA mutant isolate but is virulent in experimental mouse models (96, 97); strain PAK was originally isolated at Memorial University, St. John's, Newfoundland, Canada, and is widely used in the analysis of pili (98, 99); strain PA14 was originally isolated as a clinical isolate in 1995 at the Massachusetts General Hospital, Boston, and is virulent in a variety of plant and animal models of infection (100); strain M2 was originally isolated in 1975 from the gastrointestinal tract of a healthy CF1 mouse, University of Cincinnati College of Medicine, and Shriners Burns Institute, Cincinnati, Ohio, and is virulent in a burn mouse model of *P. aeruginosa* infection (101); and strain CP204 was isolated from a cystic fibrosis patient in 1989 at the National Jewish Medical and Research Center, Denver, Colo. All strains have been maintained at −80° C.

For MIC determination of *Pseudomonas aeruginosa* clinical isolates, brain heart infusion (BHI) medium is used instead of MH broth. In addition, the bacteria were diluted to a final inoculum of $1\times10^6$ colony-forming units/ml. MICs were determined by a standard microtiter dilution method in Mueller Hinton (MH) medium and Brain Heart Infusion (BHI) medium and were based on 3 sets of determinations. Serial dilutions (two-fold decrease that ranged from 1000 μg/ml to 1 μg/ml) of the 2× compound were added to the microtiter plates in a volume of 50 μL followed by 50 μL of bacteria to give a final inoculum of $1\times10^6$ colony-forming units (CFU)/mL. The plates were incubated at 37° C. for 24 h, and the MICs were determined as the lowest peptide concentration that inhibited growth.

Measurement of Hemolytic Activity—

Peptide samples were added to 1% human erythrocytes in phosphate buffered saline, pH 7.4 (0.1 M NaCl; 0.08 M $Na_{2H}PO_4$; 0.02 M $NaH_2PO_4$), and reactions were incubated at 37° C. for 18 hours in microtiter plates. Two-fold serial dilutions (ranged from 1000 μg/ml to 1 μg/ml) with 3 sets of determinations of the peptide samples were carried out in order to determine the concentration that produced no hemolysis. This determination was made by withdrawing aliquots from the hemolysis assays and removing unlysed erythrocytes by centrifugation (800×g). Hemoglobin release was determined spectrophotometrically at 570 nm. The hemolytic activity was determined as the peptide concentration that caused 50% hemolysis of erythrocytes after 18 h ($HC_{50}$). The control for no release of hemoglobin was a sample of 1% erythrocytes without any peptide added. Since erythrocytes were in an isotonic medium, no detectable release (<1% of that released upon complete hemolysis) of hemoglobin was observed from this control during the course of the assay. $HC_{50}$ was determined by a plot of peptide concentration versus percent lysis.

Calculation of Therapeutic Index ($HC_{50}$/MIC Ratio)—

The therapeutic index is a widely accepted parameter to represent the specificity of antimicrobial compounds between prokaryotic and eukaryotic cells. It is calculated by the ratio of $HC_{50}$ (hemolytic activity) and MIC (antimicrobial activity); thus, larger values of therapeutic index indicate greater antimicrobial specificity. It should be noted that both the HC and MIC values are carried out by serial two-fold dilutions; thus, for individual bacteria and individual peptides, the therapeutic index could vary as much as four-fold if the peptide is very active in both hemolytic and antimicrobial activities; of course, if a peptide has poor or no hemolytic activity, the major variation in the therapeutic index comes from the variation in the MIC value (as much as two-fold).

Peptide Analogs with Varied Position of Substitution.

Further peptides of the invention are generated by varying the position of a substitution. By denoting the center position as "i", varied positions of substitutions can be generated while retaining a preferred location on the desired face, e.g. the non-polar face. In the relative context of SEQ ID NO:1, for example, the position for substitution is selected from the group consisting of i, i−4, i−8, i+4, and i+8, or I, i−3, i−6, o+3, and i+6. Without wishing to be bound by a particular theory, it is hypothesized that a peptide with the substitution at position i of $K_L$ (e.g., in SEQ ID NO:6), in the center position of the non-polar face, can have greater biological activity than a peptide with a substitution at a position further away from the center position. According to such theory, the therapeutic index can decrease in the order of $K_L 13 > K_L 9 > K_L 5$ (here the numeral indicates the position of the amino acid substitution relative to SEQ ID NO:1). Similarly, the therapeutic index can decrease in the order of $A_D 13 > A_D 9 > A_D 5$ (here $A_D 13$ corresponds to SEQ ID NO:9). Regardless of such theory, such peptides with varied positions of a substitution can have activity and be useful in compositions and methods of the invention. Successful substitutions at position 13 can also work near the center of the hydrophobic face at position 9, 12, 16 and 17.

In order to evaluate the biological activities of the peptide analogs with varied position of substitution, we used peptide $NK_L$ as a framework to systematically alter the peptide hydrophobicity by replacing alanine residues with hydrophobic leucine residues on the non-polar face of the helix.

The results of studies described in WO 2006/065977 are consistent with the model of "membrane discrimination" mechanism of action for antimicrobial peptides whose sole target is the biomembrane. We believe that the mechanism depends upon the compositional difference in the lipids between prokaryotic and eukaryotic membranes. It is well-known that eukaryotic cell membranes are in contrast to prokaryotic membranes generally characterized by zwitterionic phospholipids, a relatively large amount of cholesterol and sphigomyelin, and the absence of a high, inside-negative transmembrane potential presented in prokaryotic membranes (51-52, 66-67). Hence, if the peptides form pores/channels in the hydrophobic core of the eukaryotic bilayer, they cause the hemolysis of erythrocytes; in contrast, for prokaryotic cells the peptides lyse cells in a detergent-like mechanism as described in the carpet mechanism (46).

Prior observations (WO 2006/065977 and WO 2010/042534) that there is a correlation between peptide hydrophobicity and hemolytic activity can be explained by the "membrane discrimination" mechanism. Peptides with higher hydrophobicity will penetrate deeper into the hydrophobic core of red blood cell membrane (67), causing stronger hemolysis by forming pores or channels, exhibited stronger hemolytic activity than single Leu-substituted peptides, and A12L/A20L/A23L showed the strongest hemolytic activity in this study. For peptide antimicrobial activity, since the insertion of the molecules into the hydrophobic core is not necessary to lyse bacterial cells during the antibacterial action, peptides only lie at the interface parallel with the membrane allowing their hydrophobic surface to interact with the hydrophobic component of the lipid, and the positive charge residues to interact with the negatively charged head groups of the phospholipids (46,47). Thus, it is reasonable to assume that increasing peptide hydrophobicity to a certain extent will help peptide molecules to reach the interface from aqueous environment and improve antimicrobial activity. In this study, the improvement of antimicrobial activity from peptide $NK_L$ (peptide 1) to peptide A20L (peptide 4) can represent such an advantage of increasing hydrophobicity. In contrast, further increases in hydrophobicity will cause the stronger peptide dimerization in solution which in turn results in the monomer-dimer equilibrium favoring the dimer conformation. Peptide dimers are in their folded α-helical conformation and would be inhibited from passing through the cell wall to reach the target membranes. Hence the antimicrobial activities of peptides A12L/A23L (peptide 5) and A12L/A20L (peptide 6) become weaker with increasing hydrophobicity compared to the single Leu-substituted analogs. We believe that there is a threshold of hydrophobicity controlling peptide antimicrobial activity, that is, one may adjust peptide hydrophobicity to obtain the optimal antimicrobial activity. For the extreme example of the triple-Leu-substituted analog, A12L/A20L/A23L (peptide 7), the loss of antimicrobial activity may be explained as due to its very strong dimerization ability in aqueous environments. Hence, the peptide exists mainly as a dimer in solution and it would not pass through the bacterial cell wall. In contrast, there is no polysaccharide-based cell wall in eukaryotic cells, thus, A12L/A20L/A23L (peptide 7) caused severe hemolysis against human red blood cells where the hydrophobicity of the bilayer causes rapid dissociation of dimers to monomers and entry into the bilayer to form channels/pores.

As shown in WO 2006/065977, further peptides were generated by varying the nature of the charged residue selected for the substitution. In the relative context of SEQ ID NO:1, for example, the position for substitution was established as position 13. The amino acid selected for substitution was preferably a charged amino acid and is in particular an amino acid with a net positive charge. Particular examples of charged residues at position 13 were Lys, Arg, Orn, His, diaminobutyric acid and diaminopropionic acid. Orn has a delta/δ-amino group instead of an epsilon/ε-amino group in Lys, i.e., the side-chain is shorter by one carbon atom; diaminobutyric acid is one carbon shorter than Orn; i.e., it has a gamma/γ-amino group; diaminopropionic acid is two carbons shorter than Orn, i.e., it has a beta/β-amino group.

A peptide with a charged residue in the center of the non-polar face can be active. Without wishing to be bound by any particular theory, it is hypothesized that the activity of a peptide with such a centrally positioned positively charged residue can be modulated depending on the positively charged residue, although there may be difficulty in predicting the precise effect upon an activity parameter such as the therapeutic index as described herein.

Figures 1, 7:
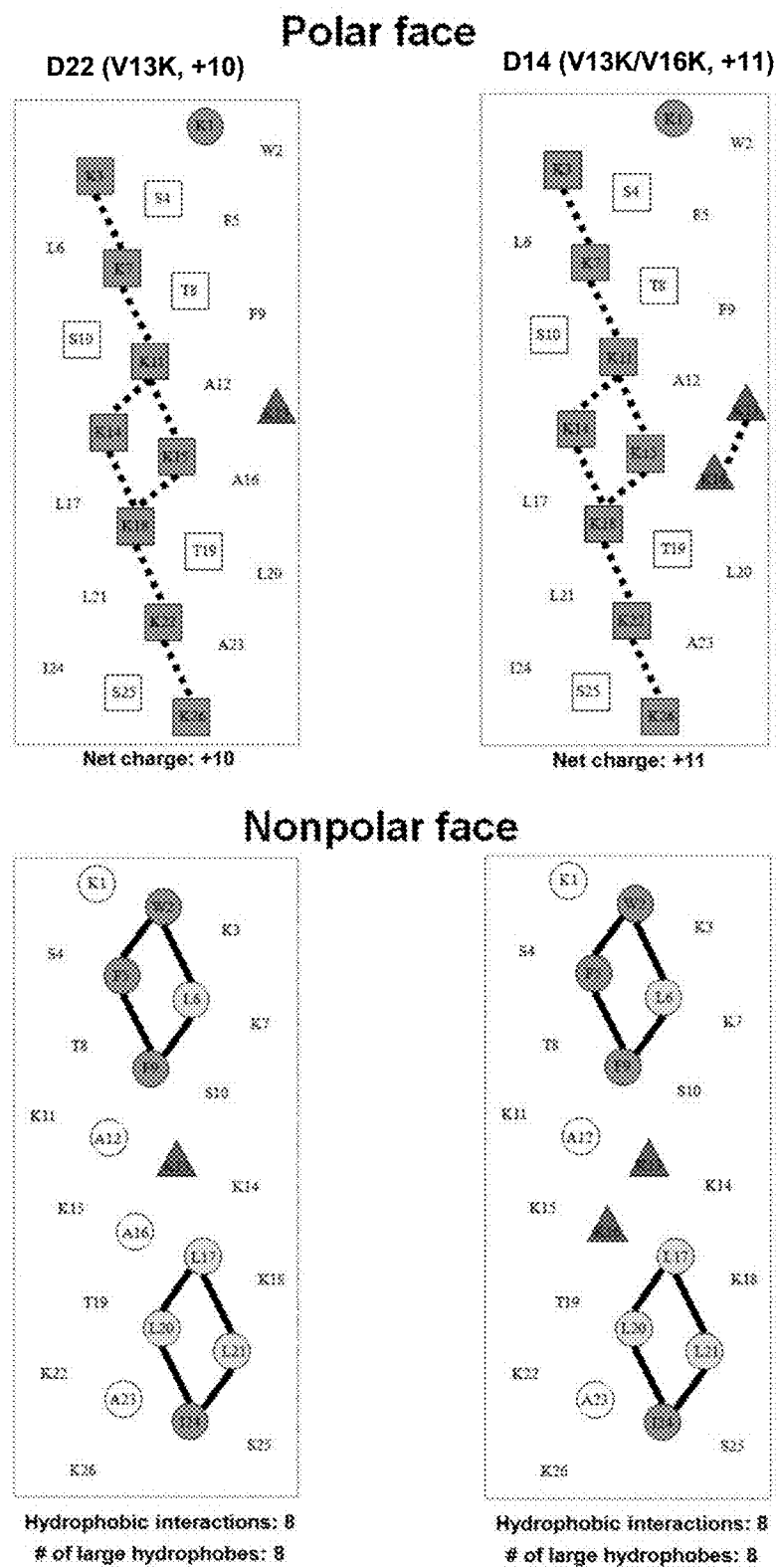

Further peptides were described in WO 2006/065977 and were generated by using multiple substitutions relative to a reference sequence such as SEQ ID NO:1. In a preferred embodiment, the multiple substitutions are a double substitution. In the relative context of SEQ ID NO:1, for example, the peptides are made with double substitutions: a) peptide with substitution combination of L6 to $A_D 6$ and L21 to $A_D 21$; and b) peptide with substitution combination of L6 to $K_L 6$ and L21 to $K_L 21$. See FIG. 7A therein for specific variant peptides achieved by optional multiple substitutions.

Without wishing to be bound by any particular theory, it has been hypothesized that the activity of a peptide with multiple substitutions (e.g. two substitutions) not in the center position can still be effective. For a particular peptide generated by multiple substitutions, such multiple substitutions can be at least as effective as a single substitution in the center of the non-polar face. Alternatively, a given multiple substitution such as the specific double substitutions shown may not be as effective as the single substitutions described herein due to the removal of two Leu residues instead of one Val residue. A decrease in hydrophobicity can optionally result in a decrease in the therapeutic index. In addition, the double D-Ala substitutions may be more disruptive of the helical structure; such disruption can also yield a decrease in the therapeutic index. Analogous results can be achieved for the double L-Lys substitutions.

TABLE 6A

Hydrophobicity Coefficients in an Antimicrobial Peptide

| Residue | Hydrophobicity Coefficient |
|---|---|
| Trp 2 | 32.31 |
| Phe 5 | 29.11 |
| Leu 6 | 23.42 |
| Phe 9 | 29.11 |
| Ala 12 | 3.60 |
| Lys 13 | −7.03 |
| Val 16 | 13.81 |
| Leu 17 | 23.42 |
| Ala 20 | 3.60 |
| Leu 21 | 23.42 |
| Ala 23 | 3.60 |
| Ile 24 | 21.31 |
| SUM | 199.7 ± 23.42 |

Different scales can give different values. For peptides herein, there is significance in the sum of the residues in the hydrophobic surface, using our scale, where the surface hydrophobicity range that generates the desired biological activity is from about 176 to about 224.

The sum of the hydrophobicity coefficients for the polar face should be the value for $NK_L$ peptide±the value of a Lys residue.

TABLE 6B

Coefficient values.

| Residue | Coefficient |
|---|---|
| K1 | −7.03 |
| K3 | −7.03 |
| S4 | 0.00 |
| K7 | −7.03 |
| T6 | +2.82 |
| K10 | −7.03 |
| S11 | 0.00 |
| K14 | −7.03 |
| T15 | +2.82 |
| H18 | −7.03 |
| T19 | +2.82 |
| K22 | −7.03 |
| S25 | 0.00 |
| S26 | 0.00 |
| SUM | −40.75 ± 7.03 |

Using this scale, the hydrophobicity of the polar face of $NK_L$ sums up the values K1, K3, S4, K7, T6, K10, S11, K14, T15, H18, T19, K22, S25 and S26. The range of surface hydrophilicity that generates the desired biological activity is from about −33 to about −48.

Further peptides were generated by making single substitutions of amino acid residues with relatively similar hydrophobicity. Single hydrophobicity substitutions with side-chains of similar hydrophobicity are generated and have biological activity. For example, possible substitutions for each residue in the non-polar face are listed below in the context of peptides $NK_L$ and $NA_D$ (SEQ ID NOS:6 and 9, respectively) in WO 2006/065977.

Residues for single substitutions in an antimicrobial peptide can be as follows: Leu: Ile, Val, norleucine, norvaline; Ile: Leu, Val, norleucine, norvaline; Val: Leu, Ile, norleucine, norvaline; Phe: Leu, Ile, Val, norleucine, norvaline; Trp: Phe, Leu, Ile, Val, norleucine, norvaline.

Further compositions and methods have been provided where the hemolytic activity of $NA_D$ or $D-NA_L$ is further decreased by decreasing the overall hydrophobicity of the non-polar face. See Kondejewski, L. H., et al. 2002 (22). For example, V16 is substituted to A16; or L17 to A17; or both V16, L17 to A16, A17. Decreased hydrophobicity can decrease hemolytic activity, as shown for substitutions herein at position 13. The hydrophobicity can decrease approximately in the order $NL_L > NV_L > NA_L > NG > NS_L > NK_L$ which correlates with the weakening of hemolytic activity (μg/ml) where $NL_L$ (7.8), $NV_L$ (15.6), $NA_L$ (31.2), NG (125), $NS_L$ (125) and $NK_L$ (no measurable activity). It is recognized that there can be a threshold of hydrophobicity which when excessively decreased can result in peptides where the biological property of antimicrobial activity is substantially reduced.

Peptide Design—

Figures 1, 6:
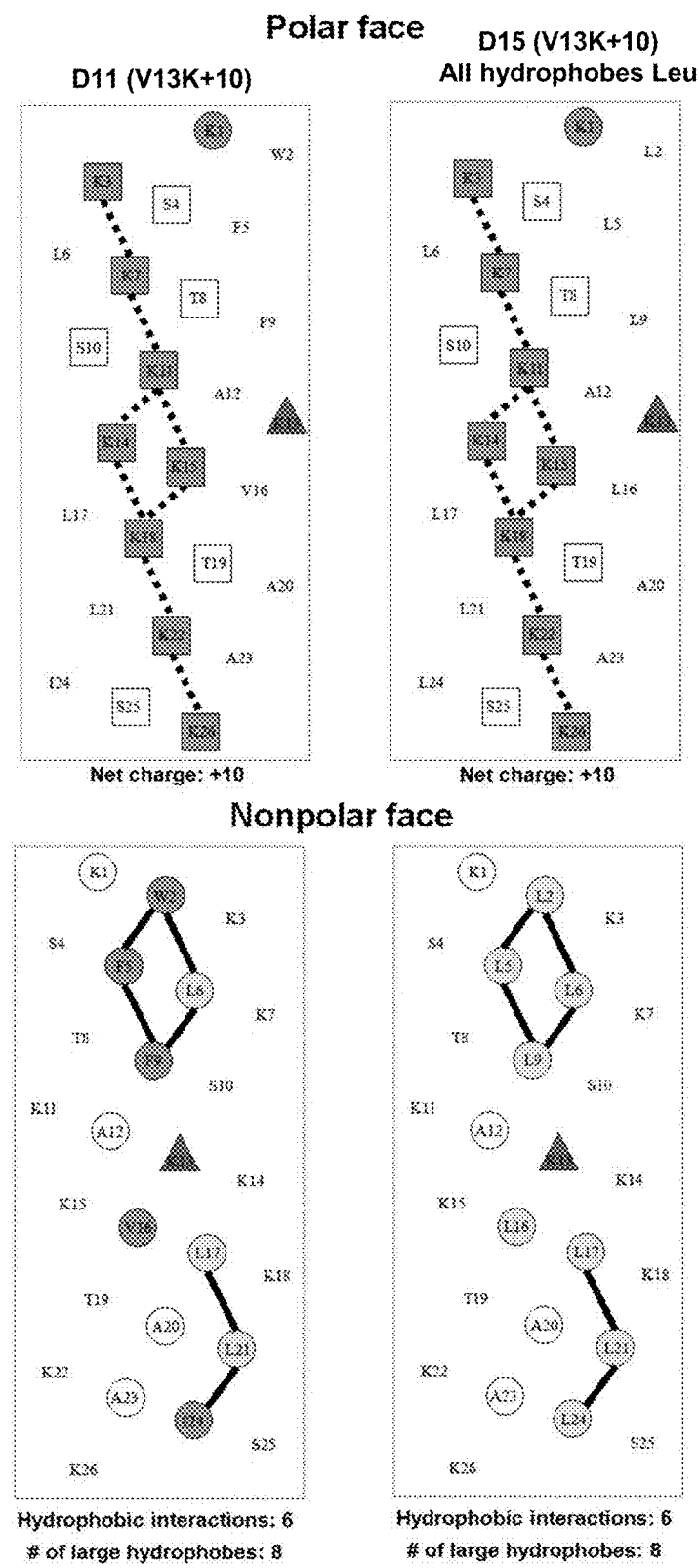

The peptide sequences for D17-D22 are shown in Table 3, with helical net representations (polar face and non-polar face) shown in FIG. 1A-1B. The i→i+3 and i→i+4 hydrophobic interactions on the non-polar face (a peptide sequence in an α-helical conformation allows a side-chain in position i to interact with a side-chain in position i+3 or i+4 along the sequence) and the i→i+3 and i→i+4 electrostatic repulsions on the polar face (which may affect folding and stability of monomeric α-helices) were also shown in FIG. 1. The parent peptide used in this study was D-V13K (D1), a 26-residue amphipathic peptide consisting of all D-amino acid residues, which adopts an α-helical conformation in a hydrophobic environment and contains a hydrophilic, positively-charged lysine residue in the center of the non-polar face (position 13) (FIG. 1) (53, 92, 93). This residue is referred to as a "specificity determinant", which reduces peptide toxicity to human cells. In this study, the net charge of the peptides varied from +5 for D17 to +10 for D22, while the number of the positively charged lysine residues on the polar face varied form 4 for D17 to 9 for D22. Advantageously, the specificity determinant comprises at least one additional positively charged amino acid residue at or near the center of the nonpolar face of the peptide.

TABLE 7

Biophysical Data and Hydrophobicity Information for Certain Antimicrobial Peptides

| Peptide Name | Hydrophobicity $T^a$ (min) | $P_A{}^b$ |
|---|---|---|
| D1 | 76.75 | 2.78 |
| D5 | 80.44 | 4.35 |
| D17 | 98.81 | 7.96 |
| D18 | 97.87 | 7.21 |
| D19 | 97.94 | 7.07 |
| D20 | 95.90 | 6.39 |
| D21 | 93.77 | 6.00 |
| D22 | 90.67 | 5.13 |

$^a$Denotes retention time in RP-HPLC at pH 2 and room temperature, and is a measure of overall peptide hydrophobicity.
$^b$Denotes dimerization parameter of each peptide during RP-HPLC temperature profiling, which is the maximal retention time difference of $(t_R^t - t_R^5$ for peptide analogs$) - (t_R^t - t_R^5$ for control peptide C) within the temperature range: $(t_R^t - t_R^5$ is the retention time difference of a peptide at a specific temperature ($t^t$) compared with that at 5° C. ($t^5$). The sequence of control peptide C is Ac-ELEKGGLEGEKGGKELEK-amide (SEQ ID NO: 26).

Peptide Self-Association—

Figure 2B:
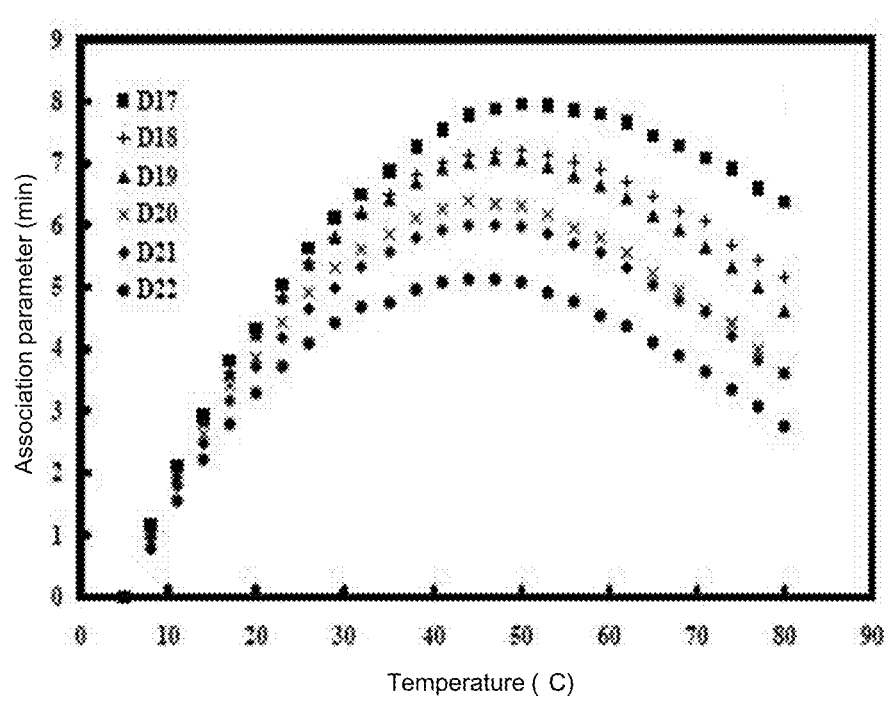
FIG. 2B, presents graphical results for analysis of association parameters plotted against temperatures between 5 and 80° C. for peptides D17-D22.

Peptide self-association (i.e., the ability to oligomerize/dimerize) in aqueous solution is a very important parameter for antimicrobial activity (53, 92, 93). Without wishing to be bound by any particular theory, the present inventors postulated that monomeric random-coil antimicrobial peptides are best suited to pass through the capsule and cell wall of microorganisms prior to penetration into the cytoplasmic membrane, induction of α-helical structure and disruption of membrane structure to kill target cells (93). Thus, if the self-association ability of a peptide in aqueous media is too strong (e.g., forming stable folded dimers through interaction of their non-polar faces) this could decrease the ability of the peptide to dissociate to monomer, in addition oligomerization of the peptide can prevent it from effectively passing through the capsule and cell wall to reach the membrane. The ability of the peptides in the present study to self-associate was determined by the technique of RP-HPLC temperature profiling at pH 2 (29, 30, 38). The reason pH 2 is used to determine self-association of cationic AMPs is that highly positively charged peptides are frequently not eluted from reversed-phase columns at pH 7 due to non-specific binding to negatively charged silanols on the column matrix. This is not a problem at pH 2 since the silanols are protonated (i.e., neutral) and non-specific electrostatic interactions are eliminated. At pH 2, the interactions between the peptide and the reversed-phase matrix involve ideal retention behavior, i.e., only hydrophobic interactions between the preferred binding domain (nonpolar face) of the amphipathic molecule and the hydrophobic surface of the column matrix are present (39). FIG. 2A shows the retention behavior of the peptides after normalization to their retention times at 5° C. Control peptide C shows a linear decrease in retention time with increasing temperature and is representative of peptides which have no ability to self-associate during RP-HPLC. Control peptide C is a monomeric random coil peptide in both aqueous and hydrophobic media; thus, its linear decrease in peptide retention behavior with increasing temperature within the range of 5° C. to 80° C. represents only the general effects of temperature due to greater solute diffusivity and enhanced mass transfer between the stationary and mobile phase at higher temperatures (55). To allow for these general temperature effects, the data for the control peptide was subtracted from each temperature profile as shown in FIG. 2B. Thus, the peptide self-association parameter, PA, represents the maximum change in peptide retention time relative to the random coil peptide C. Note that the higher the PA value, the greater the self-association.

Figure 3A:
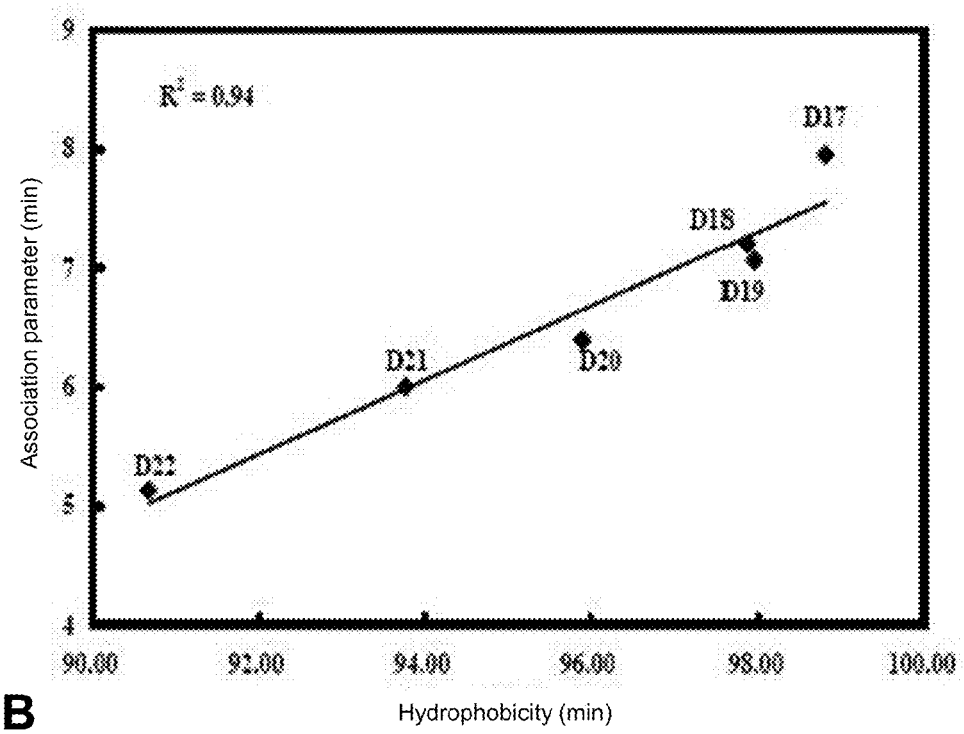
FIG. 3A, shows a plot of association parameters against hydrophobicity, for peptides D17-D22.
Figure 3B:
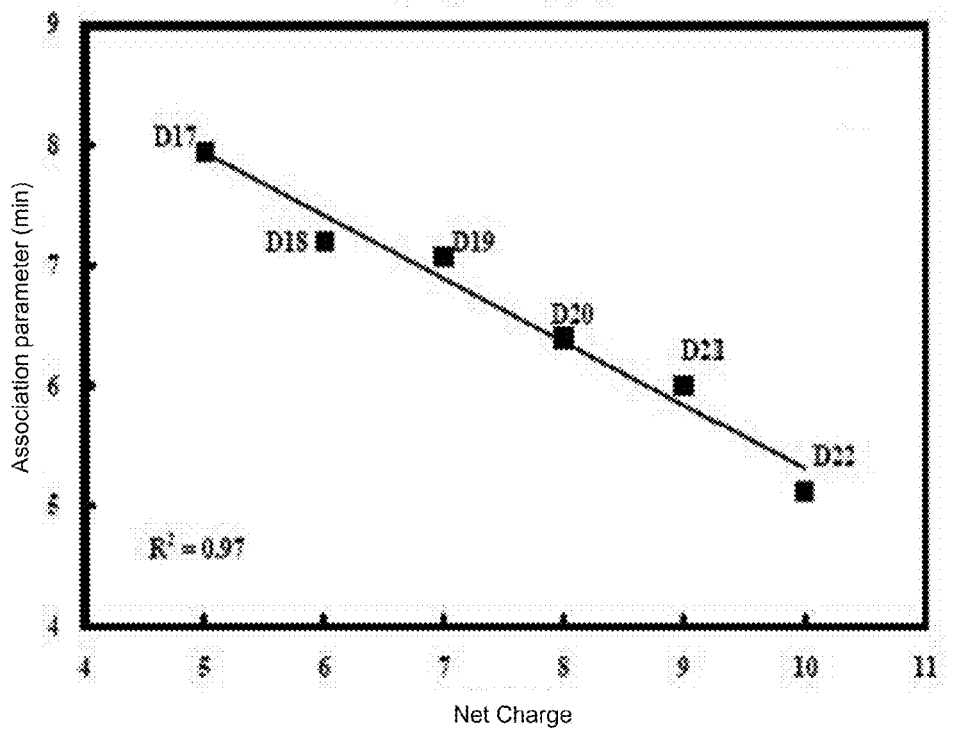
FIG. 3B, illustrates association parameter plotted against net charge for peptides D17-D22. The results demonstrate, inter alia, a positive correlation between association and hydrophobicity and a negative correlation between association parameter and net charge.

By systematically increasing the number of positively charged residues on the polar face, the peptide self-association ability dramatically decrease from 7.96 for D17 to 5.13 to D22 (Table 7). Although, all six analogs share the same nonpolar face, increasing the net charge decreases the association parameter (Table 7). The self-association ability increased linearly with the increasing of overall hydrophobicity (FIG. 3A) while decreased linearly with the increasing of net charge (FIG. 3B).

Hemolytic Activity—

Figure 4:
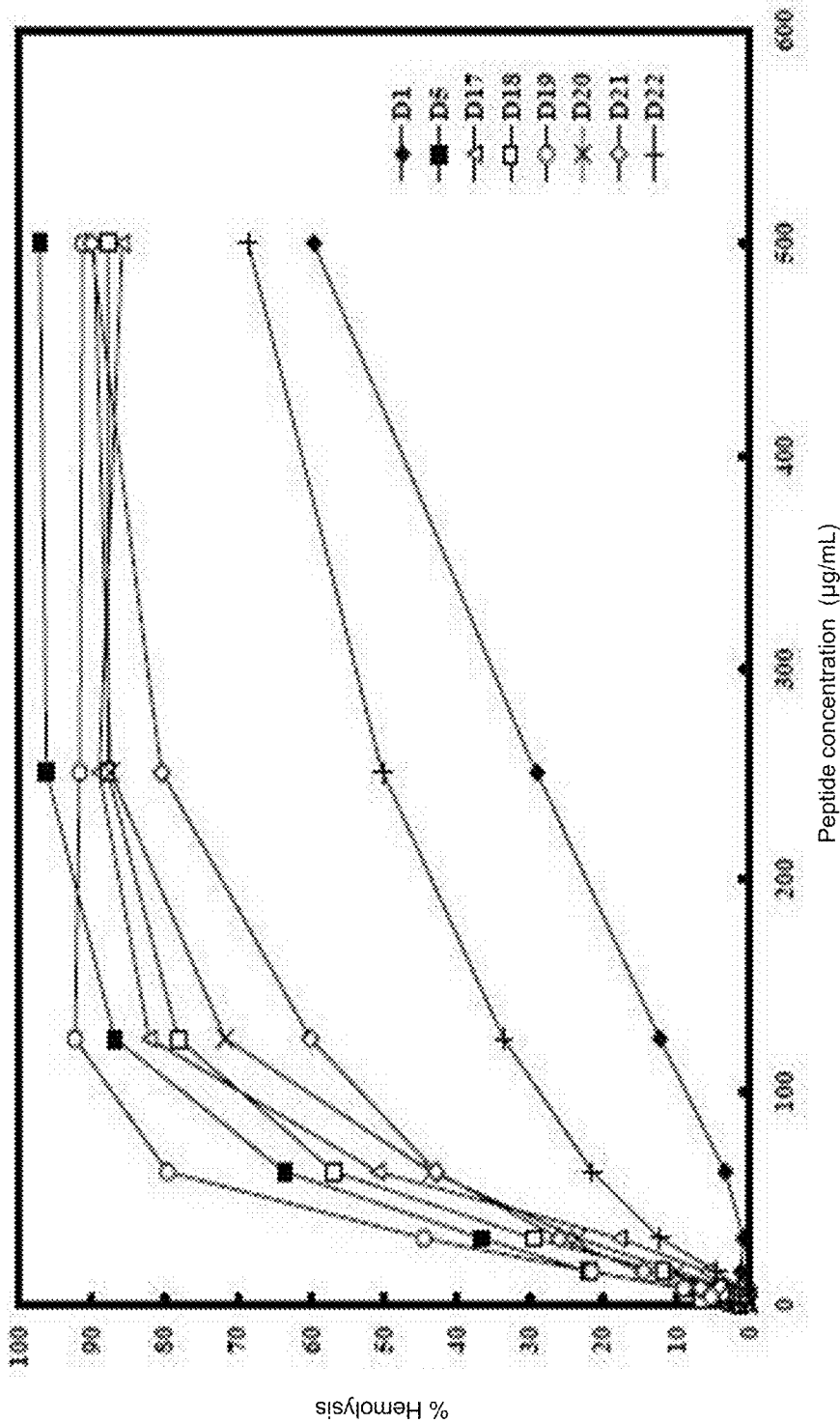
FIG. 4 shows the dependence of hemolysis on peptide concentration for peptides D1, D5 and D17-D22.

The hemolytic activities of the peptides against human erythrocytes were determined as a measure of peptide toxicity toward higher eukaryotic cells. The effect of peptide concentration on erythrocyte hemolysis is shown in FIG. 4. From these plots the peptide concentration that produced 50% hemolysis was determined ($HC_{50}$). Peptide D22 showed the weakest hemolytic activity among D17-D22, which increase in net positive charge from +5 for D17 up to +10 for D22. Hemolytic activity represented as $HC_{50}$ is shown in μg/ml. Increasing the number of positively charged residues on the polar face generally (but not in direct proportional relationship) decreases the hemolytic activity.

TABLE 8A

Antimicrobial Activities against *P. aeruginosa* and Hemolytic Activities of Peptides D17-D22 in comparison to Peptides D1 and D5

| Peptide Name | Net Charge | Hemolytic activity $HC_{50}(\mu g/mL)^a$ | Antimicrobial activity measured in Mueller Hinton medium $MIC(\mu g/mL)^b$ | | | | | | | Therapeutic index[d] | |
|---|---|---|---|---|---|---|---|---|---|---|---|
| | | | PAO 1 | PAK | PA 14 | CP 204 | WR 5 | M 2 | $GM^c$ | $HC_{50}$/MIC | Fold[e] |
| D1 | +7 | 421.5 | 7.8 | 15.6 | 15.6 | 15.6 | 15.6 | 7.8 | 12.4 | 34.0 | 1.00 |
| D5 | +8 | 47.0 | 7.8 | 15.6 | 7.8 | 15.6 | 15.6 | 7.8 | 11.0 | 4.3 | 0.13 |
| D17 | +5 | 62.0 | 15.6 | 15.6 | 15.6 | 31.3 | 31.3 | 31.3 | 22.1 | 2.8 | 0.08 |
| D18 | +6 | 55.0 | 7.8 | 7.8 | 7.8 | 15.6 | 15.6 | 7.8 | 9.8 | 5.6 | 0.16 |
| D19 | +7 | 36.0 | 3.9 | 3.9 | 3.9 | 15.6 | 15.6 | 15.6 | 7.8 | 4.6 | 0.14 |
| D20 | +8 | 77.0 | 7.8 | 7.8 | 7.8 | 31.3 | 15.6 | 15.6 | 12.4 | 6.2 | 0.18 |
| D21 | +9 | 88.5 | 7.8 | 3.9 | 0.5 | 15.6 | 15.6 | 15.6 | 6.2 | 14.2 | 0.42 |
| D22 | +10 | 249.0 | 3.9 | 3.9 | 0.5 | 31.3 | 31.3 | 15.6 | 7.0 | 35.6 | 1.05 |

[a]$HC_{50}$ is the maximal peptide concentration that produces 50% hemolysis of human red blood cells after 18 h in the standard microtiter dilution method.
[b]MIC is minimal inhibitory concentration that inhibited growth of different strains in Mueller-Hinton (MH) medium or Brain Heart Infusion (BHI) medium at 37° C. after 24 h. MIC is given based on three sets of determinations.
[c]GM, geometric mean of the MIC values.
[d]Therapeutic index is the ratio of the $HC_{50}$ value (μg/mL) over the geometric mean MIC value (μg/mL). Larger therapeutic index values generally indicate greater antimicrobial specificity.
[e]The fold improvement in therapeutic index compared to that of D1.

TABLE 8B

Antimicrobial Activities against *P. aeruginosa* and Hemolytic Activities of Peptides D17-D22 in comparison to Peptides D1 and D5

| Peptide Name | Net Charge | Hemolytic activity $HC_{50}(\mu g/mL)^a$ | Antimicrobial activity measured in Brain Heart Infusion medium $MIC(\mu g/mL)^b$ | | | | | | | Therapeutic index[d] | |
|---|---|---|---|---|---|---|---|---|---|---|---|
| | | | PAO 1 | PAK | PA 14 | CP 204 | WR 5 | M 2 | $GM^c$ | $HC_{50}$/MIC | Fold[e] |
| D1 | +7 | 421.5 | 31.3 | 31.3 | 15.6 | 62.5 | 15.6 | 62.5 | 31.2 | 13.5 | 1.00 |
| D5 | +8 | 47.0 | 31.3 | 31.3 | 15.6 | 31.3 | 15.6 | 15.6 | 22.1 | 2.1 | 0.16 |
| D17 | +5 | 62.0 | 31.3 | 31.3 | 15.6 | 62.5 | 62.5 | 31.3 | 35.1 | 1.8 | 0.13 |

TABLE 8B-continued

Antimicrobial Activities against *P. aeruginosa* and Hemolytic Activities of Peptides D17-D22 in comparison to Peptides D1 and D5

| Peptide Name | Net Charge | Hemolytic activity HC$_{50}$(μg/mL)[a] | Antimicrobial activity measured in Brain Heart Infusion medium MIC(μg/mL)[b] | | | | | | | Therapeutic index[d] | |
|---|---|---|---|---|---|---|---|---|---|---|---|
| | | | PAO 1 | PAK | PA 14 | CP 204 | WR 5 | M 2 | GM[c] | HC$_{50}$/MIC | Fold[e] |
| D18 | +6 | 55.0 | 10.4 | 10.4 | 10.4 | 41.7 | 20.8 | 10.4 | 14.7 | 3.7 | 0.28 |
| D19 | +7 | 36.0 | 7.8 | 15.6 | 3.9 | 15.6 | 15.6 | 7.8 | 9.8 | 3.7 | 0.27 |
| D20 | +8 | 77.0 | 7.8 | 15.6 | 7.8 | 15.6 | 7.8 | 7.8 | 9.8 | 7.8 | 0.58 |
| D21 | +9 | 88.5 | 15.6 | 3.9 | 3.9 | 15.6 | 3.9 | 3.9 | 6.2 | 14.3 | 1.06 |
| D22 | +10 | 249.0 | 15.6 | 7.8 | 3.9 | 31.3 | 15.6 | 3.9 | 9.8 | 25.3 | 1.88 |

[a]HC$_{50}$ is the maximal peptide concentration that produces 50% hemolysis of human red blood cells after 18 h in the standard microtiter dilution method.
[b]MIC is minimal inhibitory concentration that inhibited growth of different strains in Mueller-Hinton (MH) medium or Brain Heart Infusion (BHI) medium at 37° C. after 24 h. MIC is given based on three sets of determinations.
[c]GM, geometric mean of the MIC values.
[d]Therapeutic index is the ratio of the HC$_{50}$ value (μg/mL) over the geometric mean MIC value (μg/mL). Larger therapeutic index values generally indicate greater antimicrobial specificity.
[e]The fold improvement in therapeutic index compared to that of D1.

Antimicrobial Activity—

Widespread bacterial resistance to all commercially available antibiotic classes and their respective mechanisms of action is well documented (102). Recent reports reveal that the incidence of resistant gram-positive and gram-negative bacteria isolates generated in hospital patients exceeds 25% in several EU Member States (103). Bacterial resistance to antibiotics is having a dramatic impact on the global healthcare system. For example, 37,000 patients die in the EU annually from a multidrug-resistant hospital-acquired infection, resulting in healthcare costs of at least EUR 1.5 billion ($2.3B) each year (2), while in the U.S., annual healthcare costs related to the treatment of *P. aeruginosa*, alone, is estimated at $2.7 billion (104). Despite the tremendous expenditures to treat the problem, the CDC estimates that 99,000 deaths occurred in the U.S. in 2007 due to resistant infections within the healthcare system (105).

*Pseudomonas* is a genus of gram-negative bacteria with high intrinsic resistance to traditional antibiotics; thus, it is one of the most severe threats to human health. Resistance levels have been steadily increasing in recent years, and *P. aeruginosa* is also known to produce proteolytic enzymes that make it even less susceptible to antimicrobial peptides (60). The *P. aeruginosa* strains used in this study are a diverse group of clinical isolates from different places in the world, as noted herein.

Antimicrobial activities of peptide analogs against six clinical *P. aeruginosa* strains in two different media are shown in Tables 8A and 8B. The geometric means of MICs for six *P. aeruginosa* strains were calculated to provide an overall evaluation of the antimicrobial activities of the peptides with a different net charge. In Mueller Hinton medium, all the tested peptides except D17 have similar activity: their geometric mean MIC values were all low (varied from 6.2 μg/ml to 12.4 μg/ml) within a 2-fold difference (the geometric mean MIC value for D17 was 22.1 μg/ml). In Brain Heart Infusion medium, similar results were obtained for D17 to D22: their geometric mean MIC values were all low, i.e., varied from 6.2 μg/ml to 14.7 μg/ml, within a 2-fold difference except D17 which had a geometric mean MIC value of 35.1 μg/ml.

The biological activities of these six peptide analogs was determined against 11 clinical isolated of *Acinetobacter baumannii* (Table 9). Please note that the activities are reported in micromolar rather than microgram/ml. This allows a direct comparison on a molar basis with the effectiveness of molecules of different molecular weights whether peptides disclosed herein or antibiotics which in general are smaller in molecular mass. Members of the D17 to D22 charge-modification series are all extremely active, with a relatively tight range of GM-MIC values of 0.6 μM to 1.1 μM. These are the highest antimicrobial activities observed in studies of antimicrobial peptides derived by modifying the peptide sequence of SEQ ID NO:24 (D1). D22 has the best hemolytic activity of the six analogs (D17-D22) and a therapeutic index of 101.6 μM compared to 128.1 μM for D1 (Table 9). D22 has no apparent advantage over D1 as determined in these experiments.

TABLE 9

Antimicrobial Activities against *A. baumannii* and Hemolytic Activities of Peptides D1, D5 and D17-D22

| Peptide | Hemolytic activity HC$_{50}$[a] (μM) | Antimicrobial activity measured in Mueller Hinton medium MIC[b] (μM) | | | | | | | | | | | | Therapeutic index HC$_{50}$/MIC[d] |
|---|---|---|---|---|---|---|---|---|---|---|---|---|---|---|
| | | 1 ATCC 17978 — | 2 ATCC 19606 — | 3 649 Blood | 4 689 Groin | 5 759 Gluteus | 6 821 Urine | 7 884 Axilla | 8 899 Perineum | 9 964 Throat | 10 985 Pleural fluid | 11 1012 Sputum | GM[c] | |
| D1 | 140.9 | 0.8 | 1.5 | 0.8 | 0.8 | 1.5 | 1.5 | 1.5 | 1.5 | 1.5 | 0.8 | 0.8 | 1.1 | 128.1 |
| D5 | 14.9 | 2.5 | 1.3 | 1.3 | 1.3 | 1.3 | 2.5 | 1.3 | 1.3 | 2.5 | 2.5 | 2.5 | 1.7 | 8.8 |
| D17 | 21.7 | 0.7 | 0.7 | 0.7 | 0.7 | 0.7 | 0.7 | 0.7 | 0.7 | 0.7 | 0.7 | 0.7 | 0.7 | 31.0 |
| D18 | 19.0 | 1.3 | 1.3 | 0.7 | 0.7 | 1.3 | 0.7 | 1.3 | 0.7 | 1.3 | 0.7 | 0.7 | 0.9 | 21.1 |
| D19 | 12.2 | 0.7 | 0.7 | 1.3 | 0.7 | 1.3 | 0.7 | 0.7 | 0.7 | 1.3 | 0.7 | 0.7 | 0.8 | 15.3 |
| D20 | 25.8 | 0.3 | 0.7 | 0.7 | 0.7 | 0.7 | 0.7 | 0.7 | 0.3 | 0.7 | 0.7 | 0.3 | 0.6 | 43.0 |

TABLE 9-continued

Antimicrobial Activities against *A. baumannii* and Hemolytic Activities of Peptides D1, D5 and D17-D22

| | Hemolytic activity $HC_{50}^a$ (μM) | Antimicrobial activity measured in Mueller Hinton medium $MIC^b$ (μM) | | | | | | | | | | | Therapeutic index $HC_{50}/MIC^d$ |
|---|---|---|---|---|---|---|---|---|---|---|---|---|---|
| Peptide | | 1 ATCC 17978 — | 2 ATCC 19606 — | 3 649 Blood | 4 689 Groin | 5 759 Gluteus | 6 821 Urine | 7 884 Axilla | 8 899 Perineum | 9 964 Throat | 10 985 Pleural fluid | 11 1012 Sputum | $GM^c$ | |
| D21 | 29.3 | 1.3 | 1.3 | 1.3 | 1.3 | 1.3 | 1.3 | 0.7 | 0.7 | 1.3 | 1.3 | 0.7 | 1.1 | 26.6 |
| D22 | 81.3 | 0.7 | 1.3 | 1.3 | 1.3 | 0.7 | 0.7 | 0.7 | 0.7 | 0.7 | 0.7 | 0.7 | 0.8 | 101.6 |

$^a HC_{50}$ is the concentration of peptide that results in 50 hemolysis after 18 hours at 37° C.
$^b$MIC is the minimum inhibitory concentration of peptide that inhibits growth of bacteria after 24 hours at 37° C.
$^c$GM is the geometric mean of the MIC values from 11 different isolates of *Acinetobacter baumannii*.
$^d$Therapeutic index is the ratio of $HC_{50}$/GM-MIC value (e.g. the therapeutic index for D1 against *Acinetobacter baumannii* is 140.9/1.1 = 128.1).

Analogs with Enhanced Hydrophobicity and Variation in the Type of Hydrophobe on the Non-polar Face—

The biological activities of peptides D11 to D16, a hydrophobicity-modification series, are shown in Table 10. These peptides differ in hydrophobicity, the location of the hydrophobes and type of hydrophobe used on the non-polar face. These peptides are being compared to peptide D1 and D5 (D1, broad spectrum antimicrobial peptide and D5, most active analog against fungi and *M. tuberculosis*). This study shows four new peptides with dramatically improved therapeutic indices, as compared to D1. Peptides D11, D14, D15 and D16 have therapeutic indices against *A. baumannii* that are 3.3-fold, 3.4-fold, 2.7-fold and 26.0-fold better than D1, respectively.

logs, which have only one specificity determinant. D11 is a useful therapeutic agent for Gram-negative bacteria.

Figure 5A:
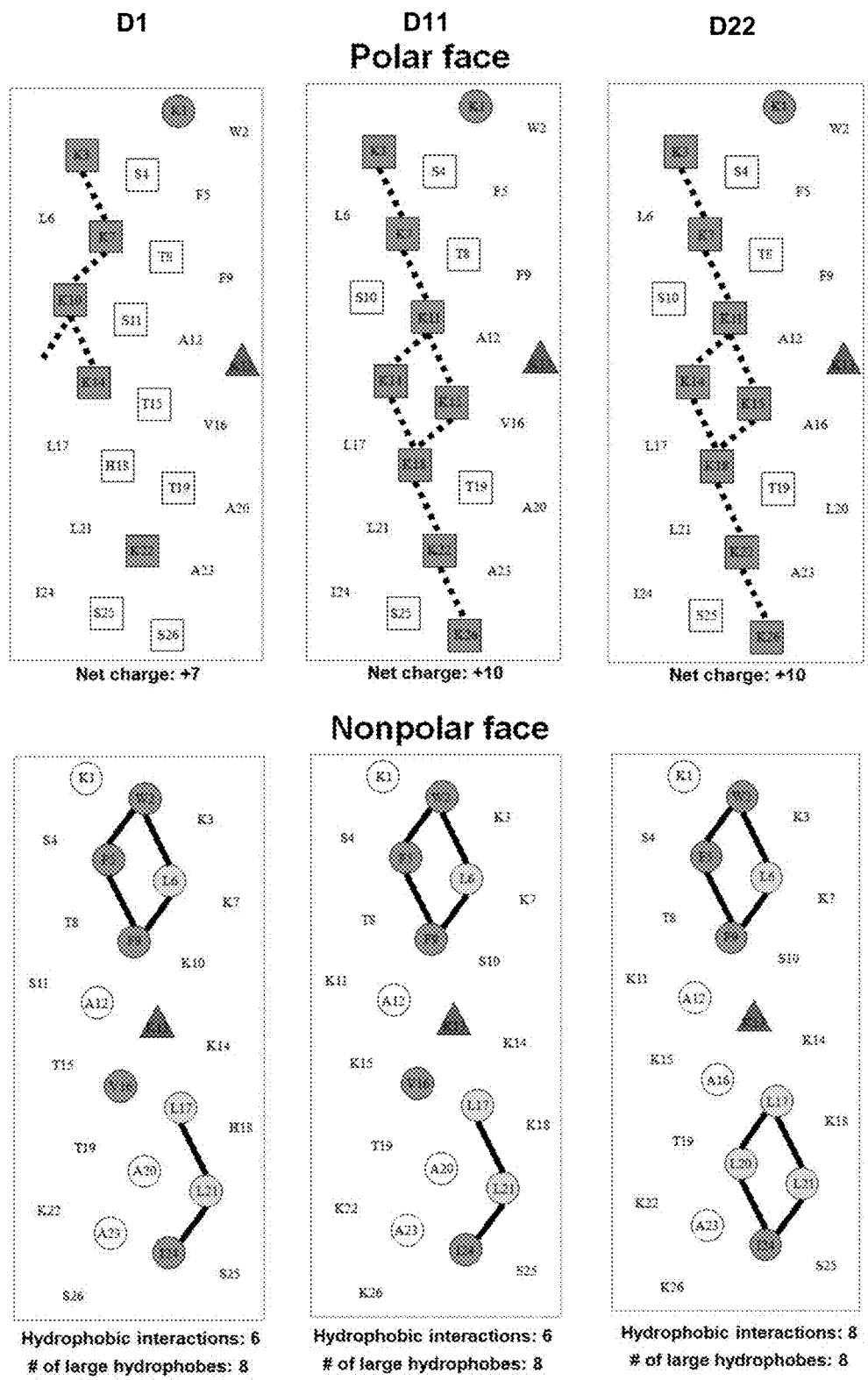
FIG. 5 shows D1, D11 and D22 peptide sequences represented as helical nets showing the polar face (top) and the non-polar face (bottom). Colored blue are lysine residues on the polar face and lightly shaded are large hydrophobic Leu residues on the non-polar face and darker shaded circles are other large hydrophobes on the non-polar face (Trp, Phe, Val and Ile). These three peptides have one specificity determinant colored pink, a lysine residue in the center of the non-polar face. See also SEQ ID NO:24 (D1), SEQ ID NO:63 (D11) and SEQ ID NO:74 (D22).

In FIGS. 5 and 6, D11 (SEQ ID NO:63) and D22 (SEQ ID NO:74), which have identical polar faces but different non-polar faces, are compared with D15 (SEQ ID NO:67): each has one specificity determinant (V13K) but D22 has more hydrophobic interactions (6 for D11 and 8 for D22 and the same number of large hydrophobes (8) with V16 in D11 changed to A16 in D22 and A20 in D11 changed to L20 in D22). The increased hydrophobicity of D22 dramatically increases hemolytic activity and thus decreases therapeutic index. D15, interestingly, is less hemolytic than D1, more active than the other two analogs, and thus has a much better

TABLE 10

Antimicrobial Activity against *A. baumannii*

| | Hemolytic activity $HC_{50}^a$ (μM) | Antimicrobial activity measured in Mueller Hinton medium $MIC^b$ (μM) | | | | | | | | | | | Therapeutic index HC50/MICd |
|---|---|---|---|---|---|---|---|---|---|---|---|---|---|
| Peptide | | 1 ATCC 17978 — | 2 ATCC 19606 — | 3 649 Blood | 4 689 Groin | 5 759 Gluteus | 6 821 Urine | 7 884 Axilla | 8 899 Perineum | 9 964 Throat | 10 985 Pleural fluid | 11 1012 Sputum | $GM^c$ | |
| D1 | 140.9 | 0.8 | 1.5 | 0.8 | 0.8 | 1.5 | 1.5 | 1.5 | 1.5 | 1.5 | 0.8 | 0.8 | 1.1 | 128.1 |
| D5 | 14.9 | 2.5 | 1.3 | 1.3 | 1.3 | 1.3 | 2.5 | 1.3 | 1.3 | 2.5 | 2.5 | 2.5 | 1.7 | 8.8 |
| D11 | 254.1 | 0.7 | 0.7 | 0.3 | 0.7 | 0.3 | 0.7 | 0.3 | 0.3 | 1.3 | 0.7 | 1.3 | 0.6 | 423.5 |
| D12 | 18.3 | 2.4 | 2.4 | 2.4 | 2.4 | 1.2 | 2.4 | 1.2 | 1.2 | 4.9 | 1.2 | 1.2 | 1.9 | 9.6 |
| D13 | 105.8 | 1.2 | 0.6 | 0.6 | 1.2 | 1.2 | 1.2 | 0.6 | 0.6 | 2.5 | 0.6 | 1.2 | 1.0 | 105.8 |
| D14 | 351.5 | 1.2 | 0.6 | 0.6 | 1.2 | 0.6 | 1.2 | 0.6 | 0.6 | 1.2 | 0.6 | 0.6 | 0.8 | 439.4 |
| D15 | 169.6 | 0.7 | 0.7 | 0.3 | 0.7 | 0.3 | 0.3 | 0.7 | 0.7 | 0.7 | 0.3 | 0.7 | 0.5 | 339.2 |
| D16 | 1342.0 | 0.7 | 0.7 | 0.3 | 0.3 | 0.7 | 0.3 | 0.3 | 0.3 | 0.7 | 0.3 | 0.3 | 0.4 | 3355.0 |

$^a HC_{50}$ is the concentration of peptide that results in 50 hemolysis after 18 hours at 37° C.
$^b$MIC is the minimum inhibitory concentration of peptide that inhibits growth of bacteria after 24 hours at 37° C.
$^c$GM is the geometric mean of the MIC values from 11 different isolates of *Acinetobacter baumannii*.
d Therapeutic index is the ratio of $HC_{50}$/GM-MIC value (e.g. the therapeutic index for D1 against *A. baumannii* is 140.9/1.1 = 128.1).

To better understand the structural differences in the peptide designs shown herein, comparison of small groups of peptides with their structures and corresponding activities are presented in FIGS. 5-8.

In FIG. 5, peptide D1 was compared with peptide D11 where both peptides are identical on the non-polar face but differ dramatically on the polar face (D1 is +7 and D11 is +10). This change on the polar face enhances antimicrobial activity for D11 against *A. baumannii* compare to D1. D11 has improved hemolytic activity resulting in an improved therapeutic index (423.5 vs 128.1 for peptide D1 against *A. baumannii*). Thus, D11 is a significant improvement over D1. D11 has the lowest hemolytic activity among these D-anatherapeutic index (339.2 for D15 as compared to 128.1 for D1. Accordingly, D15 is also useful therapeutic agent for microbial infections.

In FIG. 6, and Table 10, D11 and D15 and D14 and D16 are compared to show the effect of changing the type of hydrophobe with all other parameters being equal: D11 and D15 have identical polar and non-polar faces and one specificity determinant (V13K). The only difference between D11 and D15 is the change of 5 large hydrophobes (W2, F5, F9, V16, I24) to leucine residues. This change did not improve hemolytic activity. In fact, the hemolytic activity was greater from 254.1 μM for D11 to 169.6 μM for D15, and the resulting therapeutic index was lower: 423.5 to 339.2, respectively. This result contrasts with D14 and D16 which have identical polar and non-polar faces and two specificity determinants (V13K/V16K). The only difference between D14 and D16 is the change of 4 large hydrophobes (W2, F5, F9, I24) to leucine residues. This change of type of hydrophobe shows a dramatic improvement in hemolytic activity from 351.5 µM for D14 to 1342.0 µM for D16, and thus a dramatic improvement in therapeutic index from 439.4 to 3,355.0 (8-fold), respectively. This clearly demonstrates that changing all the hydrophobes to Leu residues can be tremendously advantageous, but it depends on the arrangement and location of the hydrophobes on the non-polar face prior to the change. Thus, it is context dependent. Based on these results, it is concluded that peptide D16 is useful as a therapeutic agent for treating infections, especially those caused by Gram-negative bacteria. Peptide D16 appears to have an unprecedented and unexpected 26-fold improvement in therapeutic index as compared to peptide D1.

D15 and D16 have identical polar faces and each has 8 leucine residues on the non-polar faces. The differences between D15 and D16 are as follows: 1) D15 has one specificity determinant (K13) and D16 has two specificity determinants (K13 and K16), 2) D15 has leucine at position 16 whereas D16 has leucine at position 20. We have significantly increased hydrophobicity of D16 compared to D15 which would increase hemolytic activity but to counter this effect the second specificity determinant greatly reduced hemolytic activity. These two effects result in 8-fold improvement in hemolytic activity ($HC_{50}$ for D16 is 1342 µM and D15 is 169.6 µM) and 10-fold improvement in therapeutic index to *A. baumannii* (3355.0 for D16 and 339.2 for D15). Thus, the combination of the correct hydrophobe arrangement and type of hydrophobe in conjunction with the two specificity determinants has resulted in the dramatic enhancement of the desired properties.

In FIG. 6 and Table 11, there is a comparison of D11 and D14: D11 and D14 have identical polar faces and each has 8 large hydrophobes on the non-polar faces but in different positions. The differences between D11 and D14 are as follows: 1) D11 has one specificity determinant (K13) and D14 has two specificity determinants (K13 and K16); 2) D11 has valine at position 16 whereas D14 has leucine at position 20. These differences have little effect (only a 1.4-fold improvement in hemolytic activity ($HC_{50}$ for D14 is 351.5 µM and D11 is 254.1 µM) and very similar therapeutic indices to *A. baumannii* (439.4 for D14 and 423.5 for D11). These results can be easily rationalized as follows: we have significantly increased hydrophobicity of D14 compared to D11 which would increase hemolytic activity but the hemolytic activity is reduced by adding the second specificity determinant so the two effects counter each other, keeping the therapeutic indices similar.

TABLE 11

Comparison of Peptides D1, D11, D14, D15 and D16 against *A. baumannii*

| Peptide | Hemolytic Activity $HC_{50}$ (µM) | Antimicrobial Activity MIC (µM) | Therapeutic Index $HC_{50}$/MIC |
|---|---|---|---|
| D1 | 140.9 | 1.1 | 128.1 |
| D11 | 254.1 | 0.6 | 423.5 |
| D15 | 169.6 | 0.5 | 339.2 |
| D14 | 351.5 | 0.8 | 439.4 |
| D16 | 1342.0 | 0.4 | 3355.0 |

Figures 1, 8:
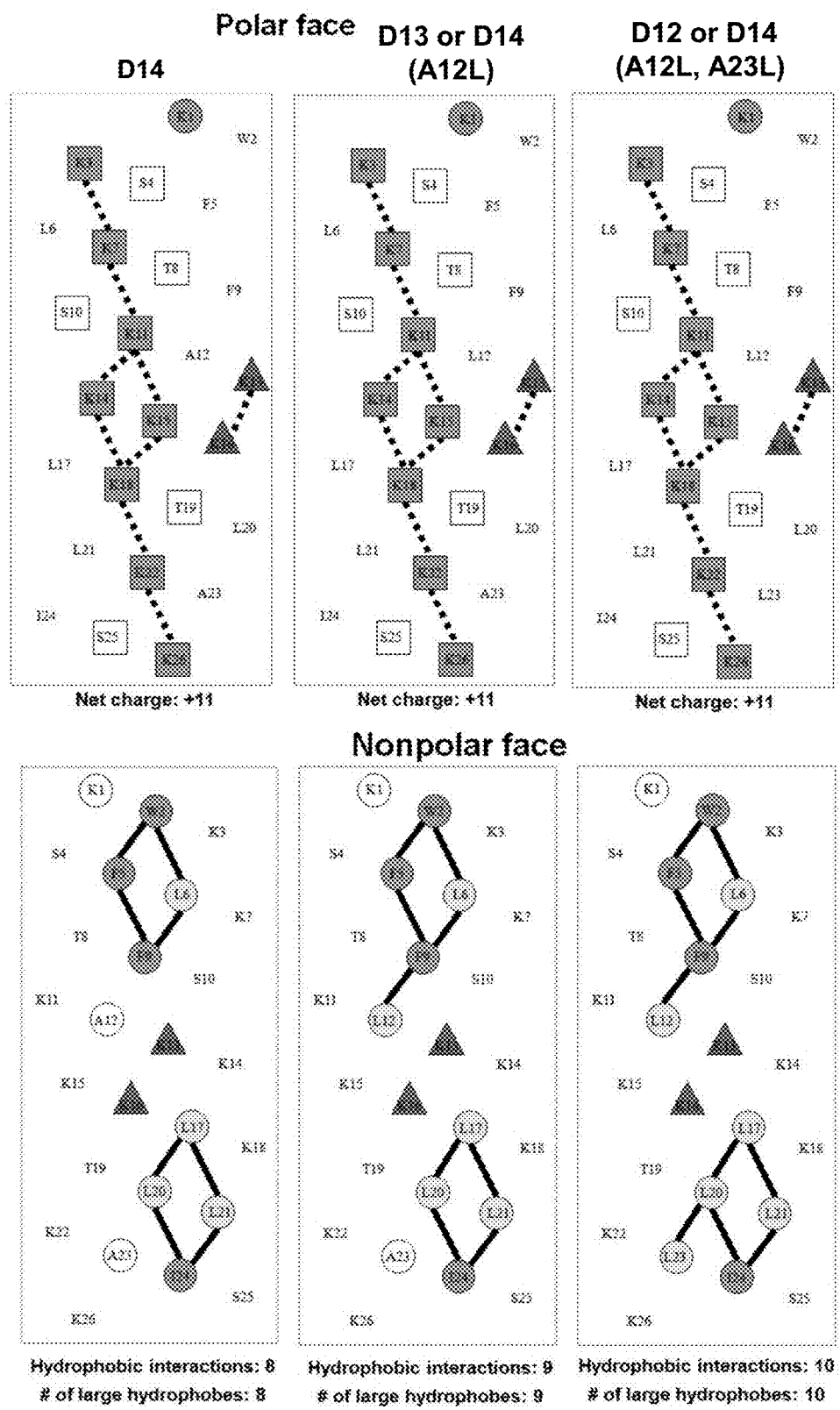
Figures 2, 8:
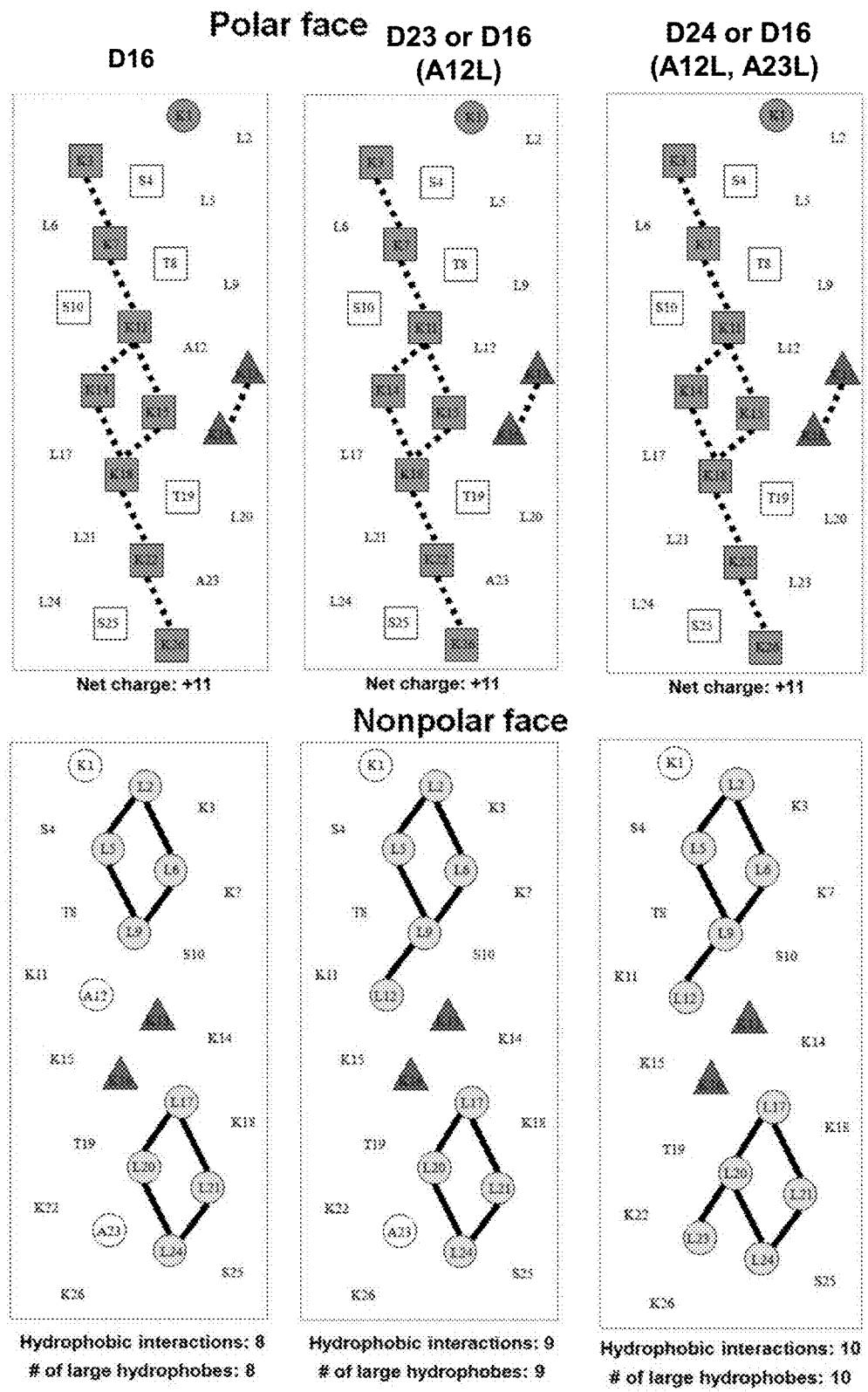

FIG. 8 compares D16, D23 and D24 and D14, D13 and D12. Peptides D12, D13 and D14 have identical polar faces but differ in the hydrophobicity at the non-polar faces. D13 has one additional substitution of Leu for Ala, thus is more hydrophobic than D14. D12 has one additional substitution of Leu for Ala thus is more hydrophobic than D13 (D14<D13<D12 in hydrophobicity). Interestingly, D14 the least hydrophobic analog of the three has the best activity and least hemolytic activity and the best therapeutic index of 439.4 compared to D12 with a therapeutic index of 9.6 (a 46-fold improvement for D14) which makes D14 a viable candidate compared to D1. In other words, increases in hydrophobicity of the non-polar face of D14 to D13 (D14 A12L) or D12 (D14 A12L, A23L) resulted in a dramatic increase in the hemolytic activity and thus a dramatic decrease in therapeutic index.

Similarly, further increases in hydrophobicity of the non-polar face of D16 to D23 (D16 A12L) or D24 (D16 A12L, A23L) resulted in a dramatic increase in the hemolytic activity (from 1342.0 mM for D16 to 122.7 mM for D24 and thus a decrease in therapeutic index from 3355.0 for D16 to 64.6 (a 52-fold effect) for D24. If we compare peptides D14 and D16, these peptides are identical on the polar face, identical on the non-polar face with regard to the location of the hydrophobes. The only difference is the change of Phe, Trp, and Ile residues to Leu residues in D16. This change has a small 2-fold improvement in antimicrobial activity and a 4-fold improvement in hemolytic activity leading to a 7.6 fold improvement in the therapeutic index (D16 has a therapeutic index of 3355 compared to 439.4 for D14). D16 has a remarkable activity profile, and it is a useful antimicrobial peptide for use in therapy against microbial infections. D16 is the most effective peptide tested to date for killing *Acinetobacter baumannii*, and this advantage is combined with a dramatic reduction in hemolytic activity (1342 mM for D16 compared to 351.5 mM for D14).

From the results shown herein, it is concluded that the hydrophobicity of D14 and D16 has been optimized and that the best arrangement of hydrophobes and type of hydrophobes on the nonpolar face is that of D16.

Therapeutic Index—

In Mueller Hinton medium (see above) where antimicrobial activity was measured against *P. aeruginosa*, only one peptide, D22, had a therapeutic index (35.6) similar to that of peptide D1 (34.0) (See Tables 8A and 8B). Interestingly, in Brain Heart Infusion medium, peptides D21 and D22 had therapeutic indices similar to or better than that of peptide D1. The therapeutic index for D1 was 13.5 (see data above), compared to peptide D21 with a value of 14.3, and peptide D22 with a value of 25.3. These results are surprisingly dramatic in that the number of positively charged residues and their location on the polar face compared to peptide D1 can be varied while achieving a significantly higher therapeutic index, as shown for peptide D22. It is important to note that peptide D22 has much higher overall hydrophobicity (90.7 min) than D1 (76.8 min). Thus, there can be a wide range of sequences varying in hydrophobicity on the non-polar face and the number and location of the positively charged residues on the polar face can vary and still maintain the desired biological properties. However, the changes must be complementary; that is, if hydrophobicity is increased on the non-polar face there must be a corresponding increase in the number of positively charged residues on the polar face. Because different sequences may be optimal for antimicrobial activity against a particular organism, the above discussion provides guidance for optimizing a particular amino acid sequence for a particular target microorganism, based on screening a reasonable number of peptide analogs that vary in positive charge on polar face and hydrophobicity on non-polar face of the helical peptide or helical domain of an antimicrobial peptide.

Figures 2, 6:
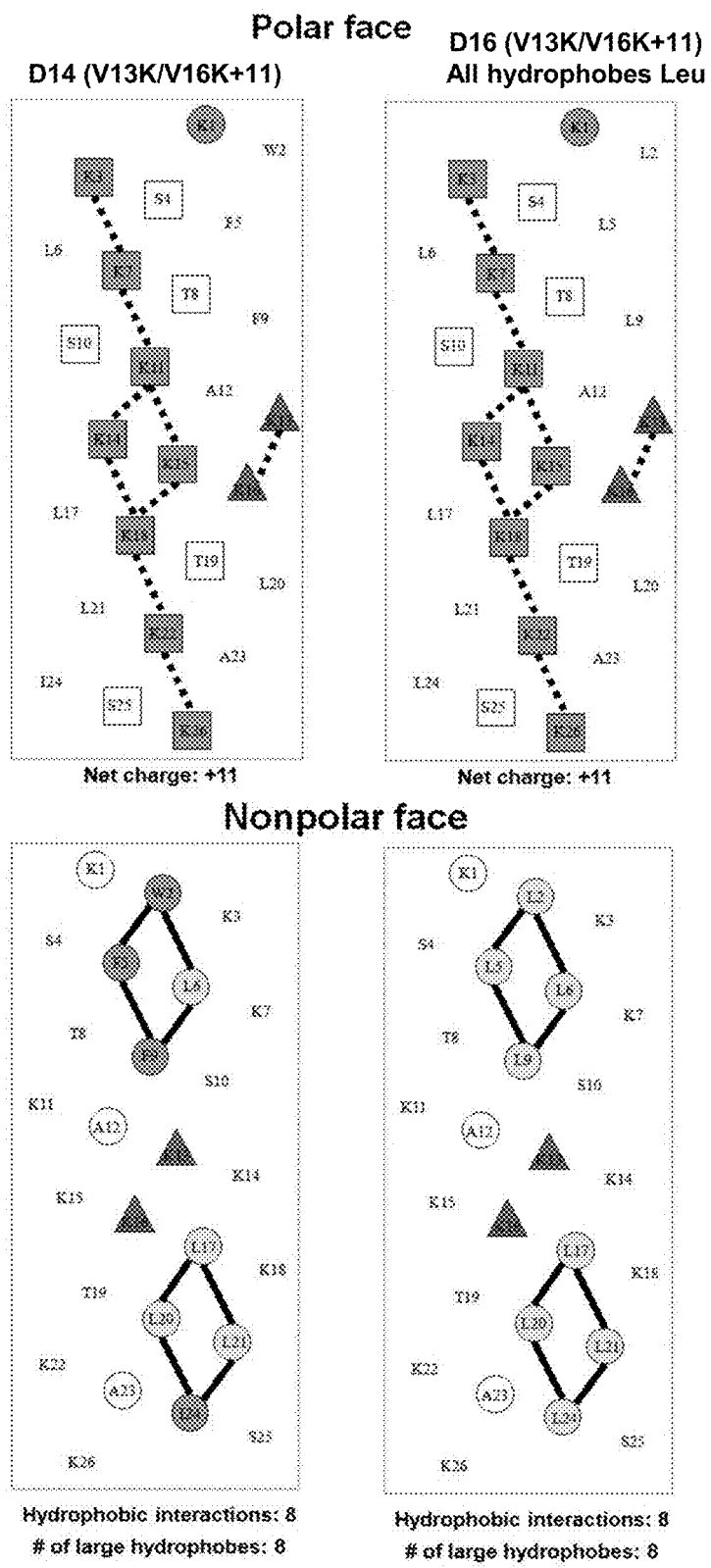

Provided herein are the results of a systematic study of varying the number of positively charged residues on the polar face of certain amphipathic α-helical antimicrobial peptides. The non-polar face is identical in the six antimicrobial peptides called D17 to D22 herein. As shown in FIG. 1A1-1A2, the number of lysine residues increases systematically from 4 (peptide D17), 5 (peptide D18), 6 (peptide D19), 7 (peptide D20), 8 (peptide D21) to 9 (peptide D22) on the polar face. All these peptides have one positively charged lysine residue on the non-polar face (what is referred to herein as a specificity determinant for reducing toxicity to human and other animal cells, thus the net charge on the peptides goes from +5 to +10).

Based on the results presented herein, increasing the number of positively charged residues on the polar face has very little affect on antimicrobial activity against six different strains of *Pseudomonas aeruginosa*.

By contrast, the hemolytic activity of these peptides decreased with the increasing number of positively charged residues on the polar face. In fact, peptide D22 is the least hemolytic peptide of the six. The higher the charge, the lower the hemolytic activity.

Table 12 summarizes the biological activities of peptides D11 to D16 and D22, D23 and D24 compared to D1 and D5 against two Gram-negative pathogens *Acinetobacter baumannii* (11 clinical isolates) and *Pseudomonas aeruginosa* (6 clinical isolates).

TABLE 12

Hemolytic Activity ($HC_{50}$), Antimicrobial Activity (MIC) and Therapeutic Index against *Acinetobacter baumannii* and *Pseudomonas aeruginosa* Clinical Isolates for Peptides D1, D5 plus D11 to D16 and D22 to D24.

| Peptide Name | Hemolytic activity $HC_{50}{}^{a}$ (mM) | Antimicrobial activity | | | |
|---|---|---|---|---|---|
| | | *Acinetobacter baumannii* | | *Pseudomonas aeruginosa* | |
| | | $MIC_{GM}{}^{b}$ (mM) | Therapeutic Index$^{c}$ | $MIC_{GM}{}^{b}$ (mM) | Therapeutic index$^{c}$ |
| D1 | 140.9 | 1.1 | 128.1 | 4.1 | 34.4 |
| D5 | 14.9 | 1.7 | 8.8 | 3.5 | 4.3 |
| D11 | 254.1 | 0.6 | 423.5 | 1.6 | 158.8 |
| D12 | 18.3 | 1.9 | 9.6 | 3.9 | 4.7 |
| D13 | 105.8 | 1.0 | 105.8 | 2.5 | 42.3 |
| D14 | 351.5 | 0.8 | 439.4 | 2.5 | 140.6 |
| D15 | 169.6 | 0.5 | 339.2 | 1.0 | 169.6 |
| D16 | 1342.0 | 0.4 | 3355.0 | 1.5 | 894.7 |
| D22 | 81.3 | 0.8 | 101.6 | 2.3 | 35.3 |
| D23 | 186.0 | 0.8 | 235.9 | 2.0 | 95.1 |
| D24 | 122.7 | 1.9 | 64.6 | 3.9 | 31.8 |

$^{a}HC_{50}$ is the concentration of peptide that results in 50% hemolysis after 18 hours at 37° C. The hemolytic activities that are better than the lead peptide D1 are bolded.
$^{b}$MIC is the minimum inhibitory concentration of peptide that inhibits growth of bacteria after 24 hours at 37° C.
$MIC_{GM}$ is the geometric mean of the MIC values from 11 different isolates of *A. baumannii* or 6 different isolates of *P. aeruginosa*.
$^{c}$Therapeutic index is the ratio of $HC_{50}/MIC_{GM}$ value. The therapeutic indices with values ≥ 100 for *A. baumannii* and ≥ 50 for *P. aeruginosa* are bolded.

Figure 9A:
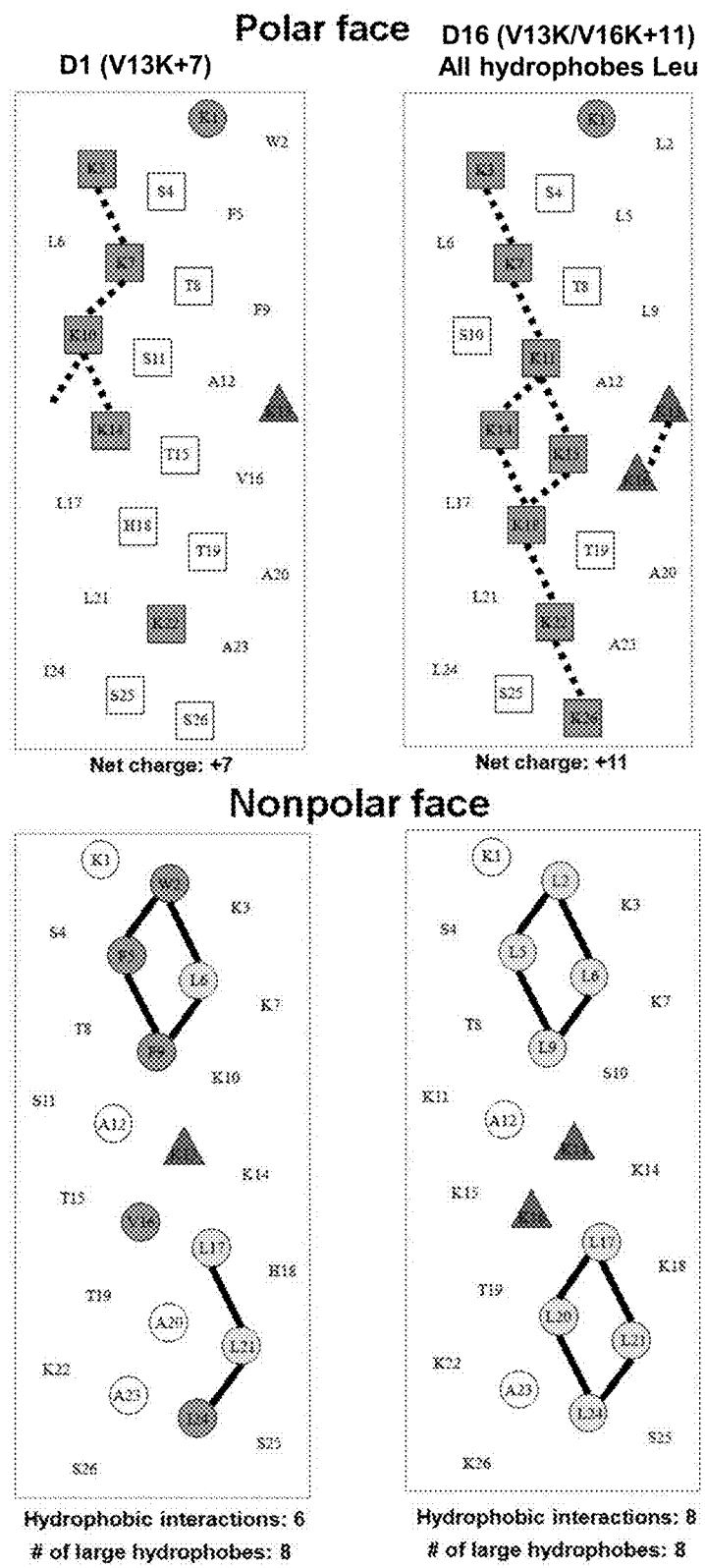
FIG. 9 shows D1 and D16 peptide represented as helical nets showing the polar faces (top) and the non-polar faces (bottom). Shaded triangles are lysine residues on the polar face and lightly shaded circles are large hydrophobic Leu residues on the non-polar face and darker shaded circles are all other large hydrophobes on the non-polar face (Trp, Phe, Val and Ile). These peptides have one and two specificity determinants, respectively, shown as shaded triangles (one or two Lys residues) in the center of the non-polar face. See also SEQ ID NO:24 (D1) and SEQ ID NO:68 (D16).

With respect to comparisons of broad spectrum antimicrobial activities of peptides D1 to D16 against *A. baumannii*, D16 is ~3-fold more active than D1 and 9.5 less hemolytic. The resulting therapeutic index for D16 is 26-fold better than D1 against this gram-negative bacterium. This was a remarkable discovery, and the structural differences between D1 and D16 are dramatic. The location and number of charged Lys residues on the polar face is very different (D1 contains 6 Lys on the polar face compared to 9 Lys residues for D16. D16 contains two specificity determinants in the center of the non-polar face (2 Lys residues) compared to one specificity determinant for D1. The number of hydrophobes, their location and type of hydrophobes are dramatically different for D16 (FIG. 9). Clearly, D16 is a useful antimicrobial agent, especially against gram-negative bacteria, including but not limited to *A. baumannii* and *P. aeruginosa*.

Without wishing to be bound by any particular theory, it is believed that the cluster of four positively charged residues in the center of the polar face is critical for enhancing antimicrobial activity. The analog the D19 has same net charge as D1 (D-V13K) but is more active (see Tables 8A and 8B).

Based on this series, D22 is believed the best antimicrobial of the series D17-D22, in that high antimicrobial activity is maintained and hemolytic activity is the lowest; thus, it has the best therapeutic index of the six analogs, as exemplified with *Pseudomonas aeruginosa* (see Tables 8A and 8B).

The data provided herein support the conclusion that dramatically changing the location and number of positively charged residues on the polar face allows for excellent therapeutic indices (compare the polar face of peptide D22 with peptide D1).

Note that the overall hydrophobicity of peptide D22 (retention time 90.67 min, see data herein above) is much greater than the overall hydrophobicity of peptide D1 (retention time 76.75 min, see above). The difference in hydrophobicity on the nonpolar face is shown in FIG. 1A-1B.

With the change from V16 to L20 (See Table 3), there is an increase in hydrophobicity and a change from 6 i→i+3/i→i+4 hydrophobic interactions in D1 to 8 i→i+3/i→i+4 hydrophobic interactions in D22. In fact, the "top half" of the molecule is identical on the non-polar face but the "bottom half" is different, with the engineering of a hydrophobic cluster in D22. Overall we conclude from this results that you can dramatically increase hydrophobicity on the non-polar face as long as there is an increase in the location and number of positively charged residues on the polar face, substantially the same therapeutic index is maintained. As specifically exemplified for peptides D17-D22, with *P. aeruginosa* as the target microorganism, the therapeutic index as measured in Mueller Hinton medium is maintained and the therapeutic index in Brain Heart Infusion medium is improved (See above).

It is emphasized that the properties and sequence of the polar face or the properties and sequence of the non-polar face can be varied dramatically while still maintaining similar activity profiles. But the changes must be complementary. Chen et al. 2007 demonstrated that a systematic increase in hydrophobicity on the non-polar face was detrimental to antimicrobial activity and hemolytic activity. To maintain the same level of therapeutic index, it is now known that it is necessary to change both faces in a complementary fashion and at the same time.

These results show that a wide range of sequences with the desired biological properties is possible. Because different sequences may be optimal for particular organisms, the above discussion enables optimization of a particular sequence for a particular organism, with screening of a reasonable number of peptide analogs that vary in positive charge on the polar face and hydrophobicity on the non-polar face of an antimicrobial peptide.

The role of hydrophobicity was investigated, with keeping 9 positively charged residues on the polar face to minimize hemolytic activity and maintain higher hydrophobicity than D1 (D-V13K). Shown below are six peptides (D11, D12, D13, D14, D15 and D16) that allow screening the effect of systematically increasing hydrophobicity on antimicrobial activity and hemolytic activity. These analogs have two lysine residues in the center of the non-polar face as specificity determinants to decrease toxicity to human cells, while having higher hydrophobicity than peptide D1. See SEQ ID NOs:63-68 for the amino acid sequences of peptides D11-D16 and SEQ ID NO:56 for D5. Peptide D5 exhibits stronger antimicrobial activity against fungi and *Mycobacterium tuberculosis* than does peptide D1.

To examine the importance of amino acid sequence of the hydrophobes on the non-polar face, constructs were made in which certain hydrophobes (W2, F5, F9, V16, I24) were replaced with leucine residues (compare peptide D11 to D15) and residues W2, F5, F9, I24 were substituted with leucine residues (compare D14 to D16). D11 has the sequence Ac-K-W-K-S-F-L-K-T-F-S-K-A-K-K-K-V-L-K-T-A-L-K-A-I-S-K-amide (SEQ ID NO:63); D12 has the sequence Ac-K-W-K-S-F-L-K-T-F-S-K-L-K-K-K-K-L-K-T-L-L-K-L-I-S-K-amide (SEQ ID NO:64); D13 has the sequence Ac-K-W-K-S-F-L-K-T-F-S-K-L-K-K-K-K-L-K-T-L-L-K-A-I-S-K-amide (SEQ ID NO:65), D14 has the Ac-K-W-K-S-F-L-K-T-F-S-K-A-K-K-K-K-L-K-T-L-L-K-A-I-S-K-amide (SEQ ID NO:66), D15 has the sequence Ac-K-L-K-S-L-L-K-T-L-S-K-A-K-K-K-L-L-K-T-A-L-K-A-L-S-K-amide (SEQ ID NO:67), and D16 has the sequence Ac-K-L-K-S-L-L-K-T-L-S-K-A-K-K-K-K-L-K-T-L-L-K-A-L-S-K-amide (SEQ ID NO:68). The results for these analogs show whether overall hydrophobicity is the only important factor or whether a combination of the hydrophobicity and sequence of the hydrophobes is key in determining antimicrobial and hemolytic activities.

According to the results provided herein, the best four peptides to date for use as antimicrobial agents against Gram-negative bacteria and for treating microbial infections are D11 and D15, each with one specificity determinant and same location of 8 large hydrophobes but different types of hydrophobes; and D14 and D16, each with two specificity determinants and same location of 8 large hydrophobes but different types of hydrophobes. The order of therapeutic indices: D16>>>D14≈D11≈D15.

Identification of Antimicrobial Peptides for Gram-positive Bacteria. In a manner similar to testing against gram-negative bacteria, experiments were carried out to screen the 14 peptides used to identify antimicrobial peptides with significant activity against *A. baumanii* shown above against 20 different clinical isolates of Methicillin Resistant *Staphylococcus aureus* (MRSA) and *Staphylococcus aureus*. The results are shown in Table 13 (peptides D1, D5 and D17-D22) and Table 14 (peptides D1, D5 and D11-D16).

Based on these results, peptides D11 and D15 are deemed to have significant antimicrobial activity profiles and acceptable hemolytic activities to give therapeutic indices of interest. In addition, both of these compounds are active against both antibiotic resistant and non-resistant isolates.

TABLE 13

Comparison of Hemolytic Activities and Antimicrobial Activities against 20 *S. aureus* strains

| | Hemolytic activity | Antimicrobial activity measured in Mueller Hinton medium $MIC^b$ (µM) | | | | | | | | | |
|---|---|---|---|---|---|---|---|---|---|---|---|
| Peptide | $HC_{50}^a$ (µM) | 1 | 2 $R^c$ | 3 | 4 $R^c$ | 5 | 6 | 7 $R^c$ | 8 | 9 $R^c$ | 10 | 11 $R^c$ |
| D1  | 140.9 | 23.9 | 12.0 | 23.9 | 23.9 | 23.9 | 23.9 | 3.0 | 95.5 | 12.0 | 12.0 | 12.0 |
| D5  | 14.9  | 7.3  | 7.3  | 7.3  | 3.7  | 7.3  | 3.7  | 3.7 | 14.7 | 7.3  | 3.7  | 3.7  |
| D17 | 21.7  | 21.9 | 11.0 | 21.9 | 21.9 | 21.9 | 43.7 | 2.7 | 43.7 | 21.9 | 11.0 | 21.9 |
| D18 | 19.0  | 26.0 | 13.0 | 26.0 | 13.0 | 26.0 | 26.0 | 3.2 | 51.9 | 13.0 | 13.0 | 13.0 |
| D19 | 12.2  | 5.3  | 5.3  | 10.6 | 5.3  | 10.6 | 5.3  | 1.3 | 5.3  | 5.3  | 2.7  | 5.3  |
| D20 | 25.8  | 5.2  | 5.2  | 10.5 | 5.2  | 10.5 | 5.2  | 2.6 | 5.2  | 5.2  | 5.2  | 5.2  |
| D21 | 29.3  | 5.2  | 5.2  | 10.4 | 5.2  | 10.4 | 5.2  | 1.3 | 20.7 | 5.2  | 5.2  | 10.4 |
| D22 | 81.3  | 10.2 | 10.2 | 20.4 | 10.2 | 20.4 | 10.2 | 2.5 | 40.8 | 10.2 | 10.2 | 20.4 |

| | Antimicrobial activity measured in Mueller Hinton medium $MIC^b$ (µM) | | | | | | | | | | Therapeutic |
|---|---|---|---|---|---|---|---|---|---|---|---|
| Peptide | 12 $R^c$ | 13 | 14 $R^c$ | 15 | 16 $R^c$ | 17 | 18 | 19 | 20 | $GM^d$ | index $HC_{50}MIC^e$ |
| D1  | 6.0  | 1.5 | 6.0  | 47.7 | 23.9 | 23.9 | 23.9 | 47.7 | 12.0 | 15.7 | 9.0 |
| D5  | 3.7  | 3.7 | 3.7  | 7.3  | 7.3  | 3.7  | 7.3  | 7.3  | 3.7  | 5.4  | 2.8 |
| D17 | 21.9 | 1.4 | 21.9 | 21.9 | 21.9 | 43.7 | 43.7 | 87.5 | 21.9 | 19.7 | 1.1 |
| D18 | 13.0 | 1.6 | 13.0 | 26.0 | 26.0 | 26.0 | 26.0 | 51.9 | 26.0 | 17.1 | 1.1 |
| D19 | 5.3  | 1.3 | 5.3  | 10.6 | 5.3  | 5.3  | 10.6 | 10.6 | 5.3  | 5.3  | 2.3 |
| D20 | 5.2  | 1.3 | 5.2  | 21.0 | 5.2  | 5.2  | 10.5 | 21.0 | 5.2  | 6.0  | 4.3 |
| D21 | 5.2  | 1.3 | 10.4 | 20.7 | 5.2  | 10.4 | 10.4 | 41.4 | 10.4 | 7.3  | 4.0 |
| D22 | 10.2 | 2.5 | 20.4 | 40.8 | 10.2 | 10.2 | 5.1  | 40.8 | 10.2 | 12.1 | 6.7 |

$^a HC_{50}$ is the concentration of peptide that results in 50% hemolysis after 18 hours at 37° C.
$^b$ MIC is the minimum inhibitory concentration of peptide that inhibits growth of bacteria after 24 hours at 37° C.
$^c$ R denotes MRSA strains resistant to the antibiotic Oxacillin.
$^d$ GM is the geometric mean of the MIC values from 20 different isolates of MRSA/SA.
$^e$ Therapeutic index is the ratio of $HC_{50}$/GM-MIC value (e.g. the therapeutic index for D1 against MRSA/SA is 140.9/15.7 = 9.0).

TABLE 14

Comparison of Hemolytic Activities and Antimicrobial Activities against 20 S. aureus strains

| Peptide | Hemolytic activity HC$_{50}$[a] (µM) | Antimicrobial activity measured in Mueller Hinton medium MIC[b] (µM) | | | | | | | | | |
|---|---|---|---|---|---|---|---|---|---|---|---|
| | | 1 | 2 R[c] | 3 | 4 R[c] | 5 | 6 | 7 R[c] | 8 | 9 R[c] | 10 | 11 R[c] |
| D1  | 140.9  | 23.9 | 12.0 | 23.9  | 23.9  | 23.9 | 23.9 | 3.0 | 95.5  | 12.0 | 12.0 | 12.0 |
| D5  | 14.9   | 7.3  | 7.3  | 7.3   | 3.7   | 7.3  | 3.7  | 3.7 | 14.7  | 7.3  | 3.7  | 3.7  |
| D11 | 254.1  | 10.3 | 10.3 | 41.0  | 20.5  | 10.3 | 20.5 | 0.7 | 41.0  | 10.3 | 5.1  | 20.5 |
| D12 | 18.3   | 4.9  | 4.9  | 9.8   | 4.9   | 4.9  | 4.9  | 1.2 | 9.8   | 4.9  | 4.9  | 4.9  |
| D13 | 105.8  | 4.9  | 4.9  | 19.8  | 4.9   | 9.9  | 9.9  | 0.6 | 19.8  | 4.9  | 9.9  | 9.9  |
| D14 | 351.5  | 20.0 | 20.0 | 160.2 | 40.1  | 40.1 | 80.1 | 0.6 | 160.2 | 40.1 | 40.1 | 40.1 |
| D15 | 169.6  | 5.3  | 10.7 | 21.4  | 5.3   | 10.7 | 10.7 | 0.3 | 21.4  | 5.3  | 5.3  | 10.7 |
| D16 | 1342.0 | 21.0 | 41.9 | 335.6 | 83.9  | 21.0 | 83.9 | 0.3 | 335.6 | 83.9 | 41.9 | 83.9 |

| Peptide | Antimicrobial activity measured in Mueller Hinton medium MIC[b] (µM) | | | | | | | | | | Therapeutic index HC$_{50}$MIC[e] |
|---|---|---|---|---|---|---|---|---|---|---|---|
| | 12 R[c] | 13 | 14 R[c] | 15 | 16 R[c] | 17 | 18 | 19 | 20 | GM[d] | |
| D1  | 6.0  | 1.5 | 6.0  | 47.7  | 23.9 | 23.9 | 23.9  | 47.7  | 12.0  | 15.7 | 9.0  |
| D5  | 3.7  | 3.7 | 3.7  | 7.3   | 7.3  | 3.7  | 7.3   | 7.3   | 3.7   | 5.4  | 2.8  |
| D11 | 10.3 | 0.7 | 10.3 | 82.0  | 20.5 | 10.3 | 41.0  | 163.9 | 20.5  | 14.0 | 18.2 |
| D12 | 2.4  | 0.3 | 2.4  | 19.5  | 9.8  | 9.8  | 9.8   | 19.5  | 9.8   | 5.2  | 3.5  |
| D13 | 4.9  | 0.6 | 9.9  | 39.5  | 9.9  | 9.9  | 19.8  | 79.0  | 19.8  | 8.6  | 12.3 |
| D14 | 40.1 | 1.2 | 40.1 | 160.2 | 80.1 | 40.1 | 80.1  | 320.4 | 80.1  | 40.1 | 8.8  |
| D15 | 5.3  | 0.7 | 5.3  | 42.8  | 10.7 | 5.3  | 21.4  | 85.5  | 10.7  | 8.1  | 20.9 |
| D16 | 41.9 | 0.3 | 10.5 | 335.6 | 83.9 | 83.9 | 167.8 | 335.6 | 167.8 | 48.3 | 27.8 |

[a]HC$_{50}$ is the concentration of peptide that results in 50% hemolysis after 18 hours at 37° C.
[b]MIC is the minimum inhibitory concentration of peptide that inhibits growth of bacteria after 24 hours at 37° C.
[c]R denotes MRSA strains resistant to the antibiotic Oxacillin.
[d]GM is the geometric mean of the MIC values from 20 different isolates of MRSA/SA.
[e]Therapeutic index is the ratio of HC$_{50}$/GM-MIC value (e.g. the therapeutic index for D1 against MRSA/SA is 140.9/15.7 = 9.0)

Without wishing to be bound by theory, it is believed that the factors important for antimicrobial peptides contributing to the desired properties of a clinical therapeutic to treat bacterial infections include the following: (1) the presence of positively charged residues resulting in a net positive charge; (2) in the case of structured molecules, cyclic β-sheet peptides and α-helical peptides, have an amphipathic nature that segregates basic and polar residues to one face of the molecule (polar face) and hydrophobic residues to the other face (non-polar face); (3) an optimum overall hydrophobicity; (4) the importance of lack of structure in aqueous conditions but inducible structure in the presence of the hydrophobic environment of the membrane; (5) the presence of "specificity determinant(s)," that is, a positively charged residue(s) in the center of the non-polar face of amphipathic cyclic β-sheet peptides and α-helical peptides which serve as a determinant(s) of specificity between prokaryotic and eukaryotic cell membranes, that is they reduce or eliminate toxicity as measured by hemolytic activity against human red blood cells; (6) these specificity determinants locate peptides to the interface region of prokaryotic membranes and decrease or eliminate transmembrane penetration into eukaryotic membranes; (7) the importance of eliminating or dramatically reducing peptide self-association in aqueous environment which allows the monomeric unstructured peptide to more easily pass through the cell wall components to reach the bacterial membrane; (8) the sole target for the antimicrobial peptide should be the bacterial membrane and the peptide should not be involved in any stereoselective interaction with chiral enzymes or lipids or protein receptors; (9) the use of the all D-enantiomer provides excellent peptide stability and resistance to proteolysis; and (10) the extent of binding to serum proteins must be modulated in the design process as only the unbound peptide is available to interact with the therapeutic target.

The reason it is so important to optimize overall peptide hydrophobicity is as follows: increasing hydrophobicity of α-helical or cyclic β-sheet antimicrobial peptides results in stronger hemolysis in erythrocytes or increased toxicity. In contrast, there is an optimum hydrophobicity window for antimicrobial activity. Decreasing hydrophobicity below the optimum decreases antimicrobial activity and increasing hydrophobicity above the optimum also decreases in antimicrobial activity probably due to increased peptide self-association. Peptide self-association stabilizes structured dimers/oligomers which can hinder or prevent peptide translocation through cell wall components to access the membrane in prokaryotic cells.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. It is not intended that any peptides disclosed in the prior art, except in prior applications from which priority may be claimed herein, are to be included in the present claimed invention in the United States, but peptides in the prior art are to be excluded from claimed peptides in countries outside the United States where priority is not claimed to an application which describes same.

The invention has been described with reference to various specific and preferred embodiments and techniques. However, it should be understood that many variations and modifications may be made while remaining within the true spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. It is not intended, however, for any claim herein to specifically encompass any precise embodiment existing and legally qualifying in the relevant jurisdiction as prior art for novelty; a claim purportedly encompassing such an embodiment is intended to be of scope so as to just exclude any such precise embodiment.

Whenever a range is disclosed, all subranges and individual values are intended to be encompassed. This invention is not to be limited by the embodiments disclosed, including any shown in the drawings or exemplified in the specification, which are given by way of example or illustration and not of limitation.

REFERENCES

1. Neu, H. C. (1992) *Science* 257, 1064-1073.
2. Travis, J. (1994) *Science* 264, 360-362.
3. Hancock, R. E. (1997) *Lancet* 349, 418-422.
4. Andreu, D., and Rivas, L. (1998) *Biopolymers* 47, 415-433.
5. Sitaram, N., and Nagaraj, R. (2002) *Curr Pharm Des* 8, 727-742.
6. Hancock, R. E., and Lehrer, R. (1998) *Trends Biotechnol* 16, 82-88.
7. Duclohier, H., Molle, G., and Spach, G. (1989) *Biophys J* 56, 1017-1021.
8. van't Hof, W., Veerman, E. C., Helmerhorst, E. J., and Amerongen, A. V. (2001) *Biol Chem* 382, 597-619.
9. Devine, D. A., and Hancock, R. E. (2002) *Curr Pharm Des* 8, 703-714.
10. Ganz, T., and Lehrer, R. I. (1994) *Curr Opin Immunol* 6, 584-589.
11. Steinberg, D. A., Hurst, M. A., Fujii, C. A., Kung, A. H., Ho, J. F., Cheng, F. C., Loury, D. J., and Fiddes, J. C. (1997) *Antimicrob Agents Chemother* 41, 1738-1742.
12. Khaled, M. A., Urry, D. W., Sugano, H., Miyoshi, M., and Izumiya, N. (1978) *Biochemistry* 17, 2490-2494.
13. Mootz, H. D., and Marahiel, M. A. (1997) *J Bacteriol* 179, 6843-6850.
14. Christensen, B., Fink, J., Merrifield, R. B., and Mauzerall, D. (1988) *Proc Natl Acad Sci USA* 85, 5072-5076.
15. Zasloff, M. (1987) *Proc Natl Acad Sci USA* 84, 5449-5453.
16. Andreu, D., Ubach, J., Boman, A., Wahlin, B., Wade, D., Merrifield, R. B., and Boman, H. G. (1992) *FEBS Lett* 296, 190-194.
17. Dathe, M., Wieprecht, T., Nikolenko, H., Handel, L., Maloy, W. L., MacDonald, D. L., Beyermann, M., and Bienert, M. (1997) *FEBS Lett* 403, 208-212.
18. Blondelle, S. E., and Houghten, R. A. (1992) *Biochemistry* 31, 12688-12694.
19. Lee, D. L., and Hodges, R. S. (2003) *Biopolymers* 71, 28-48.
20. Kondejewski, L. H., Jelokhani-Niaraki, M., Farmer, S. W., Lix, B., Kay, C. M., Sykes, B. D., Hancock, R. E., and Hodges, R. S. (1999) *J Biol Chem* 274, 13181-13192.
21. Oren, Z., Hong, J., and Shai, Y. (1997) *J Biol Chem* 272, 14643-14649.
22. Kondejewski, L. H., Lee, D. L., Jelokhani-Niaraki, M., Farmer, S. W., Hancock, R. E., and Hodges, R. S. (2002) *J Biol Chem* 277, 67-74.
23. Shai, Y., and Oren, Z. (1996) *J Biol Chem* 271, 7305-7308.
24. Oren, Z., and Shai, Y. (1997) *Biochemistry* 36, 1826-1835.
25. Lee, D. L., Powers, J. P., Pflegerl, K., Vasil, M. L., Hancock, R. E., and Hodges, R. S. (2004) *J Pept Res* 63, 69-84.
26. Chen, Y., Mant, C. T., and Hodges, R. S. (2002) *J Pept Res* 59, 18-33.
27. Zhang, L., Falla, T., Wu, M., Fidai, S., Burian, J., Kay, W., and Hancock, R. E. (1998) *Biochem Biophys Res Commun* 247, 674-680.
28. Zhang, L., Benz, R., and Hancock, R. E. (1999) *Biochemistry* 38, 8102-8111.
29. Mant, C. T., Chen, Y., and Hodges, R. S. (2003) *J Chromatogr A* 1009, 29-43.
30. Lee, D. L., Mant, C. T., and Hodges, R. S. (2003) *J Biol Chem* 278, 22918-22927.
31. Monera, O. D., Sereda, T. J., Zhou, N. E., Kay, C. M., and Hodges, R. S. (1995) *Journal of peptide science* 1, 319-329.
32. Eisenberg, D., Weiss, R. M., and Terwilliger, T. C. (1982) *Nature* 299, 371-374.
33. Carver, T., and Bleasby, A. (2003) *Bioinformatics* 19, 1837-1843.
34. Zhou, N. E., Monera, O. D., Kay, C. M., and Hodges, R. S. (1994) *Protein Peptide Lett.* 1, 114-119.
35. McInnes, C., Kondejewski, L. H., Hodges, R. S., and Sykes, B. D. (2000) *J Biol Chem* 275, 14287-14294.
36. Mant, C. T., Zhou, N. E., and Hodges, R. S. (1993) in *The Amphipathic Helix* (Epand, R. M., ed), pp. 39-64, CRC Press, Boca Raton
37. Mant, C. T., and Hodges, R. S. (2002) *J Chromatogr A* 972, 61-75.
38. Mant, C. T., and Hodges, R. S. (2002) *J Chromatogr A* 972, 45-60.
39. Zhou, N. E., Mant, C. T., and Hodges, R. S. (1990) *Pept Res* 3, 8-20.
40. Blondelle, S. E., Ostresh, J. M., Houghten, R. A., and Perez-Paya, E. (1995) *Biophys J* 68, 351-359.
41. Purcell, A. W., Aguilar, M. I., Wettenhall, R. E., and Hearn, M. T. (1995) *Pept Res* 8, 160-170.
42. Mant, C. T., Tripet, B., and Hodges, R. S. (2003) *J Chromatogr A* 1009, 45-59
43. Mant, C. T., and Hodges, R. S. (eds) (1991) *HPLC of peptides and proteins: separation, analysis and conformation*, CRC Press, Boca Raton, Fla.
44. Shai, Y. (1999) *Biochim Biophys Acta* 1462, 55-70.
45. Ehrenstein, G., and Lecar, H. (1977) *Q Rev Biophys* 10, 1-34.
46. Pouny, Y., Rapaport, D., Mor, A., Nicolas, P., and Shai, Y. (1992) *Biochemistry* 31, 12416-12423.
47. Salgado, J., Grage, S. L., Kondejewski, L. H., Hodges, R. S., McElhaney, R. N., and Ulrich, A. S. (2001) *J Biomol NMR* 21, 191-208.
48. Liu, F., Lewis, R. N., Hodges, R. S., and McElhaney, R. N. (2004) *Biophysical Journal* 87(4), 2470-82.
49. Liu, F., Lewis, R. N., Hodges, R. S., and McElhaney, R. N. (2004) *Biochemistry* 43, 3679-368.

50. Liu, F., Lewis, R. N., Hodges, R. S., and McElhaney, R. N. (2002) *Biochemistry* 41, 9197-9207.
51. Daum, G. (1985) *Biochim Biophys Acta* 822, 1-42.
52. Devaux, P. F., and Seigneuret, M. (1985) *Biochim Biophys Acta* 822, 63-125.
53. Chen, Y., Mant, C. T., Farmer, S. W., Hancock, R. E., Vasil, M. L. and Hodges, R. S. (2005) Rational design of alpha-helical antimicrobial peptides with enhanced activities and specificity/therapeutic index. *J Biol Chem* 280, 12316-12329.
54. Kovacs, J. M., Mant, C. T. and Hodges, R. S. (2006) Determination of intrinsic hydrophilicity/hydrophobicity of amino acid side-chains in peptides in the absence of nearest-neighbor or conformational effects. *Biopolymers (Peptide Science)* 84(3), 283-297.
55. Dolan, J. W. (2002) Temperature selectivity in reversed-phase high performance liquid chromatography. *J Chromatogr A* 965, 195-205.
56. Powers, J. P., Rozek, A. and Hancock, R. E. (2004) Structure-activity relationships for the beta-hairpin cationic antimicrobial peptide polyphemusin i. *Biochim Biophys Acta* 1698, 239-250.
57. Wade, D., Boman, A., Wahlin, B., Drain, C. M., Andreu, D., Boman, H. G. and Merrifield, R. B. (1990) All-d amino acid-containing channel-forming antibiotic peptides. *Proc Natl Acad Sci USA* 87, 4761-4765.
58. Hoiby, N. and Koch, C. (1990) Cystic fibrosis. 1. *Pseudomonas aeruginosa* infection in cystic fibrosis and its management. *Thorax* 45, 881-884.
59. Elkin, S, and Geddes, D. (2003) Pseudomonal infection in cystic fibrosis: The battle continues. *Expert Rev Anti Infect Ther* 1, 609-618.
60. Pierce, G. E. (2005) *Pseudomonas aeruginosa, Candida albicans*, and device-related nosocomial infections: Implications, trends, and potential approaches for control. *J Ind Microbiol Biotechnol* 32, 309-318.
61. Obritsch, M. D., Fish, D. N., Maclaren, R. and Jung, R. (2005) Nosocomial infections due to multidrug-resistant *Pseudomonas aeruginosa*: Epidemiology and treatment options. *Pharmacotherapy* 25, 1353-1364.
62. Al-Bakri, A. G., Gilbert, P. and Allison, D. G. (2005) Influence of gentamicin and tobramycin on binary biofilm formation by co-cultures of *Burkholderia cepacia* and *Pseudomonas aeruginosa*. *J Basic Microbiol* 45, 392-396.
63. Bodmann, K. F. (2005) Current guidelines for the treatment of severe pneumonia and sepsis. *Chemotherapy* 51, 227-233.
64. Avrahami, D. and Shai, Y. (2002) Conjugation of a magainin analogue with lipophilic acids controls hydrophobicity, solution assembly, and cell selectivity. *Biochemistry* 41, 2254-2263.
65. Wieprecht, T., Dathe, M., Beyermann, M., Krause, E., Maloy, W. L., MacDonald, D. L. and Bienert, M. (1997) Peptide hydrophobicity controls the activity and selectivity of magainin 2 amide in interaction with membranes. *Biochemistry* 36, 6124-6132.
66. Kustanovich, I., Shalev, D. E., Mikhlin, M., Gaidukov, L. and Mor, A. (2002) Structural requirements for potent versus selective cytotoxicity for antimicrobial dermaseptin s4 derivatives. *J Biol Chem* 277, 16941-16951.
67. Tachi, T., Epand, R. F., Epand, R. M. and Matsuzaki, K. (2002) Position-dependent hydrophobicity of the antimicrobial magainin peptide affects the mode of peptide-lipid interactions and selective toxicity. *Biochemistry* 41, 10723-10731.
68. Lugtenberg, B. and Van Alphen, L. (1983) Molecular architecture and functioning of the outer membrane of *Escherichia coli* and other gram-negative bacteria. *Biochim Biophys Acta* 737, 51-115.
69. Zilberstein, D., Schuldiner, S, and Padan, E. (1979) Proton electrochemical gradient in *Escherichia coli* cells and its relation to active transport of lactose. *Biochemistry* 18, 669-673.
70. Boman, H. G. (2003) Antibacterial peptides: Basic facts and emerging concepts. *J Intern Med* 254, 197-215.
71. Dathe, M., Schumann, M., Wieprecht, T., Winkler, A., Beyermann, M., Krause, E., Matsuzaki, K., Murase, O. and Bienert, M. (1996) Peptide helicity and membrane surface charge modulate the balance of electrostatic and hydrophobic interactions with lipid bilayers and biological membranes. *Biochemistry* 35, 12612-12622.
72. Wieprecht, T., Dathe, M., Krause, E., Beyermann, M., Maloy, W. L., MacDonald, D. L. and Bienert, M. (1997) Modulation of membrane activity of amphipathic, antibacterial peptides by slight modifications of the hydrophobic moment. *FEBS Lett* 417, 135-140.
73. Blondelle, S. E. and Houghten, R. A. (1991) Hemolytic and antimicrobial activities of the twenty-four individual omission analogues of melittin. *Biochemistry* 30, 4671-4678.
74. Kiyota, T., Lee, S, and Sugihara, G. (1996) Design and synthesis of amphiphilic alpha-helical model peptides with systematically varied hydrophobic-hydrophilic balance and their interaction with lipid- and bio-membranes. *Biochemistry* 35, 13196-13204.
75. Blondelle, S. E., Lohner, K. and Aguilar, M. (1999) Lipid-induced conformation and lipid-binding properties of cytolytic and antimicrobial peptides: Determination and biological specificity. *Biochim Biophys Acta* 1462, 89-108.
76. Hancock, R. E. and Rozek, A. (2002) Role of membranes in the activities of antimicrobial cationic peptides. *FEMS Microbiol Lett* 206, 143-149.
77. Sitaram, N. and Nagaraj, R. (1999) Interaction of antimicrobial peptides with biological and model membranes: Structural and charge requirements for activity. *Biochim Biophys Acta* 1462, 29-54.
78. Shai, Y. (1999) Mechanism of the binding, insertion and destabilization of phospholipid bilayer membranes by alpha-helical antimicrobial and cell non-selective membrane-lytic peptides. *Biochim Biophys Acta* 1462, 55-70.
79. Matsuzaki, K. (1999) Why and how are peptide-lipid interactions utilized for self-defense? Magainins and tachyplesins as archetypes. *Biochim Biophys Acta* 1462, 1-10.
80. Chen, Y., Mehok, A. R., Mant, C. T. and Hodges, R. S. (2004) Optimum concentration of trifluoroacetic acid for reversed-phase liquid chromatography of peptides revisited. *J Chromatogr A* 1043, 9-18.
81. Reddy, K. V., Yedery, R. D. and Aranha, C. (2004) Antimicrobial peptides: Premises and promises. *Int J Antimicrob Agents* 24, 536-547.
82. Brogden, K. A. (2005) Antimicrobial peptides: Pore formers or metabolic inhibitors in bacteria? *Nat Rev Microbiol* 3, 238-250.
83. Bland, J. M., De Lucca, A. J., Jacks, T. J. and Vigo, C. B. (2001) All-D-cecropin b: Synthesis, conformation, lipopolysaccharide binding, and antibacterial activity. *Mol Cell Biochem* 218, 105-111.
84. De Lucca, A. J., Bland, J. M., Vigo, C. B., Jacks, T. J., Peter, J. and Walsh, T. J. (2000) D-cecropin b: Proteolytic resistance, lethality for pathogenic fungi and binding properties. *Med Mycol* 38, 301-308.
85. Cribbs, D. H., Pike, C. J., Weinstein, S. L., Velazquez, P. and Cotman, C. W. (1997) All-D-enantiomers of beta-amyloid exhibit similar biological properties to all-L-beta-amyloids. *J Biol Chem* 272, 7431-7436.
86. Hamamoto, K., Kida, Y., Zhang, Y., Shimizu, T. and Kuwano, K. (2002) Antimicrobial activity and stability to proteolysis of small linear cationic peptides with D-amino acid substitutions. *Microbiol. Immunol* 46, 741-749.
87. Elmquist, A. and Langel, U. (2003) In vitro uptake and stability study of pVEC and its all-D analog. *Biol Chem* 384, 387-393.
88. Hong, S. Y., Oh, J. E. and Lee, K. H. (1999) Effect of D-amino acid substitution on the stability, the secondary structure, and the activity of membrane-active peptide. *Biochem Pharmacol* 58, 1775-1780.
89. Wakabayashi, H., Matsumoto, H., Hashimoto, K., Teraguchi, S., Takase, M. and Hayasawa, H. (1999) N-acylated and D enantiomer derivatives of a nonamer core peptide of lactoferricin B showing improved antimicrobial activity. *Antimicrob Agents Chemother* 43, 1267-1269.
90. Guo, D., Mant, C. T., Taneja, A. K., Parker, J. M. R. and Hodges, R. S. (1986) Prediction of peptide retention times in reversed-phase high-performance liquid chromatography. I. Determination of retention coefficients of amino acid residues using model synthetic peptides. *J Chromatogr* 359, 499-518.
91. Zhang L, Rozek A, Hancock R E. (2001) Interaction of cationic antimicrobial peptides with model membranes. J Biol Chem. 276(38), 35714-22.
92. Chen, Y., Vasil, A. I., Rehaume, L., Mant, C. T., Burns, J. L., Vasil, M. L., Hancock, R. E. and Hodges, R. S. (2006) Comparison of biophysical and biologic properties of alpha-helical enantiomeric antimicrobial peptides, Chem Biol Drug Des. 67, 162-73.
93. Chen, Y., Guarnieri, M. T., Vasil, A. I., Vasil, M. L., Mant, C. T. & Hodges, R. S. (2007) Role of peptide hydrophobicity in the mechanism of action of alpha-helical antimicrobial peptides, Antimicrob Agents Chemother. 51, 1398-406.
94. Chen, Y., Mant, C. T. & Hodges, R. S. (2007) Preparative reversed-phase high-performance liquid chromatography collection efficiency for an antimicrobial peptide on columns of varying diameters (1 mm to 9.4 mm I.D.), J Chromatogr A. 1140, 112-20.
95. Holloway, B. W. (1955) Genetic recombination in *Pseudomonas aeruginosa*, J Gen Microbiol. 13, 572-81.
96. Bjorn, M. J., Vasil, M. L., Sadoff, J. C. & Iglewski, B. H. (1977) Incidence of exotoxin production by *Pseudomonas* species, Infect Immun. 16, 362-6.
97. Pavlovskis, O. R., Pollack, M., Callahan, L. T., 3rd & Iglewski, B. H. (1977) Passive protection by antitoxin in experimental *Pseudomonas aeruginosa* burn infections, Infect Immun. 18, 596-602.
98. Frost, L. S. & Paranchych, W. (1977) Composition and molecular weight of pili purified from *Pseudomonas aeruginosa* K, J. Bacteriol. 131, 259-69.
99. Watts, T. H., Kay, C. M. & Paranchych, W. (1982) Dissociation and characterization of pilin isolated from *Pseudomonas aeruginosa* strains PAK and PAO, Can J. Biochem. 60, 867-72.
100. Rahme, L. G., Ausubel, F. M., Cao, H., Drenkard, E., Goumnerov, B. C., Lau, G. W., Mahajan-Miklos, S., Plotnikova, J., Tan, M. W., Tsongalis, J., Walendziewicz, C. L. and Tompkins, R. G. (2000) Plants and animals share functionally common bacterial virulence factors, Proc Natl Acad Sci USA. 97, 8815-21.
101. Stieritz, D. D. & Holder, I. A. (1975) Experimental studies of the pathogenesis of infections due to *Pseudomonas aeruginosa*: description of a burned mouse model, J Infect Dis. 131, 688-91.
102. Tenover, F. (2006). Mechanisms of Antimicrobial Resistance in Bacteria. The American Journal of Medicine. 119 (6A):S3-S10.
103. The bacterial Challenge: Time to React, European Centre for Disease Prevention and Control, 2009.
104. Spellberg, B., et al. (2007) Infection 35(3):167-74.
105. Centers for Disease Control website.

U.S. Patent Documents: U.S. Pat. Nos. 6,906,035, 6,818,407, 6,747,007, 6,465,429, 6,358,921, 6,337,317, 6,297,215, 6,288,212, 6,191,254, 6,172,185, 6,057,291, 6,040,435, 5,877,274, 5,789,377, 5,707,855, 5,688,767, 5,593,866, 20030228324, 20030021795, 6,872,806.

The invention claimed is:

1. A synthetic peptide having antimicrobial activity, said peptide comprising an amino acid sequence selected from the group consisting of:
- D11 (SEQ ID NO:63), D14 (SEQ ID NO:66), D15 (SEQ ID NO:67), D16 (SEQ ID NO:68), D21 (SEQ ID NO:73), D22 (SEQ ID NO:74), and D23 (SEQ ID NO:75);
- a peptide of one of the foregoing sequences in which there are all corresponding L amino acids;
- a peptide of one of the foregoing sequences in which there are all corresponding D amino acids; and
- a peptide of one of the foregoing sequences in which there is a mixture of L amino acids and D amino acids;
- wherein said synthetic peptide is optionally substituted with an acyl group at the N-terminus and/or an amide at the C-terminus in place of a carboxyl group.

2. The synthetic peptide of claim 1, wherein all amino acid residues are D-amino acid residues.

3. The synthetic peptide of claim 1 comprising SEQ ID NO:68.

4. A therapeutic composition for controlling infection by a microorganism, said composition comprising an effective amount of the synthetic peptide of claim 1 and a pharmaceutically acceptable carrier.

5. The therapeutic composition of claim 4, wherein the peptide is selected from the group consisting of D11 (SEQ ID NO:63), D14 (SEQ ID NO:66), D15 (SEQ ID NO:67), D16 (SEQ ID NO:68), D21 (SEQ ID NO:73), D22 (SEQ ID NO:74), and D23 (SEQ ID NO:75).

6. A method of inhibiting growth, replication, or infectivity of a microorganism, said method comprising the step of administering an effective amount of a composition comprising the synthetic peptide of claim 1.

7. The method of claim 6, wherein said microorganism is selected from the group consisting of a Gram-negative bacterium and a Gram-positive bacterium.

8. The method of claim 7, wherein the Gram-negative bacterium is *Pseudomonas aerugmosa*.

9. The method of claim 7, wherein the Gram-negative bacterium is *Acinetobacter baumannii*.

10. The method of claim 7, wherein the Gram-positive bacterium is *Staphylococcus aureus* or an antibiotic resistant *Staphylococcus aureus*.

11. The method of claim 6, wherein the synthetic peptide is selected from the group consisting of D11 (SEQ ID NO:63), D14 (SEQ ID NO:66), D15 (SEQ ID NO:67), D16 (SEQ ID NO:68), D21 (SEQ ID NO:73), D22 (SEQ ID NO:74), and D23 (SEQ ID NO:75).

12. A method of treating an infection in a subject caused by a microorganism, wherein said method comprises the step of administering a therapeutically effective amount of a composition to said subject, said composition comprising the synthetic peptide of claim 1.

13. The method of claim 12, wherein the peptide is selected from the group consisting of D11 (SEQ ID NO:63), D14 (SEQ ID NO:66), D15 (SEQ ID NO:67), D16 (SEQ ID NO:68), D21 (SEQ ID NO:73), D22 (SEQ ID NO:74), and D23 (SEQ ID NO:75).

14. The method of claim 12, wherein the microorganism is selected from the group consisting of Gram-positive bacteria and Gram-negative bacteria.

15. The method of claim 14, wherein the Gram-negative bacterium is *Pseudomonas aeruginosa* or *Acinetobacter baumannii*.

16. The method of claim 14, wherein the Gram-positive bacterium is *Staphylococcus aureus* or an antibiotic resistant *Staphylococcus aureus*.

17. A method of disinfecting a surface of an article, said method comprising the step of applying to said surface an effective amount of a composition comprising the synthetic peptide of claim 1.

18. A disinfecting solution comprising the synthetic peptide of claim 1.

19. An antimicrobial peptide consisting of SEQ ID NO:68.

20. A therapeutic composition for controlling infection by a microorganism, comprising an antimicrobial peptide consisting of SEQ ID NO:68, and a pharmaceutically acceptable carrier.

21. A method of treating an infection in a subject caused by a microorganism, comprising administering to said subject a therapeutically effective amount of a composition comprising an antimicrobial peptide consisting of SEQ ID NO:68, and a pharmaceutically acceptable carrier.

* * * * *